United States Patent
Evenhaim et al.

(10) Patent No.: US 12,406,754 B1
(45) Date of Patent: Sep. 2, 2025

(54) SYSTEMS AND METHODS FOR ANALYZING LONGITUDINAL HEALTH INFORMATION AND GENERATING A DYNAMICALLY STRUCTURED ELECTRONIC FILE

(71) Applicant: Veeva Systems Inc., Pleasanton, CA (US)

(72) Inventors: Asaf Evenhaim, New York, NY (US); Lindsey Lofgren, New York, NY (US); Myrto M. Miltiadous, Astoria, NY (US)

(73) Assignee: Veeva Systems Inc., Pleasanton, CA (US)

( * ) Notice: Subject to any disclaimer, the term of this patent is extended or adjusted under 35 U.S.C. 154(b) by 39 days.

(21) Appl. No.: 18/045,550

(22) Filed: Oct. 11, 2022

Related U.S. Application Data

(63) Continuation-in-part of application No. 17/472,360, filed on Sep. 10, 2021, now Pat. No. 11,551,794.

(51) Int. Cl.
*G06F 16/00* (2019.01)
*G06F 16/9535* (2019.01)
*G06F 16/955* (2019.01)
*G16H 10/60* (2018.01)

(52) U.S. Cl.
CPC ......... *G16H 10/60* (2018.01); *G06F 16/9535* (2019.01); *G06F 16/955* (2019.01)

(58) Field of Classification Search
None
See application file for complete search history.

(56) References Cited

U.S. PATENT DOCUMENTS

| | | |
|---|---|---|
| 8,595,206 B1 | 11/2013 | Ansari et al. |
| 8,918,385 B1 | 12/2014 | Ansari et al. |
| 10,185,809 B1 * | 1/2019 | Zhou ............... G16H 40/20 |
| 10,231,077 B2 | 3/2019 | Raduchel et al. |
| 10,553,307 B2 | 2/2020 | Connely, IV et al. |
| 10,586,614 B1 | 3/2020 | Cai et al. |
| 10,755,812 B1 | 8/2020 | Cai et al. |
| 10,769,181 B2 | 9/2020 | Bari et al. |
| 10,937,531 B1 | 3/2021 | Wang et al. |
| 11,107,578 B2 | 8/2021 | Nag |
| 11,551,794 B1 | 1/2023 | Lofgren et al. |
| 11,575,673 B2 | 2/2023 | Padmani et al. |
| 11,783,922 B1 | 10/2023 | Tong et al. |
| 11,868,506 B2 | 1/2024 | Johnson et al. |
| 11,948,112 B2 | 4/2024 | Crooks et al. |

(Continued)

*Primary Examiner* — Tony Mahmoudi
*Assistant Examiner* — Suman Rajaputra

(57) ABSTRACT

A method for generating a dynamically structured electronic file associated with a defined location. The method includes receiving health information from a covered entity computing system and a file generation request from a user computing device. The method further includes combining HCP information with the health information and determining multiple digitally projected values using at least one digital projection model. The method further includes generating the electronic file including at least one digitally projected value and at least a portion of the HCP location information. The electronic file is generated as the file type identified by the file generation request, and is structured based on at least one of the file generation request or the file destination.

19 Claims, 17 Drawing Sheets

(56) References Cited

U.S. PATENT DOCUMENTS

| | | |
|---|---|---|
| 11,989,326 B2 | 5/2024 | Levy et al. |
| 12,094,588 B1 | 9/2024 | Hermey et al. |
| 12,248,526 B1 | 3/2025 | Pushparajah et al. |
| 2002/0111833 A1 | 8/2002 | Dick |
| 2002/0116227 A1 | 8/2002 | Dick |
| 2002/0165736 A1 | 11/2002 | Tolle et al. |
| 2008/0300902 A1* | 12/2008 | Smith .................... G16H 20/10 705/1.1 |
| 2008/0306872 A1 | 12/2008 | Felsher |
| 2009/0048877 A1 | 2/2009 | Binns et al. |
| 2010/0131284 A1* | 5/2010 | Duffy .................... G16H 50/20 705/7.33 |
| 2010/0241595 A1 | 9/2010 | Felsher |
| 2010/0324936 A1* | 12/2010 | Vishnubhatla ......... G06Q 40/08 715/810 |
| 2011/0112862 A1 | 5/2011 | Yu |
| 2011/0112970 A1 | 5/2011 | Yu |
| 2011/0119088 A1 | 5/2011 | Gunn |
| 2011/0191343 A1 | 8/2011 | Heaton et al. |
| 2012/0191749 A1 | 7/2012 | New et al. |
| 2013/0073313 A1 | 3/2013 | Christakis et al. |
| 2014/0129256 A1* | 5/2014 | Veren .................... G06Q 10/10 705/3 |
| 2014/0136237 A1 | 5/2014 | Anderson et al. |
| 2014/0298030 A1 | 10/2014 | Akiyama et al. |
| 2015/0046192 A1 | 2/2015 | Raduchel |
| 2015/0112979 A1 | 4/2015 | Vittorio |
| 2015/0347599 A1 | 12/2015 | McMains et al. |
| 2016/0147945 A1 | 5/2016 | MacCarthy et al. |
| 2016/0210427 A1 | 7/2016 | Mynhier et al. |
| 2016/0358295 A1 | 12/2016 | Heffley et al. |
| 2017/0004266 A1 | 1/2017 | Vanderhoef |
| 2017/0161439 A1* | 6/2017 | Raduchel ............... G16H 10/60 |
| 2018/0121614 A1 | 5/2018 | Connely, IV et al. |
| 2018/0294048 A1 | 10/2018 | Blumenthal et al. |
| 2018/0322946 A1 | 11/2018 | Ika et al. |
| 2019/0252049 A1 | 8/2019 | Fotsch et al. |
| 2019/0304578 A1 | 10/2019 | Kain et al. |
| 2020/0005900 A1 | 1/2020 | Cha et al. |
| 2020/0035341 A1 | 1/2020 | Kain et al. |
| 2020/0202040 A1 | 6/2020 | Johnson et al. |
| 2020/0234826 A1 | 7/2020 | Said |
| 2021/0019296 A1 | 1/2021 | Petersen et al. |
| 2022/0117692 A1 | 4/2022 | Sellberg et al. |
| 2022/0270129 A1 | 8/2022 | Dakic et al. |
| 2022/0270729 A1 | 8/2022 | Saliman et al. |
| 2022/0319643 A1 | 10/2022 | Skees et al. |
| 2022/0319697 A1 | 10/2022 | Morris et al. |
| 2023/0104655 A1 | 4/2023 | Amarasingham et al. |
| 2023/0110360 A1 | 4/2023 | Sanae et al. |
| 2023/0144503 A1 | 5/2023 | Powers et al. |
| 2023/0148326 A1 | 5/2023 | Papel et al. |
| 2023/0273848 A1 | 8/2023 | Vera-Ciro et al. |
| 2023/0282322 A1 | 9/2023 | Rajkumar et al. |
| 2023/0368878 A1 | 11/2023 | Molenda |
| 2023/0385450 A1 | 11/2023 | Bessette et al. |
| 2024/0013899 A1 | 1/2024 | Youngblood et al. |
| 2024/0105289 A1* | 3/2024 | Khan .................... G16H 15/00 |
| 2024/0112771 A1 | 4/2024 | Shelton, IV et al. |
| 2024/0127932 A1 | 4/2024 | Bongiovanni et al. |
| 2025/0006352 A1 | 1/2025 | Schoenberg |
| 2025/0132043 A1 | 4/2025 | Ouimet |
| 2025/0166762 A1 | 5/2025 | Barkol et al. |
| 2025/0190621 A1 | 6/2025 | Boominathan et al. |

* cited by examiner

| NPI | VID | STATE | ZIP | SPECIALTY 1 | SPECIALTY 2 | HCP | NUMBER OF DIAGNOSES | DRUG 1 TRx | DRUG 2 TRx |
|---|---|---|---|---|---|---|---|---|---|
| 11112222333 | 21112222233 | STATE 1 | 11111 | RHEUMATOLOGY | GENERAL PRACTICE | DOCTOR OF MEDICINE | 66 | 1 | 25 |
| 11112222334 | 21112222234 | STATE 2 | 11112 | INTERNAL MEDICINE | RHEUMATOLOGY | DOCTOR OF MEDICINE | 31 | 1 | |
| 11112222335 | 21112222235 | STATE 3 | 11113 | HOSPITALIST | RHEUMATOLOGY | DOCTOR OF MEDICINE | 20 | 1 | |
| 11112222336 | 21112222236 | STATE 4 | 11114 | INTERNAL MEDICINE | ENDOCRINOLOGY | DOCTOR OF MEDICINE | 62 | | 5 |

FIG. 8A

| DRUG 3 TRx | DRUG 4 TRx | DRUG 5 TRx | DRUG 6 TRx | DRUG 7 TRx | DRUG 8 TRx | DRUG 1 NBx | DRUG 2 NBx | DRUG 3 NBx | DRUG 4 NBx | DRUG 5 NBx | DRUG 6 NBx | DRUG 7 NBx | DRUG 8 NBx | # TOTAL PATIENTS | % MEDICARE | % MEDICAID |
|---|---|---|---|---|---|---|---|---|---|---|---|---|---|---|---|---|
| 4 | | | | | | 1 | 8 | 1 | | | | | | 198 | 30 | 10 |
| 15 | 12 | | | | | | | 2 | | | | | | 93 | 32 | 11 |
| 10 | | | | | 7 | | | 1 | | | | | 2 | 160 | 33 | 10 |
| 22 | 2 | | | | 30 | | 1 | 3 | | | | | 3 | 86 | 34 | 4 |

FIG. 8B

| % COMMERCIAL | % CASH | % 0-10,000 | % 10,001- 40,000 | % 40,001- 90,000 | % 90,001- 120,000 | % 120,001- 200,000 | % 200,001- 500,000 | % 500,000+ |
|---|---|---|---|---|---|---|---|---|
| 42 | 10 | 6 | 19 | 40 | 16 | 12 | 5 | 2 |
| 52 | 5 | 4 | 21 | 22 | 33 | 12 | 7 | 1 |
| 48 | 9 | 0 | 10 | 41 | 28 | 10 | 7 | 4 |
| 52 | 10 | 0 | 1 | 24 | 48 | 16 | 9 | 2 |

FIG. 8C

| PRODUCT_NAME | TIME_DIMENSION | TIME_VALUE | YEAR | DATE_ENDING | GEOGRAPHY | GEOGRAPHY_DES | MEASUREMENT | VALUE |
|---|---|---|---|---|---|---|---|---|
| DRUG A | MONTH | 1 | 2021 | 2021-01-31 | 90640 | ZIP5-90640 | TRX | 1 |
| DRUG A | MONTH | 1 | 2021 | 2021-01-31 | 680 | ZIP5-00680 | TRX | 4 |
| DRUG A | MONTH | 1 | 2021 | 2021-01-31 | 8822 | ZIP5-08822 | TRX | 10 |
| DRUG A | MONTH | 1 | 2021 | 2021-01-31 | 10013 | ZIP5-10013 | TRX | 787 |
| DRUG A | MONTH | 1 | 2021 | 2021-01-31 | 32771 | ZIP5-32771 | TRX | 1001 |
| DRUG A | MONTH | 1 | 2021 | 2021-01-31 | 31021 | ZIP5-31021 | TRX | 54 |
| DRUG A | MONTH | 1 | 2021 | 2021-01-31 | 90505 | ZIP5-90505 | TRX | 77 |
| DRUG A | MONTH | 1 | 2021 | 2021-01-31 | 94115 | ZIP5-94115 | TRX | 23 |

FIG. 11

1100

SYSTEMS AND METHODS FOR ANALYZING LONGITUDINAL HEALTH INFORMATION AND GENERATING A DYNAMICALLY STRUCTURED ELECTRONIC FILE

CROSS-REFERENCE TO RELATED APPLICATIONS

This application is a Continuation-In-Part of U.S. patent application Ser. No. 17/472,360, filed Sep. 10, 2021, which is hereby incorporated by reference in its entirety.

TECHNICAL FIELD

The present disclosure relates to systems and methods for analyzing longitudinal health information and generating a dynamically structured electronic file.

BACKGROUND

Researchers, scientists, industry players, academics, government regulators, and other stakeholders are increasingly in need of longitudinal health information and location-specific insights that are accessible, easy to interpret, analyze, and/or visualize.

SUMMARY

One embodiment relates to a method for generating a dynamically structured electronic file associated with a defined location. The method includes receiving government health information including location information from a national health database and generating a health information request. The method further includes providing the health information request to the one or more covered entity computing systems. The method further includes receiving health information including deidentified protected health information (PHI) from the one or more covered entity computing systems and health care provider (HCP) information including HCP location information. The method further includes combining the health information with the HCP location information to generate combined health information. The method further includes selecting one or more digital projection models from a projection model database. The method further includes determining multiple digitally projected values based on at least one of the combined health information or the government health information using at least one of the one or more digital projection models. Each digitally projected value of the plurality of digitally projected values is associated with a specific location. The method further includes receiving a file generation request from the user computing device. The file generation request identifying a file and including a file destination address and a defined location. The method further includes filtering the multiple digitally projected values for the defined location of the file generation request by removing digitally projected values that are not associated with the defined location. The method further includes generating the electronic file including the filtered digitally projected values and at least a portion of the location information or the HCP location information. The electronic file is generated as the file type identified by the file generation request. The electronic file is structured based on at least one of the file generation request or the file destination. The method further includes providing the electronic file to the file destination address of the file generation request.

Another embodiment relates to a method for generating a dynamically structured electronic file associated with a defined location. The method includes receiving government health information including location information from a national health database. The method further includes receiving health information including deidentified protected health information (PHI) from the one or more covered entity computing systems and health care provider (HCP) information including HCP location information. The method further includes combining the health information with the HCP location information to generate combined health information. The method further includes selecting one or more digital projection models from a projection model database. The method further includes determining a first set of digitally projected values based on the government health information using the one or more digital projection models and a second set of digitally projected values based on the combined health information and the government health information using at least one of the one or more digital projection models. Each digitally projected value of the first set of digitally projected values and the second set of first set of digitally projected values is associated with a specific location. The method further includes receiving a file generation request from the user computing device. The file generation request identifying a file and including a file destination address and a defined location. The method further includes filtering the first set and second set of digitally projected values for the defined location of the file generation request by removing digitally projected values that are not associated with the defined location. The method further includes generating the electronic file including the filtered digitally projected values and at least a portion of the location information or the HCP location information. The electronic file is generated as the file type identified by the file generation request. The electronic file is structured based on at least one of the file generation request or the file destination. The method further includes providing the electronic file to the file destination address of the file generation request.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

FIGS. 8A-8C are an illustration of some aspects of an electronic HCP file generated by the longitudinal health information analyzation and dynamically structured electronic file generation system of FIG. 1, according to an example embodiment.

FIG. 11 is an illustration of some aspects of an electronic defined location prescribing file generated by the longitudinal health information analyzation and dynamically structured electronic file generation system of FIG. 1, according to an example embodiment.

DETAILED DESCRIPTION

Figure 1:
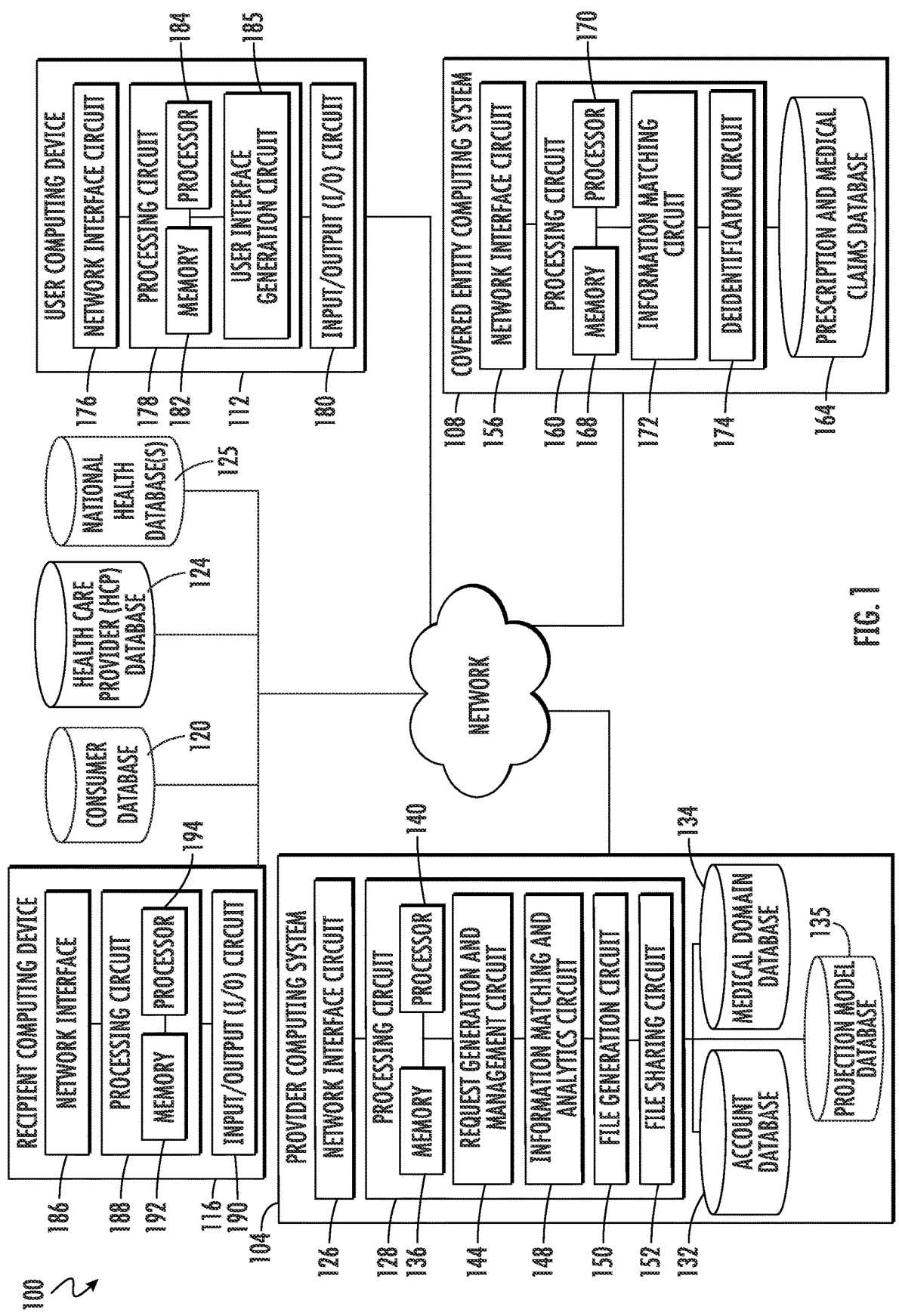
FIG. 1 is a component diagram of a longitudinal health information analyzation and dynamically structured electronic file generation system, according to an example embodiment.

Referring generally to the figures, systems and methods for analyzing longitudinal health information and generating a dynamically structured electronic HCP file are disclosed. The systems and methods described herein provide for enhanced analyzation of longitudinal health information and generation HCP insights by utilizing a wide variety of longitudinal health information, HCP information, and consumer information. For example, because the systems and methods described utilize longitudinal health information including consistently deidentified private health information (PHI), the systems described herein can make associations across all the received information while protecting the patients' identities based solely on the deidentified PHI of the health information, which reduces the complexity of the analysis of the longitudinal health information, HCP information, and consumer information and therefore requires less processing power by the systems described herein. For example, instead of having to associate separately received health information based on multiple matching attributes (e.g., zip code, type of medical coverage, cost of medical procedure, etc.), the systems described herein can associate the separately received health information based solely on the deidentified PHI of the health information, due to the consistent deidentification of the PHI.

The systems and methods described herein further provide for improved structuring and generation of electronic files (also referred herein as HCP files or defined location prescribing files). For example, because the electronic file is dynamically structured and includes specific HCP information, health information, and HCP insights, as decided by a user, the electronic file does not include excess or unwanted values and therefore requires less memory to be stored and less processing power to be shared between computing devices and systems. For example, if the electronic file were generated as a statically structured file (e.g., included the same values every time) and still included all the values, insights, and information described herein, the electronic file would include excess information that was unwanted by the user or the computing device/system to which the electronic file is provided. The excess information would make the electronic file larger, thereby requiring additional memory to store the electronic file and additional processing power to generate and share the electronic file. In comparison, because the systems and methods described herein dynamically structure the electronic file, as decided by the user and/or the device/system to which the electronic file is provided, the electronic file includes only requested information and HCP insights, reducing the memory required by the provider computing system to store the electronic file and processing power required by the provider computing system to generate and share the electronic file.

Likewise, because the electronic file is dynamically generated as a specified file type, as decided by the user or the computing device/system to which the electronic file is provided, the systems and methods described herein may provide for improved shareability of the electronic file as well as use less processing power and memory. For example, in situations where the electronic file is only generated as a static file type, third-party computing systems and recipient computing devices (e.g., the recipient computing device) may have to perform additional file modification and conversion or request the provider computing system to do so, which requires additional processing power, memory (to keep two files), and time. In comparison, the systems and methods described herein allow the user to specify the file type of the electronic file through the electronic file generation request. Accordingly, the user can specify the wanted file type the first time and the provider computing system will generate the electronic file as the specified file type. As a result, no additional file modification or conversion is required reducing processing power usage, memory usage, and overall processing time for the provider computing system.

In an illustrative scenario, the provider computing system 104 may generate a health information request and provide the health information request to one or more covered entity computing systems. The covered entity computing systems, in response to the health information request, may determine health information matching the health information request, consistently deidentify PHI of the health information, and provide the health information, including the deidentified PHI to the provider computing system. The provider computing system may then receive an electronic file generation request from a user computing device and match the HCP information with the received health information. The provider computing system may further determine one or more HCP statistical values or insights based on the matched electronic file generation request, the matched HPC information, and the matched health information. The provider computing system may then generate an electronic file including the matched HCP information, the matched health information, and the HCP statistical values based solely on the HCP file generation request and as a specific file type based on the electronic file generation request.

The provider computing system may store the electronic file in a database as well as provide the electronic file to a file destination. Lastly, the provider computing system may receive a file share request including a file share expiration date/time and share the file with a recipient, as indicated by the user computing device, until the file share expiration date/time is met and/or passed.

As described herein, "health information" can include information related to a patient's medical history such as diagnosis information (e.g., an ICD-10 diagnosis code), procedures (e.g. a HCPCS procedure code), medical claims (Mx) information, clinical information, electronic health record information, government health information (e.g., national health insurance (e.g., Medicare, Medicaid, national/universal health care) claims information), facility or health care system location information, and medical outcomes as well as (pharmacy-dispensed) prescription claims (Rx) information associated with one or more medical products (e.g., including transaction information, prescribing HCP national prescriber identifier (NPI), medical product information, date/time information, diagnosis information, and the like). Further, "health information" can further include protected health information (PHI) such as a patient's name, address, IP address, contact information, and the like and longitudinal health information. In this regard, "longitudinal health information" can include health information for a specific HCP or patient over a period of time. For example, "longitudinal health information" may include a group or set of Rx information for one patient over 10 years. In another example, "longitudinal health information" may include a group of Rx information for one HCP over a period of 10 years.

As described herein, "health care professional (HCP) information" can include information related to an HCP such as an NPI of the HCP, a name of the HCP, an address of the HCP, a specialty of the HCP (e.g., Cardiology), a place of employment of the HCP (e.g., Johns Hopkin's hospital, X Medical Group, an address including zip code and/country, etc.), HCP location information (e.g., an address including zip code and/or country, a location of the HCP's employer or primary health care organization (HCO), a country of residence or employment of the HCP, etc.) associated with the HCP, a type, degree, or certification held by the HCP (e.g., Doctor of Medicine, Registered Nurse, Nurse Practitioner, etc.), and other information described herein as being associated or related to an HCP.

Referring now to FIG. 1, a system 100 for analyzing longitudinal health information and generating a dynamically structured electronic file is shown, according to an example embodiment. The system 100 includes a provider computing system 104, a covered entity computing system 108, a user computing device 112, a recipient computing device (or system) 116, a consumer database 120, a health care professional (HCP) database 124, and one or more national health databases 125 connected by a secure network (e.g., a network 118).

The network 118 communicably and operably couples the provider computing system 104, the covered entity computing system 108, the user computing device 112, and the recipient computing device 116 such that communicable and operable computing may be provided between the provider computing system 104, the covered entity computing system 108, the user computing device 112, and the recipient computing device 116 over the network 118. In some embodiments, the network 118 further communicably and operably couples the consumer database 120, the HCP database 124, and the national health databases 125 to the provider computing system 104, the covered entity computing system 108, the user computing device 112, and the recipient computing device 116. In various embodiments, the network 118 includes any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to the user computing device 112 over the network 118 in response to authenticating the user computing device 112. As shown, the provider computing system 104 may include a network interface circuit 126, a processing circuit 128, an account database 132, a medical domain database 134, and a projection model database 135. In some embodiments, the provider computing system 104 may include an input/output circuit (e.g., similar to or the same as an input/output circuit 180 which will be described further herein).

The network interface circuit 126 is structured to establish connections with the covered entity computing system 108, the user computing device 112, the recipient computing device 116, the consumer database 120, and the HCP database 124 by way of the network 118. The network interface circuit 126 includes program logic and/or hardware-based components that connect the provider computing system 104 to the network 118. For example, the network interface circuit 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 126 includes the hardware and machine-readable media structured to support communication over multiple channels of data communication (e.g., wireless, Bluetooth, near-field communication (NFC). In some embodiments, the network interface circuit 126 includes cryptography logic and capabilities to establish a secure communications session.

The processing circuit 128, as shown, comprises a memory 136, a processor 140, a request generation and management circuit 144, an information matching and analytics circuit 148, a file generation circuit 150, and a file sharing circuit 152. The memory 136 includes one or more memory devices (e.g., RAM, NVRAM, ROM, flash memory, hard disk storage, etc.) that store data and/or computer code for facilitating the various processes described herein. That is, in operation and use, the memory 136 stores at least portions of instructions and data for execution by the processor 140 to control the processing circuit 128. The memory 136 may be or include tangible, non-transient volatile memory and/or non-volatile memory. The processor 140 may be implemented as a general-purpose processor, an application specific integrated circuit (ASIC), one or more field programmable gate array (FPGAs), a digital signal processor (DSP), a group of processing components or other suitable electronic processing components.

As described herein, the request generation and management circuit 144 is structured to generate and manage health information requests that may be provided to the covered entity computing system 108. For instance, the request generation and management circuit 144 may be structured to retrieve information included in the health information request (e.g., a timeframe for which health information is sought), government health information (e.g., from the national health databases 125), consumer information (e.g., from the consumer database 120) for which matching or associated health information is sought, HCP information (e.g., from the HCP database 124) for which matching or associated health information is sought, medical product information for which matching or associated health information is sought (e.g., from the medical domain database 134), or any combination thereof. Further, the request generation and management circuit 144 may be structured to generate the health information request including the information included in the health information request and provide the health information request to the covered entity computing system 108. In some embodiments, the request generation and management circuit 144 may be configured to generate and provide the health information request to the covered entity computing system 108 at specific time intervals (e.g., every hour, every day, every week, every month, etc.), and, as a result, the provider computing system 104 may receive the health information at the specific time intervals. By doing so, the provider computing system 104 may act as a centralized source of reliable, up to date, health information. For instance, because the request generation circuit 144 may generate and provide the health information request to the covered entity computing system 108 at specific time intervals, the provider computing system 104 may receive updated health information at the specific time intervals and have the most up to date health information.

As described herein, the health information request may include information for which matching health information is sought. In one example, the health information request may include a list of specific IP addresses that watched an online advertisement. The covered entity computing system 108 may receive the health information request, match (longitudinal) health information of patients having an IP address within the list and return the health information to the provider computing system 104. Prior to returning the matching health information, the covered entity computing system 108 may de-identify (e.g., hash, tokenize, encrypt, etc.) the PHI included in the health information. In this way, the PHI of the patient is protected, and the patient's privacy is maintained.

In some embodiments the request generation and management circuit 144 is further structured to manage and receive health care professional (HCP) file generation requests that may be received from the user computing device 112. For instance, the request generation and management circuit 144 may receive one or more HCP file generation requests (also referred to as electronic file generation requests) from the user computing device 112. The HCP file generation requests may each indicate one or more statistical values (e.g., median quantity of a medical product, likelihood or percentage of times switched from the medical product, percentage of generic medical products versus name brand medical products, etc.) associated with the HCP that are to be calculated as well as a file destination address to which the HCP file may be provided. In other embodiments, a separate request circuit or other circuits (e.g., the information matching and analytics circuit 148) described herein may manage and receive HCP file generation requests from the user computing device 112.

In some embodiments the request generation and management circuit 144 is further structured to manage a defined location prescribing file generation request (also referred to as an electronic file generation request) that may be received from the user computing device 112. For instance, the request generation and management circuit 144 may receive one or more defined location prescribing file generation request from the user computing device 112. The defined location prescribing file generation requests may each indicate one or more defined locations (e.g., one or more zip codes, one or more states, one or more countries) for which projected prescribing values are sought and statistical values (e.g., median quantity of a medical product, likelihood or percentage of times switched from the medical product, percentage of generic medical products versus name brand medical products, etc.) associated with the defined location that are to be calculated. Further, the defined location prescribing file generation request may include a file destination address to which the defined location prescribing file may be provided. In other embodiments, a separate request circuit or other circuits (e.g., the information matching and analytics circuit 148) described herein may manage defined location prescribing file generation requests.

The information matching and analytics circuit 148 is structured to receive the health information from the covered entity computing system 108 and/or government health information from the national health databases 125, match the health information and/or government health information with HCP information (e.g., the location information of the HCP information) from the HCP database 124, filter the matching health information and HCP information (e.g., as specified by the HCP file generation request), and determine one or more HCP statistical values or insights based on the matched and filtered health information and HCP information. For example, the provider computing system 104 may receive an HCP file generation request that requests health information associated with all HCPs who prescribed a patient drug X to be included in the HCP file. Moreover, the HCP file generation request may also request the provider computing system 104 to include the median quantity of drug X that each HCP prescribes. The information matching and analytics circuit 148 may match the health information with the prescriber information (e.g., based on the NPI of the HCP in both sets of information) and filter the matched health information for medical product drug X (i.e., remove all matched health information and HCP information that does not include medical product information of drug X). Further, the information matching and analytics circuit 148 may calculate the median quantity of drug X for each HCP who prescribed drug X using the filtered and matched health information. In this way, the information matching and analytics circuit 148 may generate statistical values or insights for each HCP based on the longitudinal health information matched with the HCP.

In another example, the provider computing system 104 may receive a defined location prescribing file generation request that requests health information associated with each zip code of a first state (e.g., Wisconsin) and drug X, for the past year, to be included in the defined location prescribing file. Moreover, the defined location prescribing file generation request may also request the provider computing system 104 to include the median quantity of drug X that was prescribed in each zip code of the state. The information matching and analytics circuit 148 may match the health information with the HCP information (e.g., based on the NPI of the HCP in both sets of information) and filter the matched health information for medical product drug X and the defined location (i.e., remove all matched health information and HCP information that does not include medical product information of drug X and location information that matches Wisconsin). Further, the information matching and analytics circuit 148 may calculate the median quantity of drug X for each HCP who prescribed drug X using the filtered and matched health information.

In some embodiments, the information matching and analytics circuit 148 is further structured to determine if the health information received from the covered entity computing system 108 includes duplicate information. Because the health information can be received from a variety of covered entity computing systems, duplicate information is common and needs to be accounted for to provide for accurate insights. As a result, the information matching and analytics circuit 148 may parse the received health information and remove (if exact duplicates) or combine (if partial duplicates) sets of duplicate health information. By doing so, the provider computing system 104 may act as a trusted health information repository and maintain information integrity.

In some embodiments, the information matching and analytics circuit 148 is structured to select one or more digital projection models from the projection model database 135 and determine one or more sets of digitally projected prescriber values based on the matched government health information, the matched HCP information (e.g., location information), and/or the matched health information. For instance, the information matching and analytics circuit 148 may select a first digital projection model from the digital projection model database 135 and determine a first set of digitally projected prescriber values based on the government health information and a second set of digitally projected prescriber values based on the government health information, the matched/combined health information, and the matched/combined location information. In some embodiments, a separate modeling circuit (e.g., not shown) may select the one or more digital projection models and determine the one or more sets of digitally projected prescriber values.

The file generation circuit 150 is structured to generate the HCP file based on the HCP file generation request received by the provider computing system 104. For instance, once the information matching analytics circuit 144 has matched the health information with the HCP information and generated any requested statistical values, the file generation circuit 150 may generate a file of a specified format (e.g., comma-separated value (CSV) format, Excel (XLS) format, etc.) and populate it with the matched health information, the matched HCP information, and the generated statical values. Because the HCP file is generated as a specified file format, the HCP file can be shared with a variety of destinations and quickly parsed and analyzed. In some embodiments, the HCP file generation request may indicate the specified file format that the HCP file is to be.

The file sharing circuit 152 is structured to share and manage the HCP file with computing devices, customers, and user's other than the user of the user computing device 112 (e.g., recipients). For instance, the file sharing circuit 152 may receive a file share request indicating a recipient address and a file share expiration date and/or time from the user computing device 112. In response, the file sharing circuit 152 may share the HCP file with the recipient address and/or allow the recipient address to access the HCP file until the expiration date and/or time is met. In this way, the user of the user computing device 112 may easily provide others access to the HCP file and share the HCP file for improved collaboration and analysis of the HCP insights.

The account database 132 is a repository that receives, stores, and manages various account information (e.g., login credentials, HCP files, recipient devices to share HCP files with, etc.). To do so, the account database 132 can be structured according to various database types, such as, relational, hierarchical, network, flat, point-in time, and/or object relational. In operation, the account database 132 is configured to store account information in association with a specific user or specific users. For instance, the account database 132 may store generated HCPs file in association with the user of the user computing device 112. In one embodiment, the account database 132 may store medical product groups (i.e., multiple associated medical products) associated with the account of the user. In other embodiments, the medical domain database 134, as described herein, may do so. In some embodiments, multiple databases may take the place of a single account database and store/manage one or more pieces of the information that the account database is described herein as storing/managing.

Likewise, the medical domain database 134 is a repository that receives, stores, and manages various medical domain information (e.g., medical product information, procedure information, diagnosis information (e.g., diagnosis codes and descriptions), and procedure information (e.g., procedure codes and descriptions) associated with the user or an HCP. To do so, the medical domain database 134 can be structured according to various database types, such as, relational, hierarchical, network, flat, point-in time, and/or object relational. In operation, the medical domain database 134 is configured to store medical domain information such as medical product information, diagnosis information, and procedure information. In one instance, the medical domain database 134 may receive a grouping of multiple drugs as specified by the user of the user computing device 112. As will be described herein, the grouping of drugs may be utilized by the user in generating HCP file generation requests and HCP files.

Similarly, the projection model database 135 is a repository that receives, stores, and manages various digital projection models (e.g., machine-learning (ML) models, statistical models, etc.) used to determine digitally projected prescription values. To do so, the projection model database 135 can be structured according to various database types, such as, relational, hierarchical, network, flat, point-in time, and/or object relational. In operation, the projection model database 135 is configured to store, manage, and provide digital projections models such as ML projection (i.e., forecasting) models (e.g., binary classification models, neural network models (e.g., Convolutional Neural Network (CNN) model, Long Short-Term Memory Networks (LSTMs) models) multiclass classification models, regression models (e.g., linear regression models), etc.).

In some embodiments, the provider computing system 104 may further include a digitally projected value database (not shown). The digitally projected value database may receive, store, and manage the generated digitally projected values described further here. The digitally projected value database can be structured according to various database types, such as, relational, hierarchical, network, flat, point-in time, and/or object relational. In operation, the digitally projected value database may receive digitally projected values and associated metadata. For instance, the digitally projected value database may receive a digitally projected value and metadata that indicates the digitally projected value is associated with a specific timeframe, a specific medial product, a specific prescription type, and/or a specific location. Then, the provider computing system 104 may select or query the digitally projected value database for digitally projected values based on the metadata.

Still referring to FIG. 1, the covered entity computing system 108 may include a computer system (e.g., one or more servers each with one or more processing circuits) and be operated by, be managed by, and/or operate on a data network of a "covered entity" as defined by the Health Insurance Portability and Accountability Act of 1996 (HIPAA) (or other laws that protect health information). For example, the covered entity may be a pharmacy chain (e.g., a pharmacy company) with access to prescription claims information, a medical claims company (e.g., a medical insurance company) with access to medical claims information, a medical provider with access to electronic health records, or a government entity with access to national health insurance (e.g., Medicare or Medicaid) claims information, and the like. In this regard, the covered entity computing system 108 may have direct access to health information including PHI, transaction information, and other health information associated with one or more patients. As shown, the covered entity computing system 108 may include a network interface circuit 156, a processing circuit 160, and a prescription and medical claims database 164. In some embodiments, the covered entity computing system 108 may include an input/output circuit (e.g., similar to the input/output circuit 180).

The network interface circuit 156 is structured to establish connections with the provider computing system 104, the user computing device 112, the recipient computing device 116, the consumer database 120, and the HCP database 124 by way of the network 118. The network interface circuit 156 includes program logic and/or hardware-based components that connect the covered entity computing system 108 to the network 118. For example, the network interface circuit 156 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 156 includes the hardware and machine-readable media structured to support communication over multiple channels of data communication (e.g., wireless, Bluetooth, near-field communication (NFC). In some embodiments, the network interface circuit 156 includes cryptography logic and capabilities to establish a secure communications session.

The processing circuit 160, as shown, comprises a memory 168, a processor 170, an information matching circuit 172, and a deidentification circuit 174. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate array (FPGAs), a digital signal processor (DSP), a group of processing components or other suitable electronic processing components.

The information matching circuit 172 is structured to receive the health information requests from the provider computing system 104 including any additional information for which matching health information is sought (e.g., consumer information, HCP information, etc.) and determine the matching health information. For instance, the information matching circuit 172 may receive a health information request including medical product information (e.g., a list of medical products) for which matching health information is sought. The information matching circuit 172 may then search or query the prescription and medical claims database 164 for health information that is associated with one or more of the medical products of the medical product information. For example, the information matching circuit 172 may search and return a piece of health information (e.g., an Rx transaction) which is associated with a medical product of the medical product information. In another example, the information matching circuit 172 may search and return health information matched with consumer information (e.g., demographic information).

The deidentification circuit 174 is structured to receive the matched health information and deidentify any PHI included within the matched health information and corresponding information (e.g., consumer information). To deidentify the PHI of the matched health information, the deidentification circuit 174 may first determine any PHI included in the matched health information and then perform one or more operations to remove the associated patient's identity or related private information. In some embodiments, the deidentification circuit 174 may deidentify PHI of the health information by encrypting the PHI, tokenizing the PHI, or by performing some other information masking function.

In other embodiments, the deidentification circuit 174 may deidentify PHI of the health information by performing a hash function on the PHI. For example, the deidentification circuit 174 may perform a hash function on the private health information that removes the identity or private information of the patient and returns a hash value in place of the PHI. Example hash functions include, but are not limited to, the mid-square method, string folding, and the like. In some embodiments, all covered entity computing systems from which health information is received by the provider computing system 104 (including the covered entity computing system 108) may use the same hash function to provide for consistent hash values across covered entity computing systems. For example, because each covered entity computing system may use the same hash function (i.e., a hash function that returns the same hash value for the same input), the provider computing system 104 may receive health information, with deidentified PHI, from multiple covered entity computing systems. For example, the provider computing system 104 may receive health information including Rx information from a pharmacy chain covered entity computing system, health information including Mx information from a medical claims company, health information including clinical information from a medical provider (e.g., a hospital), and health information including national health insurance claims information from a national health insurance provider, each piece of health information including deidentified PHI. Then, the provider computing system 104 may match the various pieces of received health information based on the deidentified PHI and specifically based on matching hash values. In other embodiments, the provider computing system 104 matches the various pieces of received health information by matching one or more patient demographics or attributes (e.g., same HCP NPI, same date of transaction, same credit card used in both transactions, etc.) to match the health information. In this way, information integrity and usability of the PHI may be maintained while protecting the patients PHI and identity.

Once the deidentification circuit 174 has deidentified the PHI of the health information, the processing circuit 160 and the network interface circuit 156 may be structured to send the health information, including the deidentified PHI, to the provider computing system 104, in response to the health information request. In some embodiments, the covered entity computing system 108 may receive health information requests at specific time intervals and provide the matched health information to the provider computing system 104 at the same time intervals. In this way, the provider computing system 104 may have the most up to date health information and act as a centralized source of reliable, up to date, health information.

The prescription and medical claims database 164 is a repository that receives, stores, and manages various Rx information and/or Mx information associated with the customers or users of the covered entity. To do so, the prescription and medical claims database 164 can be structured according to various database types, such as, relational, hierarchical, network, flat, point-in time, and/or object relational. In operation, the prescription and medical claims database 164 is configured to store Rx and/or Mx information. In some embodiments, the prescription and medical claims database 164 is a health information database 164 configured to store health information including PHI, Rx information, medical product information, Mx information, and the like. For example, if the covered entity is a medical claims company, the covered entity computing system may include a medical claims database to store medical claims information. In another example, the covered entity computing system 108 may include a national health insurance claims database (e.g., similar to or the same as the national health database 125) or an electronic health record database. In some embodiments, the prescription and medical claims database 164 is not included in the covered entity computing system 108 but is connected to the covered entity computing system 108 over a covered entity private network or the network 118.

In other embodiments, each covered entity computing system 108 may include multiple databases information databases for each piece of separately stored health information (i.e., a separate database for Rx information and for Mx information).

Still referring to FIG. 1, the user computing device 112 can be any type of computing device or system configured to run an application (e.g., a web-based application, a mobile application, etc.). For instance, the user computing device 112 can be one or more of a mobile phone, a tablet computer, a laptop computer, a smart watch, a server computer system, and any other internet-connected device that is capable of running an application. In operation, the user computing device 112 may download or connect to (e.g., via the network 118) the application of the provider computing system 104. Once downloaded or connected to the application of the provider computing system 104, the user computing device 112 may interface with the provider computing system 104 to receive the HCP file, to generate and provide an HCP file generation request, and to generate and provide an HCP file share request. As shown, the user computing device 112 includes a network interface circuit 176, a processing circuit 178, and the input/output (I/O) circuit 180.

The network interface circuit 176 is structured to establish connections with the provider computing system 104, the covered entity computing system 108, the recipient computing device 116, the consumer database 120, and the HCP database 124 by way of the network 118. The network interface circuit 176 may be similar to the network interface circuit 126 and include program logic and/or hardware-based components that connect the user computing device 112 to the network 118. For example, the network interface circuit 176 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 176 includes the hardware and machine-readable media structured to support communication over multiple channels of data communication (e.g., wireless, Bluetooth, near-field communication (NFC). In some embodiments, the network interface circuit 176 includes cryptography logic and capabilities to establish a secure communications session.

The processing circuit 178, as shown, may comprise a memory 182, a processor 184, and a user interface generation circuit 185. The memory 182 includes one or more memory devices (e.g., RAM, NVRAM, ROM, flash memory, hard disk storage, etc.) that store data and/or computer code for facilitating the various processes described herein. That is, in operation and use, the memory 182 stores at least portions of instructions and data for execution by the processor 184 to control the processing circuit 178. The memory 182 may be or include tangible, non-transient volatile memory and/or non-volatile memory. The processor 184 may be implemented as a general-purpose processor, an application specific integrated circuit (ASIC), one or more field programmable gate array (FPGAs), a digital signal processor (DSP), a group of processing components or other suitable electronic processing components.

The user interface generation circuit 185 may be configured to receive a user interface (e.g., a web interface in an HTML file and related files, a downloaded graphical user interface, etc.) from the provider computing system 104 and render or generate the user interface on the user computing device 112 via the I/O circuit 180. In this way, the provider computing system 104 may generate one or more user interfaces and provide the one or more user interfaces to the user interface generation circuit 185 to be rendered on the user computing device 112 (e.g., on a display of the I/O circuit 148 of the user device 112). Further functionality of the user interface generation circuit 185 as well as example user interfaces will be described further herein.

The I/O circuit 180 is structured to receive communications form and provide communications to the user of the user computing device 112 (e.g., the user). In this regard, the I/O circuit 180 is structured to exchange data with the processing circuit 178 to provide output to the user and to receive input from the user. As a result, the I/O circuit 180 may include a display that may be manipulated by the application. In some embodiments, the I/O circuit 180 may also include a keyboard, a mouse, a joystick, a touch screen, touch areas, soft keys, a microphone, a speaker, a vibration mechanism, a sensor, a RFID scanner, or other input/output devices described herein.

The recipient computing device 116 is structured to interface with the provider computing system 104 and/or the user computing device 112 by way of the network to receive an HCP file, in response to the user device 112 requesting the recipient computing device 116 receive access to the HPC file. In operation, the recipient computing device 116 may receive or request access to one or more HCP files and then receive or be provided with access to the HCP files. Therefore, the recipient computing device 116 can be one or more of a mobile phone, a tablet computer, a laptop computer, a smart watch, a server computer system, and any other internet-connected device. In this regard, the recipient computing device 116 may be a computing system associated with the recipient address described herein. For example, the recipient address may be an email of the recipient and the recipient computing device 116 may be multiple computing devices the recipient uses to access their email and therefore the HCP file (e.g., the recipient's smart phone and the recipient's laptop, and so on). Further, the recipient computing device 116 is shown to include a network interface circuit 186, a processing circuit 188, and the input/output (I/O) circuit 190.

The network interface circuit 186 is structured to establish connections with the provider computing system 104, the covered entity computing system 108, the user computing device 112, the consumer database 120, and the HCP database 124 by way of the network 118. The network interface circuit 186 may be similar to the network interface circuit 126 and include program logic and/or hardware-based components that connect the recipient computing device 116 to the network 118. For example, the network interface circuit 186 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 186 includes the hardware and machine-readable media structured to support communication over multiple channels of data communication (e.g., wireless, Bluetooth, near-field communication (NFC). In some embodiments, the network interface circuit 186 includes cryptography logic and capabilities to establish a secure communications session.

The processing circuit 188, as shown, may comprise a memory 192 and a processor 194. The memory 192 includes one or more memory devices (e.g., RAM, NVRAM, ROM, flash memory, hard disk storage, etc.) that store data and/or computer code for facilitating the various processes described herein. That is, in operation and use, the memory 192 stores at least portions of instructions and data for execution by the processor 194 to control the processing circuit 188. The memory 192 may be or include tangible, non-transient volatile memory and/or non-volatile memory. The processor 194 may be implemented as a general-purpose processor, an application specific integrated circuit (ASIC), one or more field programmable gate array (FPGAs), a digital signal processor (DSP), a group of processing components or other suitable electronic processing components.

The I/O circuit 180 is structured to receive communications form and provide communications to the user of the recipient computing device 116 (e.g., a recipient). In this regard, the I/O circuit 190 is structured to exchange data with the processing circuit 188 to provide output to the recipient and to receive input from the recipient. In some embodiments, the I/O circuit 180 may include a display, a keyboard, a mouse, a joystick, a touch screen, touch areas, soft keys, a microphone, a speaker, a vibration mechanism, a sensor, a RFID scanner, or other input/output mechanisms.

Still referring to FIG. 1, the consumer database 120 is a repository that receives, stores, and manages various consumer information associated with multiple consumers. To do so, the medical consumer database 120 can be structured according to various database types, such as, relational, hierarchical, network, flat, point-in time, and/or object relational. In operation, the consumer database is configured to store consumer information such as IP addresses of consumers who watched a video, IP addresses of consumers who visited a specific webpage, names of consumers who live within a specific state, consumer demographic information (e.g., income information, gender information, ethnicity information), and the like. Further, the consumer information within the consumer database may be used to generate health information requests by the provider computing system 104. In this regard, the provider computing system 104 may generate lists of consumers for which health information is sought, populate the health information request with the list, and provide the health information request to the covered entity computing system 108, which may return deidentified health information of corresponding consumers. In some embodiments, the consumer database 120 is operated by a third-party and communicates with the provider computing system 104, the covered entity computing system 108, and/or the user computing device 112 over the network 118. For example, the provider computing system 104 may send a consumer information request to the consumer database 120 including a list of consumers or HCPs for which consumer information is sought. In response, the consumer database 120 may provide consumer information associated with the HCPs to the provider computing system 104. In other embodiments, the provider computing system 104, the covered entity computing system 108, or the user computing device 112 include the consumer database 120.

Likewise, the HCP database 124 is a repository that receives, stores, and manages various HCP information associated with multiple HCPs. To do so, the HCP database 124 can be structured according to various database types, such as, relational, hierarchical, network, flat, point-in time, and/or object relational. In operation, the HCP database 124 is configured to store HCP information such as HCP address or other HCP location information (e.g., address of the HCP's employer, zip code of the HCP or the HCP's employer, etc.), HCP national provider identifier (NPI), Veeva HCP Identifier (VID), HCP specialties, HCP type (e.g., Nurse Practitioner, Doctor of Medicine, etc.), and the like. Further, the HCP database 124 may provide HCP information to the provider computing system 104 to be included in health information requests or to be matched with health information. For instance, the provider computing system 104 may receive the health information (e.g., Rx information including the name of the prescribing physician) from the covered entity computing system 108 and match it with the HCP information (e.g., the name of the HCP, the HCP NPI, the HCP specialty, etc.). The matched information may then be included in a generated HCP file. In some embodiments, the HCP database 124 is operated by a third-party and communicates with the provider computing system 104, the covered entity computing system 108, and/or the user computing device 112 over the network 118. In other embodiments, the provider computing system 104, the covered entity computing system 108, or the user computing device 112 include the HCP database 124.

Similarly, the one or more national health databases 125 are each a repository that receives, stores, and manages various government health information (e.g., national health insurance (e.g., Medicare, Medicaid) claims information (e.g., Mx and/or Rx claims information), universal health care (e.g., MediFund of Singapore, etc.) or coverage claims information (e.g., Mx and/or Rx), and the like. Further, the government health information may include location information (e.g., zip code, country, city, state), medical product information, national health care statistics (e.g., Rx is from Medicare part A, Medicare part B, Medicare part C, Medicare part D, etc.), HCP information (e.g., NPI of the HCP who prescribed a specific Mx or Rx,), deidentified PHI, and the like.

Additionally, the national health database 125 can be structured according to various database types, such as, relational, hierarchical, network, flat, point-in time, and/or object relational. In operation, the national health database 125 is configured to store, manage, and provide government health information such as national health insurance Rx claims information, national health insurance Mx claims information, and the like. In some embodiments, the one or more national health databases 125 are each operated by a computing system associated with a government healthcare agency (e.g., the Center for Medicare & Medicaid Services (CMS)). In this regard, the government health information may include a first portion associated with Rx claims information and a second portion associated with Mx claims information. In other embodiments, the national health databases 125 are each a part of the covered entity computing systems 108. Further, the government health information may include location information (e.g., zip code, country, city, state), medical product information, national health care statistics (e.g., Rx is from Medicare part A, Medicare part B, Medicare part C, Medicare part D, etc.), HCP information (e.g., NPI of the HCP who prescribed a specific Mx or Rx,), deidentified PHI, and the like.

Figure 2A:
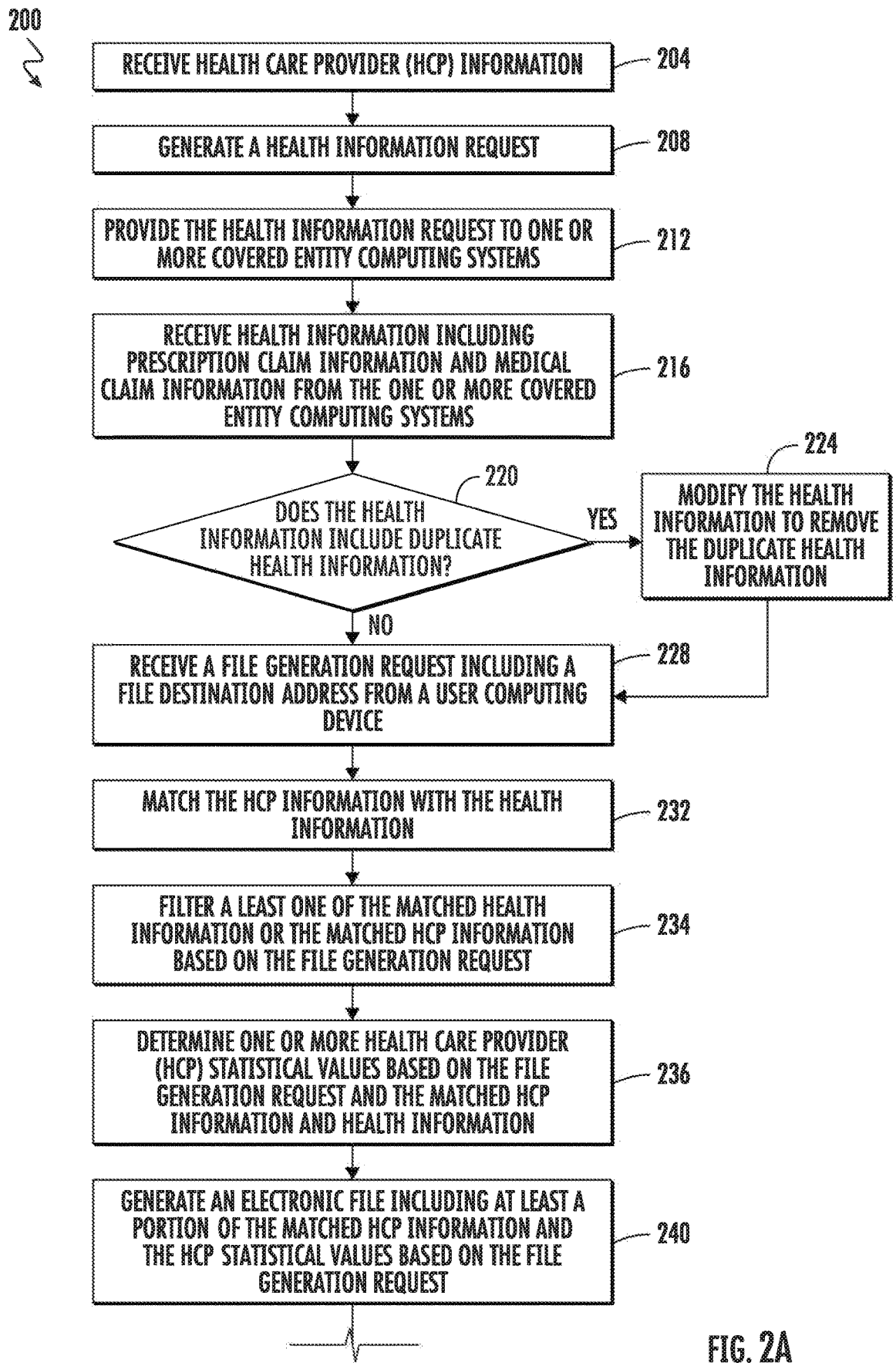
FIGS. 2A and 2B are a flow diagram of a method for analyzing longitudinal health information and generating and sharing a dynamically structured electronic HCP file, according to an example embodiment.
Figure 2B:
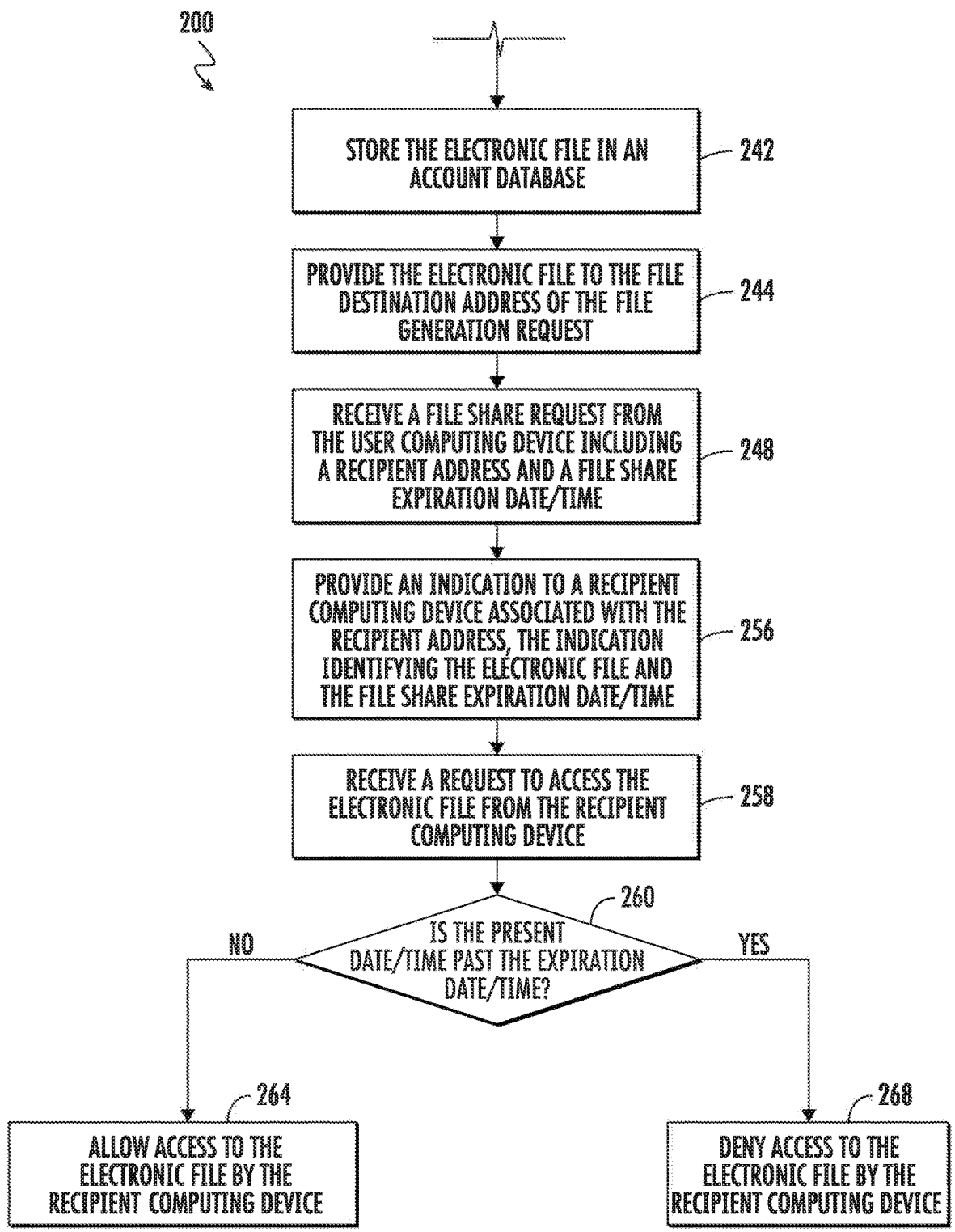

Referring now to FIGS. 2A-2B, a method 200 of analyzing longitudinal health information and generating a dynamically structured HCP file (also referred to as a dynamically structured electronic file) is shown, according to an example embodiment. Method 200 can be carried out by the system of FIG. 1. More particularly, the method 200 can be carried out by the processing circuit 128 of the provider computing system 104 and through communication with the covered entity computing system 108, the user computing device 112, and the recipient computing device 116.

Method 200 commences at step 204 at which the provider computing system 104 receives HCP information from the HCP database 124. The HCP information may be used to populate a health information request and may be received along with other information. For example, at step 204, the provider computing system 104 may receive other information used to populate the health information request such as consumer information (from the consumer database 120), timeframe information, medical product information (from the medical product database), and other information described herein as being included in the health information request. In some embodiments, the provider computing system 104 receives HCP information (or the other information with which the health information request is populated) from the HCP database 124 at specific time intervals (e.g., the same as or different than the specific intervals at which the health information requests are generated). In further embodiments, the provider computing system 104 may receive information used to populate the health information request (e.g., consumer information) at step 204 and receive the HCP information at or after another step in the method 200 (e.g., prior to or after step 228 as will be discussed further herein).

Once the provider computing system 104 has received the HCP information, the method 200 proceeds to step 208 at which the provider computing system 104 generates a health information request. As described herein, the health information request may be generated and populated to include the information received at step 204 such as the HCP information, the consumer information, the medical product information, and the timeframe information. The health information request 208 may request health information that is associated with or matches the information included in the health information request. In some embodiments, the health information request 208 may request health information that is not associated with or does not match the information included in the health information request.

In some embodiments, at step 208, the provider computing system 104 may generate multiple health information requests at step 208. For example, the provider computing system 104 may generate a health information request for each covered entity computing system from which health information is sought. In other embodiments, the provider computing system 104 may generate a single, reused, health information request that is sent to each covered entity computing from which health information is sought.

Additionally, at step 208, the provider computing system 104 may generate the health information request, at a specific time interval or rate (e.g., once a day, once a week, once a month, every 5 minutes, etc.). In some embodiments, the specific time interval or rate at which the health information request is generated is different than the specific time interval or rate at which the HCP information, medical product information, and/or consumer information is received. In other embodiments, the specific time interval or rate at which the health information request is generated is the same as the specific time interval or rate at which the HCP information, medical product information, and/or consumer information is received. By doing so, the provider computing system 104 may generate an updated health information request including the most recently received HCP, medical product, and/or consumer information.

Once the provider computing system 104 has generated the health information request, the method 200 proceeds to step 212 at which the provider computing system 104 provides the health information request to one or more covered entity computing systems (e.g., the covered entity computing system 108). In some embodiments, the provider computing system 104 may provide the health information request over the network 118 via the network interface circuit 126 to the one or more covered entity computing systems 108.

Once the provider computing system 104 has provided the health information request to the one or more covered entity computing systems, the method 200 proceeds to step 216 at which health information is received from the one or more covered entity computing systems 108. The health information may be received in response to the provider computing system 104 providing the health information request to the one or more covered entity computing systems and may be or include Rx information, Mx information, medical product information, transaction information, diagnosis information, and other health information described herein. For example, the health information may be prescription claims (Rx) information that includes deidentified PHI, medical product information, diagnosis information (e.g., a diagnosis code), HCP information (e.g., an NPI of a prescribing HCP), date/time information, facility or health care system location information, and transaction information. In another example, the health information may be medical claims (Mx) information that includes deidentified PHI, medical product information, diagnosis information (e.g., a diagnosis code), HCP information (e.g., an NPI of a prescribing HCP), date/time information, facility or health care system location information, and transaction information. In another example, the health information may be national health insurance claims information or electronic health record information including deidentified PHI, medical product information, diagnosis information (e.g., a diagnosis code), HCP information (e.g., an NPI of a prescribing HCP), date/time information, facility or health care system location information, and transaction information. Further, the received health information may correspond to or be associated with the HCP information, the consumer information, and/or the medical product information included in the health information request. For example, the health information received at step 216 may be matched with or include consumer information for each individual consumer of each prescription. For example, each piece of Rx information may be matched with demographic information associated with the consumer of the prescription. Further, the received health information may include deidentified PHI, transaction information, date/time information, and medical product information.

In some embodiments, consumer information is received from the consumer database 120 at or after step 216 and matched with the HCP information. For example, the provider computing system 104 may receive consumer information from the consumer database 120 and match the consumer information with HCPs. In this regard, the consumer information may be organized by HCP such that HCP insights or statistical values described herein may be determined from the consumer information.

As described herein, the PHI may be deidentified, by the one or more covered entity computing systems 108, in a variety of ways including through encryption, tokenization, and using a hash function. In all cases, the one or more covered entity computing systems (e.g., the covered entity computing system 108) may use a consistent form of deidentification such that the same PHI input will return the same hash value or token. For example, if a piece of health information included the name "John Smith," a resulting deidentified hash value may be "1234321." To be consistent, each of the one or more covered entity computing systems, when identifying the name "John Smith," may then return the hash value "123431." By using the same hash function across the one or more covered entity computing systems, the provider computing system 104 can make additional connections between the received health information and generate HCP insights and statistical values. Further, less processing power is required by the provider computing system 104 as most of the health information matching is completed by the one or more covered entity computing systems prior to the health information being received by the provider computing system 104.

Once the provider computing system 104 has received the health information from the one or more covered entity computing systems 108, the method 200 proceeds to step 220 at which the provider computing system 104 determines if the received health information includes duplicate health information. To determine if the health information includes duplicate health information, the provider computing system 104 may parse each piece of the health information and determine if multiple pieces have one or more matching or at least partially matching information points. For example, the provider computing system 104 may determine that two pieces of health information have the same deidentified name hash value (e.g., "1234321"), the same date/time information, and/or the same medical product information. Then, based on these three matching information points, the provider computing system 104 may determine that the two pieces of health information are duplicates. In some embodiments, the provider computing system 104 may determine that multiple pieces of health information are duplicates if the date/time information, the deidentified PHI, and the medical product information of each piece of health information is the same.

Additionally, the provider computing system 104 may determine that multiple pieces of health information are substantially duplicates if each piece of health information includes one or more matching information points, but one of the pieces of health information includes more or different information points from the other pieces of health information. For example, the provider computing system 104 may determine that two pieces of health information have the same deidentified name hash value (e.g., "1234321"), the same date/time information, and the same medical product information, but that only one of the pieces of health information includes diagnosis information. Then, based on these three matching information points and the one additional information point (the diagnosis information), the provider computing system 104 may determine that the two pieces of health information are substantially duplicates.

If, at step 220, the provider computing system 104 determines that the received health information includes duplicate health information (or substantially duplicate health information), the method 200 proceeds to step 224 at which the provider computing system 104 modifies the received health information to remove the (substantially) duplicate health information. If the received health information includes multiple pieces of duplicate health information, the provider computing system 104 may modify the health information to remove or delete each excess piece of duplicate health information leaving only a single copy or piece of the duplicate health information. Alternatively, if the received health information includes multiple pieces of substantially duplicate health information, the provider computing system 104 may modify the health information to combine each piece of substantially duplicate health information leaving only a single, combined, piece of the substantially duplicate health information including all the information points of each piece of the substantially duplicate health information.

If, at step 220, the provider computing system 104 determines the received health information does not include (substantially) duplicate health information, or after the provider computing system modifies the health information at step 224, the method 200 proceeds to step 228. At step 228, the provider computing system 104 receives an HCP file generation request (also referred to as an electronic file generation request) from the user computing device 112. As described herein, the HCP file generation request may indicate one or more insights or statistical values (e.g., median quantity dispensed of a medical product, the number of times switched from or switched to prescribing or administering the medical product, percentage of generic medical products prescribed or administered versus name brand medical products, etc.) associated with the HCP that are to be calculated as well as include a file destination address to which the HCP file is to be provided. In some embodiments, the HCP file generation request may also identify or include a specified file format that the HCP file is to be. For example, the HCP file generation request may indicate the HCP file is to be generated as a .CSV file delimited with commas.

In some embodiments, the HCP file generation request may also identify the HCP and health information to be used in generating the HCP file. For example, the HCP file generation request may indicate a specific medical product (e.g., drug X) or medical product group for which health information is to be included and used in generating the HCP file.

In some embodiments, the HCP file generation request may include or indicate a specific time interval or rate at which an HCP file is to be generated. For example, the HCP file generation request may indicate that an HCP file is to be generated, based on specific health information and HCP information every month. The provider computing system 104 may then repeat the method 200 from steps 238-268 based on the HCP file generation request. In other embodiments, the provider computing system 104 may receive an HCP file generation request at the specific time interval or rate and perform steps 238-268 based on the received HCP file generation request. Additionally, the provider computing system 104 may generate a health information request (e.g., at step 208) at a first specific time interval or rate and may receive or generate an HCP file generation request at a second specific time interval or rate, that is different from the first specific time interval or rate. Because the health data may be received at a different time interval than the HCP file generation request, the provider computing system 104 may act as a source of centralized health information. For example, the provider computing system 104 may receive health information at a time interval faster than that of the HCP file generation request and continually be generating HCP files with new, updated health information.

Once the provider computing system 104 has received the HCP file generation request from the user computing device 112, the method 200 proceeds to step 232 at which the provider computing system 104 matches each piece of the HCP information with one or more pieces of the health information based on the HCP file generation request. The provider computing system 104 may match the HCP information with the health information by determining that one or more information of the HCP information match that of the health information. For example, the provider computing system 104 may determine that the health information includes a national provider identifier (NPI) of a prescribing physician. The provider computing system 104 may then match the NPI of the prescribing physician with the NPI of the HCP information. In this regard, the health information may be sorted based on each HCP. In some embodiments, the NPI may be a hashed or tokenized NPI such that the health information may be sorted based on each NPI of each HCP. In other embodiments, the provider computing system 104 may match one or more of a HCP name, an HCP address, an HCP specialty, or an Rx number of the health information with that of the HCP information.

In some embodiments, step 232 and the provider computing system 104 matching the HCP information with the health information may happen prior to receiving the HCP file generation request. For example, the provider computing system 104 may match the health information with the HCP information directly after step 220 and/or step 224 at which the duplicate information is removed from the health information. In another example, the provider computing system 104 may match the health information with the HCP information directly after step 216 in which the health information is received from the covered entity computing system 108 and the duplicate information may then be removed from the matched health information.

Once the provider computing system 104 has matched the HCP information with the health information, the method 200 proceeds to step 234 at which the provider computing system 104 filters at least one of the matched health information or the matched HCP information based on the HCP file generation request. For example and as discussed herein, the HCP file generation request may indicate a specific medical product group (e.g., drugs X, Y, and Z) for which health information is to be included and used in generating the HCP file. As a result and at step 234, the provider computing system 104 may filter, process, or refine the health information to remove the health information including medical product information that is not within the specific medical product group (e.g., drugs that are not X, Y, or Z or drugs that are not Brand X, Brand Y, or Brand Z) and resulting in health information that only includes medical product information that is within the specific medical product group. In another example, the HCP file generation request may indicate a specific specialty of HCP (e.g., cardiology) for which HCP information is to be included in generating the HCP file. Then, at step 232, the provider computing system 104 may filter, process, or refine the HCP information to remove the HCP information including specialty information that are not cardiology and resulting in HCP information that only includes specialty information that is cardiology. If matching health information is removed during the filtering process, the matched HCP information may be removed as well, assuming there is no remaining health information matched with the HCP information. In contrast, if matching health information is removed during the filtering process and there is remaining health information matched with the HCP information, the HCP information may not be removed. Further, if matching HCP information is removed during the filtering process, the matched health information may be removed as well, assuming there is no remaining HCP information matched with the health information.

In some embodiments, the order of steps 232 and 234 is reversed such that the provider computing system 104 filters and then matches the HCP information and the health information. In other embodiments, steps 232 and 234 may occur at the same time such that the provider computing system 104 filters and matches the HCP information and the health information at the same time (i.e., filtering may be done by matching the medical product information of the health information with that of the medical product group and likewise for diagnosis information and diagnoses groups). In this regard, it should be understood that the steps 232 and 234 are interchangeable and may occur in any order or at the same time.

Once the provider computing system 104 has filtered the matched HCP information and health information, the method 200 proceeds to step 236 at which the provider computing system 104 determines one or more HCP statistical values (e.g., insights). The HCP statistical values may be calculated or determined using the matched (and/or filtered) health information (e.g., Rx or Mx information), the matched (and/or filtered) HCP information, and, in some embodiments, the associated consumer information from step 204. Possible HCP statistical values will be discussed further herein but may include: a number of total prescriptions for a medical product for each HCP, the number of new prescriptions (i.e., the first time a patient has received a prescription of a specific medical product) for each HCP, the number of new-to-brand prescriptions (i.e., the first time a patient has received a prescription of a specific brand of a medical product) for each HCP, the number of total diagnoses of a medical condition for each HCP, the number of total patients each HCP has seen, the total number of medical claims processing for each HCP, the total number of prescriptions filled and medical claims processed for each HCP, the number of new to brand medical claims, the number of new to brand medical and prescription claims, the number of total patients on Medicare part B, part A, part C, and other national health care demographics (e.g., number of patients on Medicare, number of patients on Medicaid, etc.), patient demographics (e.g., % per specific age range, % per gender, % per income range, % per payment type) for each HCP, median quantity of medical product dispensed for each HCP, median days supply of each medical product dispensed for each HCP, number of times switching from a medical product for each HCP, number of times switching to a medical product for each HCP, and average time between switching to/from a medical product for each HCP.

For example, the HCP file generation request may indicate that the HCP file is to include patient demographics for each individual HCP, the median quantity of drug X that is dispensed by each HCP, and the number of times each HCP has switched from the drug X to drug Y. As a result and at step 236, the provider computing system 104 may determine patient demographics for each individual HCP based on the matched HCP information, the matched health information, and/or the received consumer information. For instance, the provider computing system 104 may parse the matched health information for each HCP and sum up the payment types (e.g., credit card, check, cash, Medicare payment, Medicaid payment, Commercial insurance payment, etc.) within the transaction information and then divide the summed number of each payment type by the total number of payments resulting in a % per payment type. The provider computing system 104 may further parse the matched health information for Rx information for drug X and determine the quantity of drug X dispensed in each prescription. Then, the provider computing system 104 may calculate the median quantity based on the quantity of drug X in each transaction. Lastly, the provider computing system 104 may parse the matched health information and search for a switch from drug X to drug Y. To determine a switch, the provider computing system 104 may determine a patient for an HCP was prescribed drug X by the HCP at a first point in time and then was prescribed drug Y by the HCP at a second point in time, after the first point in time. In some embodiments, the switch is only determined/counted if the patient is not prescribed drug X at or after the second point in time. The provider computing system 104 may then determine the total number of switches from drug X to drug Y for each HCP.

In another example, the HCP generation request may indicate that the HCP file is to include an adoption profile for the HCP for a specific medical product or group of medical products. The adoption profile may indicate the number of times the HCP switched to or from prescribing or administering the specific medical product and the drugs that the HCP switched to or from. Switching from a medical product indicates that the HCP previously prescribed a specific drug (e.g., drug X) for a given condition but has now begun prescribing another drug (e.g., drug Z), for the same condition. For example, the adoption profile for the HCP may indicate that 30% of the time the HCP switched from prescribing or administering drug X. Switching to a medical product indicates that the HCP previously prescribed a specific drug (e.g., drug J) for a given condition but has now begun prescribing another drug (e.g., drug K) for the same condition. For example, the adoption profile for the HCP may indicate that 30% of the time the HCP switched to prescribing or administering drug K. In other embodiments, the adoption profile may indicate a number of switches for each drug as compared to a percentage. To determine, the adoption profile for a specific medical product and HCP, the provider computing system 104 may determine each drug from which the HCP switched to or from the specific drug as well as the number of switches for each drug. Then, the provider computing system 104 may add up the total number of switches to or from the specific medical product, and divide each value by the total to get a percentage.

Once the provider computing system 104 has determined the one or more HCP statistical values or insights, the method 200 proceeds to step 240 at which the provider computing system 104 generates an HCP file including (e.g., populated with) at least a portion of the matched HCP information, at least a portion of the matched health information, and/or the HCP statistical values. The HCP file may be populated with at least a portion of the matched HCP information and the matched health information in that the HCP file may include some of the matched HCP information and the matched health information and omit other portions of the HCP information and the matched health information. For example, the HCP file may specifically omit any deidentified PHI of the matched health information. In some embodiments, the HCP file is populated with at least a portion of the matched HCP information and the HCP statistical values, but not the matched health information (as it is represented by the HCP statistical values).

Additionally and as described herein, the provider computing system 104 may structure the HCP file based on the HCP file generation request, the destination address of the HCP file generation request, and the specific file type of the HCP file generation request. For example, the provider computing system 104 may populate the HCP file with the generated HCP statistical values and the matched HCP information in a specific order based on the HCP file generation request and the recipient address of the HCP file generation request. For instance, if the HCP file is to be provided to the user computing device 112 (e.g., the destination address is the IP address of the user computing device 112), the provider computing system 104 may structure the HCP file to include a specific header for each HCP statistical value and for each piece of matched HCP information as well to include a single row for each HCP. In comparison, if the HCP file is to be provided to another portion of the provider computing system 104 (e.g., Veeva Nitro), the provider computing system 104 may structure the HCP file to include a specific row for each HCP statistical value and multiple rows for each HCP.

The HCP file may be generated as a specific file type as decided by the user in the HCP file generation request. For example, the HCP file may be generated as a CSV file, an Excel File (XLSX file), an XML file, a JSON file, and the like. By allowing the user to decide the specific file type of the HCP file in the HCP file generation request and not only generating the HCP file as one specific file type, the provider computing system 104 may provide for improved shareability of the HCP file as well as use less processing power and memory. For example, in situations where the HCP file is only generated as a specific, non-dynamic, file type, third-party computing systems and recipient computing devices (e.g., the recipient computing device 116) may have to perform additional file modification and conversion or request the provider computing system 104 to do so, which requires additional processing power, memory (to keep two files), and time. In comparison, the system 100 and the provider computing system 104 allow the user to specify the file type of the HCP file through the HCP file generation request. Accordingly, the user can specify the wanted file type the first time and the provider computing system 104 will generate the HCP as the specified file type. As a result, no additional file modification or conversion is required reducing processing power usage, memory usage, and overall processing time for the provider computing system 104.

Once the provider computing system 104 has generated the HCP file, the method 200 proceeds to step 242 at which the HCP file is stored in the account database 132. The provider computing system 104 may store the HCP file in the account database 132 in association with the user's account. In some embodiments, the provider computing system 104 may further retrieve the HCP file from the account database 132 and provide the HCP file to the user computing device 112 in response to the user requesting access to the HCP file. In some embodiments, the user and the user computing device 112 must first provide login credentials (e.g., a username and a password) and be authenticated before the provider computing system 104 will provide the HCP file to the user computing device 112.

Once the provider computing system 104 has stored the HCP file in the account database 132, the method 200 proceeds to step 244 at which the HCP file is provided to the file destination address of the HCP file generation request. The file destination address may be any type of address or destination (e.g., IP address, web address, email address, file transfer protocol (FTP) address, and the like) to which the HCP file may be electronically transmitted or provided. In one example, the file destination address may be another server or circuit of the provider computing system 104 that is configured to receive the HCP file (e.g., Veeva Nitro®). In another example, the file destination address may be a web address of the Amazon Simple Storage Service® cloud storage web service, a web address of Snowflake, a web address of Microsoft Azure, etc. In another example, the file destination address may be the IP address of the user computing device 112 and the HCP file may be provided to the user computing device 112.

Once the provider computing system 104 has provided the HCP file to the file destination address, the method 200 proceeds to step 246 at which the provider computing system 104 receives a file share request from the user computing device 112. The file share request may identify the HCP file (e.g., of a multiple of HCP files) and indicate that the user (of the user computing device 112) would like to share the HCP file with one or more recipients (e.g., of the recipient computing device 116) up until a specified point in time. As a result, the file share request may include a recipient address and a file share expiration date and/or time. The recipient address may be any address or destination (e.g., IP address, web address, email address, file transfer protocol (FTP) address, and the like) to which the HCP file may be electronically transmitted, provided, and/or accessed by up until a specific point in time (e.g., at or after the file share expiration date and/or time). In one example, the recipient address may be the IP address of the recipient computing device 116 and the HCP file may be transmitted to the recipient of the recipient computing device 116. In another example, the recipient address may be the email address of the recipient of the recipient computing device 116.

The file share expiration date and/or time is a specific date and/or time or time interval that defines a specific date and time at which the HCP file is no longer to be shared with the recipient address. For example, the file share expiration date and/or time may indicate the HCP file is no longer to be shared with the recipient address on Dec. 7, 2021 at 2:00 PM. Then, prior to Dec. 7, 2021 at 2:00 PM, the provider computing system 104 may share (e.g., provide, electronically transmit in response to a request, provide access via a web server, etc.) the HCP file with the recipient address. However, after Dec. 7, 2021 at 2:00 PM, the provider computing system 104 may not share (e.g., provide, electronically transmit in response to a request, provide access via a web server, etc.) or even deny access (e.g., display a message indicating as such and/or telling the recipient to contact the user of the user computing device) to the HCP file by the recipient address. In another example, the file share expiration date and/or time may indicate the HCP file is no longer to be shared with the recipient address on Dec. 7, 2021 and not specify a time. As a result, the recipient address may not have access to the HCP file on Dec. 7, 2021 at 12:00 AM. In some embodiments, the provider computing system 104 may specify the expiration date and/or time as being in the same time zone as the user (e.g., the user computing device 112).

Once the provider computing system 104 has received the file share request from the user computing device 112, the method 200 proceeds to step 256 at which the provider computing system 104 provides an indication to a recipient computing device (e.g., the recipient computing device 112) associated with the recipient address. The indication may identify the HCP file (e.g., the name of the HCP file, the location of the HCP file, and the like) as well as the file share expiration date/time. The indication may be used to simply provide the recipient notice that they now have access to the HCP file. In some embodiments, the indication may further include a Uniform Resource Locator (URL) or web address that the recipient may select (e.g., via a user interface on the recipient computing device 116) to be navigated to a web application in which the recipient may have access (i.e., download, view, access) the HCP file and which may be provided to the recipient computing device 116 in response to authenticating the recipient address as well as confirming the file share expiration date and/or time is not met/passed. In one example, the indication may be an email that is provided to a recipient email address and includes an HCP file URL. The HCP file URL may further include an expiration parameter (e.g., signature) that is associated with the file share expiration date and/or time. For example, the expiration parameter may be included in the URL and deactivate the URL after the file share expiration date and/or time. As a result, if the recipient selects the URL including the expiration parameter after the file share expiration date and/or time, the URL may be deactivated and not route the recipient to the web application or the HCP file.

Once the provider computing system 104 provides the indication to the recipient computing device 116, the method 200 proceeds to step 258 at which the provider computing system receives a request to access the HCP file from the recipient computing device 116. The request to access the HCP file may identify the HCP file as well as the recipient address through which the recipient computing device 116 is requesting access. For example, the request may be received and generated in response to the recipient of the recipient computing device selecting the HCP file URL of the indication. In some embodiments, the request to access the HCP file is receive after authenticating the recipient address of the recipient computing device 116 (e.g., after determining that recipient address is authorized to access the HCP file).

Once the provider computing system 104 receives the request to access the HCP file, the method 200 proceeds to step 260 at which the provider computing system 104 determines if the present date/time is past the file share expiration date/time. If, at step 260, the provider computing system 104 determines that the present date/time is not past the file share expiration date/time, the method 200 proceeds to step 264 at which the provider computing system 104 allows access to the HCP file by the recipient computing device 116. As described herein, the provider computing system 104 may allow access to the HCP file by the recipient computing device 116 in multiple ways. For example, the provider computing system 104 may provide or electronically transmit the HCP file to the recipient computing device 116. In another example, the provider computing system 104 may provide a web application and a web interface to the recipient computing device 116 through which the recipient may view and/or download the HCP file. In comparison, if at step 260, the provider computing system 104 determines that the present date/time is past the file share expiration date/time, the method 200 proceeds to step 268 at which the provider computing system 104 denies access to the HCP file by the recipient computing device 116. The provider computing system 104 may allow deny to the HCP file by the recipient computing device 116 in multiple ways. For example, the provider computing system 104 may provide or electronically transmit a notification to the recipient computing device 116 indicating that the recipient is not authorized to access the HCP file. In another example, the provider computing system 104 may further notify the user of the user computing device 112 that the recipient is attempting to access the HCP file and inquire if the file share expiration date/time should be extended.

Referring now to FIGS. 3-7, user interfaces shown to the user of the user computing device 112 during the method 200 and/or the method 900 are shown, according to example embodiments. As described herein, the user interfaces of FIGS. 3-7 may be one or more of web interfaces generated by the provider computing system 104 and rendered by the user computing device 112 as part of a web application or graphical user interfaces downloaded and generated by the user computing device 112 as part of a software application (e.g., mobile application, etc.). Further, the user interfaces shown on FIGS. 3-7 allow for communication between the user and the provider computing system 104 via the user computing device 112 (specifically via the I/O circuit 180). Through interaction with the various user interfaces, the user may provide user input, feedback, and other information requested by the provider computing system 104.

Figure 3:
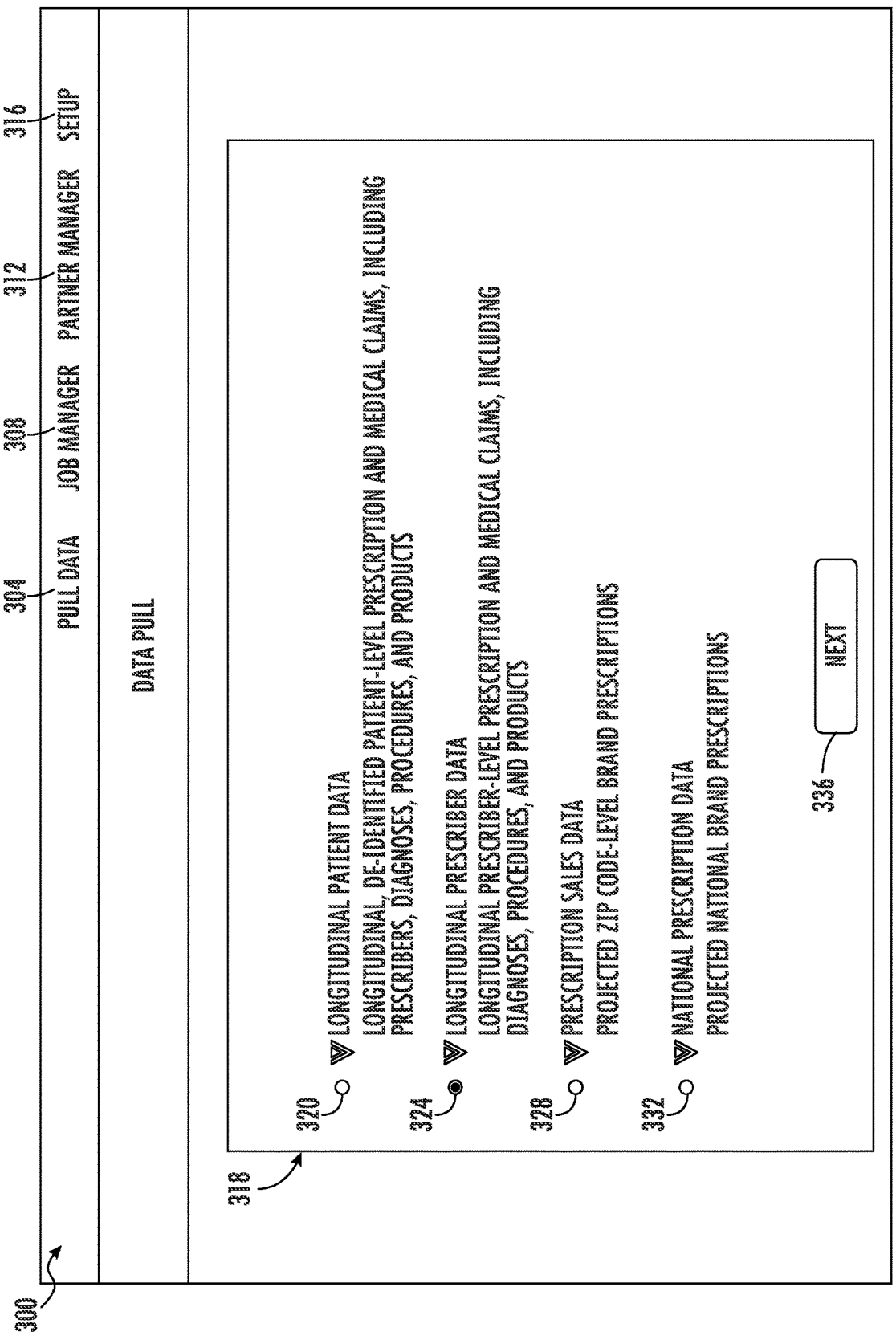
FIG. 3 is an illustration of some aspects of a user interface generated by the longitudinal health information analyzation and dynamically structured electronic file generation system of FIG. 1 to determine HCP information is sought, according to an example embodiment.

Referring now to FIG. 3, an information selection page 300, which can be displayed on a display of the I/O circuit 180 of the user computing device 112, is shown. In general, the information selection page 300 provides the user with multiple information types that can be analyzed and used to generate an HCP file generation request and therefore an HCP file. For example, through the information selection page, the user can decide between analyzing patient specific information, HCP specific information, prescription sales information, and national prescription information.

As shown, the information selection page 300 is shown to include a pull data button 304, a job manager button 308, a partner manager button 312, and a setup button 316. The pull data button 304 is a selectable (e.g., clickable, pressable) button that, when selected, generates and navigates the user to the information selection page 300 to select the information they would like to use and the type of file they would like to generate. In some embodiments, the data pull button 304, when selected, navigates the user to a web page that displays the information selection page 300. The job manager button 308 and the partner manager button 312 are each also selectable buttons that, when selected, navigate the user to other pages that will be described further herein. Similarly, the setup button 316 is a selectable button that, when pressed by the user, navigates the user to a setup/preferences page (not shown). The setup/preferences page provides the user with information associated with account preferences such as login information and medical device information.

Still referring to FIG. 3, the information selection page 300 is shown to include an information selection menu or checkbox 318 with multiple information options or checkboxes 320-332 and a next button 336. Through interaction with the information selection menu 318 and the information options 320-332, the user of the user computing device 112 can indicate the type of information that will be analyzed and used in the HCP file generation process (e.g., the method 200). As shown, the information selection menu 318 includes multiple selectable options including a patient information option 320, an HCP information option 324, a prescription sales information option 328, and a national prescription information option 332. Only the HCP information option 324 will be described in detail herein. The HCP information option 324 is a selectable or clickable option of the information selection menu 318 through which the user of the user computing device 112 can indicate they would like to generate an HCP file and an HCP file generation request (as discussed in regard to the method 200). For example, the user of the user computing device 112 may select the HCP information option 324 and then select the selectable next button 336. In response, the user computing device 112 may send an indication to the provider computing system 104 that the user is about to generate an HCP file generation request. In response to the indication, the provider computing system 104 may provide medical device information and other information to the user computing device 112 that will be used in generating the HCP file generation request and as will be discussed further herein.

Figure 4A:
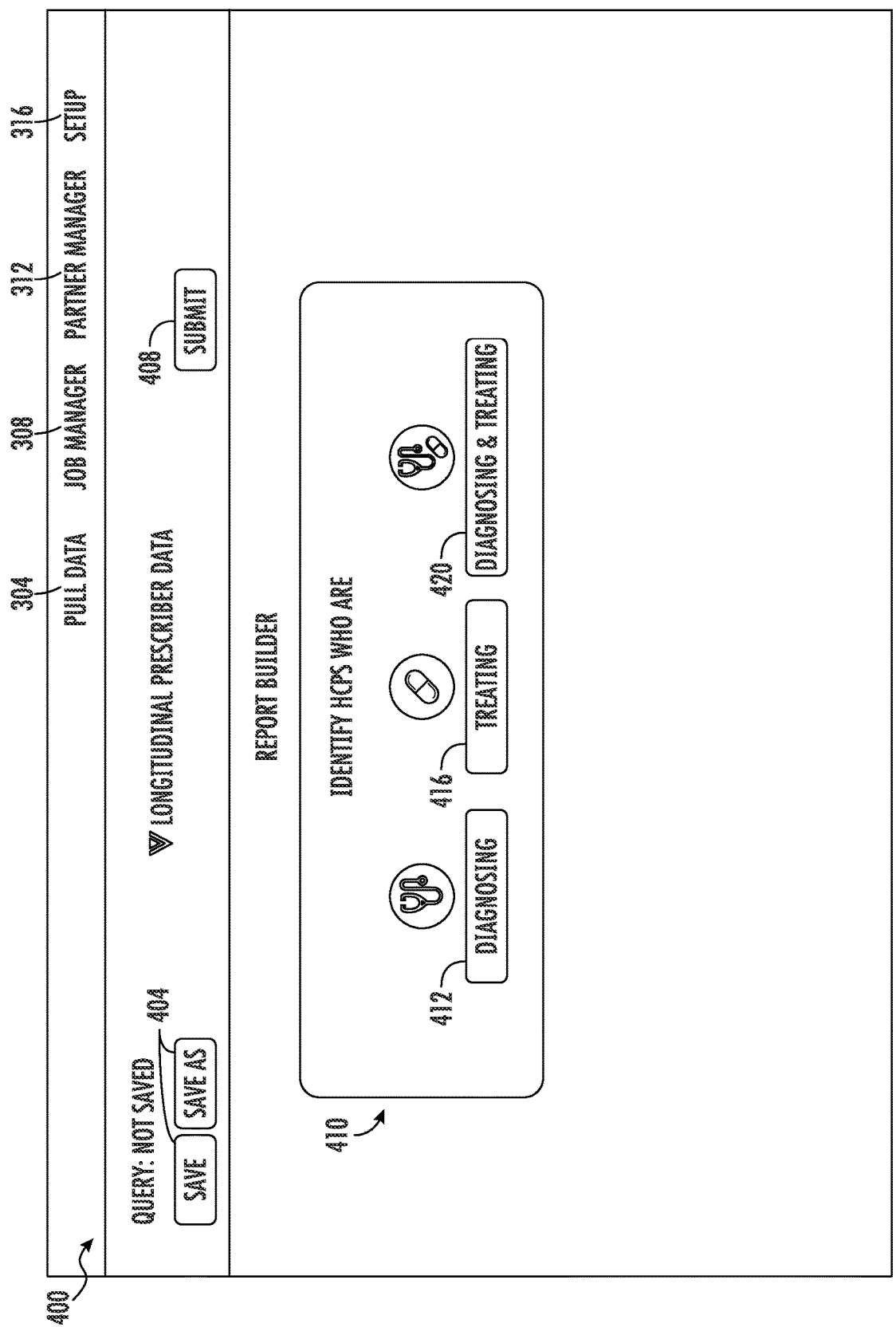
FIGS. 4A-4C are multiple illustrations of some aspects of a user interface generated by the longitudinal health information analyzation and dynamically structured electronic file generation system of FIG. 1 to determine the structure and file type of the electronic HCP file, according to an example embodiment.
Figure 4B:
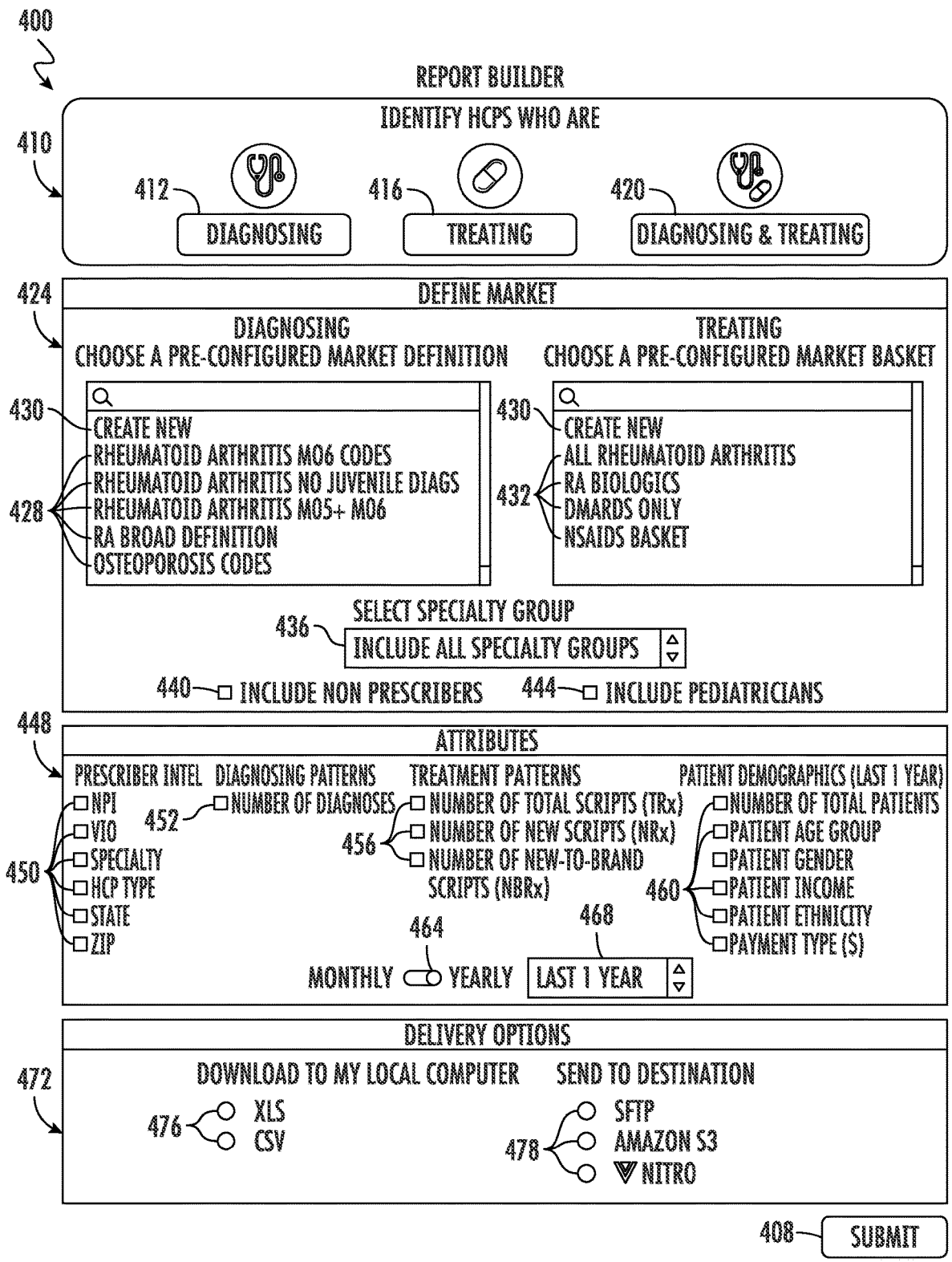
Figure 4C:
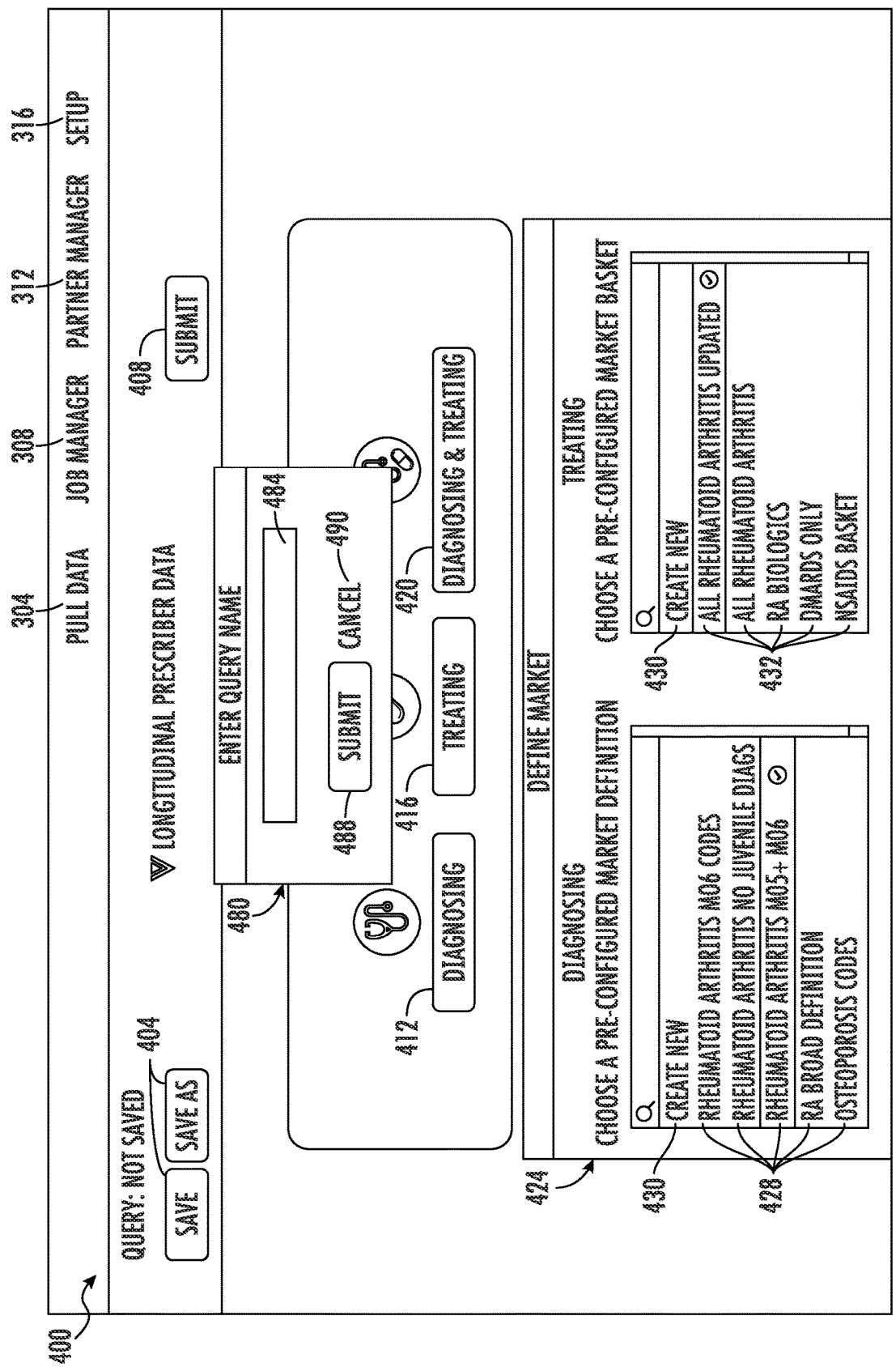

Referring now to FIGS. 4A-4C, an HCP file generation request page 400 (or HCP request page 400, for short) is shown. The HCP request page 400 can be displayed on a display of the I/O circuit 180 of the user computing device 112 and, in general, provides the user with an interface (e.g., a page including options, information, and other features that will be described herein) to generate an HCP file generation request. For example, through interaction with the HCP request page 400 the user of the user computing device 112 can generate an HCP request indicating how the health information, HCP information, and consumer information should be filtered; identifying the file destination, identifying the file type of the HCP file, and indicating the one or more HCP statistical values or insights that are to be generated. To access or be navigated to the HCP request page 400, the user of the user computing device 112 may navigate to the information selection page 300 (e.g., by selecting the pull data button 304), then select the HCP information option 324 of the information selection menu 318, and finally select the next button 336.

As shown, the HCP request page 400 includes the pull data button 304, the job manager button 308, the partner manager button 312, and the setup button 316, which all provide for navigation between various pages as described herein. The HCP request page 400 further includes multiple save buttons 404 (e.g., "Save" and "Save As), a submit button 408, and a health and HCP information filter menu 410.

The save buttons 404 allow the user of the user computing device to save the current HCP file generation request such that they can return to it at another point in time. The "Save As" button may provide a popup menu or box through which the user can name the current HCP file generation request or overwrite another saved HCP file generation request. The "Save" button may simply save a pre-named or selected HCP file generation request such that the user can return to it under that pre-selected name at another point in time. When the user selects either of the save buttons 404, the user computing device 112 may generate an HCP file generation request, with the currently selected information and details of the HCP request page 400 (including empty fields where the user has not made a selection yet) and provide the HCP file generation request to the provider computing system 104 with an indication that it is to be saved (but not used to generate an HCP file). The provider computing system 104 may receive the indication and the HCP file generation request and save the HCP file generation request (and accompanying selected information and name) in association with the account of the user. For example, the provider computing device may provide the HCP file generation request and accompanying information to the account database 132 for storage. The user of the user computing device 112 may then return to the saved HCP file generation request through selection of the job manager button 308 as will be described further herein.

The health and HCP information menu 410 is a menu that includes a diagnosing option 412, a treating option 416, and a diagnosing and treating option 420 and through which the user of the user computing device 112 can indicate one or more filters of the matched health information and HCP information. For example, through interaction with the health and HCP information menu 410, the user can generate an HCP file generation request that filters or instructs the provider computing system 104 to filter the matched health information and HCP information for HCPs with matched health information that includes specific diagnosing information (e.g., through selection of the diagnosing option 412), with matched health information that includes specific treating (medical product) information (e.g., through selection of the treating option 416), or with matched health information that includes specific diagnosing and specific treating information (e.g., through selection of the diagnosing and treating option 420).

When the diagnosing option 412, the treating option 416, or the diagnosing and treating option 420 are selected, new menus or sections of the HCP request page 400 may be generated in response. For example and referring specifically to FIG. 4B, when the user selects any of the options 412-420, the filter menu 424 may be generated and displayed, the HCP insights menu 448 may be generated and displayed, and the delivery menu 472 may be generated and displayed to the user of the user computing device 112. Moreover, each of the menus 424-472 may be generated and include specific options, selections, or pieces of information based specifically on the selected option of the health and HCP information menu 410. For example, in FIG. 4B the diagnosing and treating option 420 has been selected and therefore the filter menu 424 includes multiple diagnosing information filters 428 and multiple treatment or medical product filters 432.

In comparison, if the diagnosing option 412 was selected, the filter menu 424 may include the multiple diagnosing information filters 428 but not the medical product filters 432. Likewise, if the treating option 416 was selected, the filter menu 424 may include the medical product filters 432 but not the diagnosing information filters 428. Additionally, once the option of the health and HCP information menu 410 has been selected, the option (in FIG. 4B the diagnosing and treating option 420) may be emphasized or highlighted such that the option has a different color than the others. By highlighting the selected option, the HCP request page 400 may quickly and easily indicate the option that has been selected and provide such an indication to the user of the user computing device 112.

The filter menu 424 is a section of the HCP request page 400 through which the user of the user computing device 112 can customize and decide the specific filters that should be applied to the (matched) HCP information and health information to be used in generating the HCP file. As shown, the filter menu 424 includes diagnosing information filters 428, multiple new filter buttons 430, the medical product filters 432, the specialty information drop down box 436, the non-prescriber checkbox or option 440, and the pediatrician checkbox or option 444. The diagnosing information filters 428 may be selectable options that include dual functionality. If selected once, the diagnosing information filters 428 may indicate a diagnoses group filter that will be applied to the matched HCP and health information and specifically to the diagnosis information of the matched HCP and health information. For example, in FIG. 4B the "Rheumatoid Arthritis M05+M06" may specify or indicate that the matched HCP and health information is to be filtered to only include health information that includes diagnosis information for Rheumatoid Arthritis (RA) having a diagnosis code of M05 or M06. In this way, during the method 200, the provider computing system 104 that receives an HCP file generation request with the "Rheumatoid Arthritis M05+M06" diagnosis filter 428 may remove all HCPs and/or matched health information that does not include diagnosis information having a RA diagnosis code of M05 or M06. Thus, the resulting information that will be used to generate the HCP file will only be HCPs who have diagnosed RA with a diagnosis code of M05 or M06 and will only be for the patients who have been diagnosed with RA and a diagnosis code of M05 or M06.

Similarly, the medical product filters 432 may also be selectable options that include dual functionality. If selected once, the medical product filters 432 may indicate a medical product group filter that will be applied to the matched HCP and health information and specifically to the medical product information of the matched HCP and health information. For example, in FIG. 4B the "All Rheumatoid Arthritis" medical product information filter 432 may specify or indicate that the matched HCP and health information is to be filtered to only include HCPs matched with health information that includes medical product information for a group of medical products or drugs used to treat RA. The RA drugs or medical products may be received from the medical domain database 134 or from other databases, dictionaries, or the like that identify medical products used to treat RA. In this way, during the method 200, the provider computing system 104 that receives an HCP file generation request with the "All Rheumatoid Arthritis" medical product information filter 432 may remove all HCPs and/or matched health information that does not include medical product information that match a product in the list of RA drugs. Thus, the resulting information that will be used to generate the HCP file will only be HCPs who have prescribed a medical product treating RA and will only be for the health information of patients who have been prescribed the medical product treating RA.

If the user double selects (e.g., double clicks) the diagnosing information filter 428 or the medical product information filter 432, the user may be navigated to a page where they can define the diagnoses group or medical product group and therefore the specific filter. For example, if the user were to double click the "All Rheumatoid Arthritis" medical product information filter 432 the user may be navigated to a page where the user can define the specific list of drugs or medical products that define the "All Rheumatoid Arthritis" medical product group. In this way, the filters are customizable and may be decided specifically by the user. Likewise, if the user selects the new filter button 430, the user may be taken or navigate to a page where the user can create and define a new diagnoses group or medical product group and therefore the diagnosing information filter 428 or medical product information filter 432, dependent on which new filter button 430 the user selected (e.g., under the "Diagnosing" header or under the "Treating" header). Further details on creating, defining, or customizing a specific filter will be described with reference to FIG. 5.

The specialty information drop down box 436 is a drop down box that is selectable to drop down a plurality of specialty filters (not shown). Once selected and dropped down, the plurality of specialty filters are selectable to indicate and choose a filter that will be applied to the (matched) HCP information and health information. For example, the user of the user computing device 112 may select the specialty information drop down box 436, which may drop down the specialty filters "Cardiology" "Rheumatology," and "Neurology." The user of the user computing device may then select "Cardiology," which when provided to the provider computing system 104 in an HCP file generation request, may indicate the provider computing system 104 is to filter or remove all HCP information and matched health information that does not include "Cardiology" as specialty information (e.g., as a specialty). In this way, the provider computing system 104 may remove all HCPs (and corresponding HCP and health information) that is not a Cardiologist and return all Cardiologists in the HCP file. IN some embodiments, the multiple specialty filters of the specialty drop down box 436 are selectable such that the user can select multiple specialties of HCPs at one time.

Similarly, the non-prescriber checkbox or option 440 and the pediatrician checkbox or option 444 are each selectable options or checkboxes that, when selected, indicate the (matched) HCP information and health information are to be filtered. For example, the non-prescriber option 440, when not selected, may indicate the provider computing system 104 is to filter out or remove HCP information and matched healthcare information for HCPs who are not prescribers (e.g., medical interns). The provider computing system 104 may do so based on the type of the HCP included in the HCP information or based on the matched health information not including any Rx or Mx information. Likewise, the pediatrician option 444, when not selected, may indicate the provider computing system 104 is to filter out or remove HCP information and matched healthcare information for HCPs who are Pediatricians. The provider computing system 104 may do so based on the type of the HCP or the specialty of the HCP included in the HCP information.

Still referring to FIG. 4B, the HCP insights menu 448 is shown to include HCP options or checkboxes 450, a diagnosis statistical value or insight option or checkbox 452, multiple treatment or medical product statistical value or insight options or checkboxes 456, multiple patient insights or statistical value options or checkboxes 460, a time unit selector 464, and a timeframe drop down box 468. Through interaction with the HCP insights menu 448, the user of the user computing device 112 can specify the HCP information, the timeframe and time interval, and the HCP statistical values to be included in the HCP file. While all the HCP statistical values discussed with regard to step 236 of the method 200 are not shown to be included in the HCP insights menu 448, it should be understood that the HCP insights menu 448 may include selectable options or checkboxes for each (e.g., median quantity of each medical product specified in the medical product information filter 432 dispensed, etc.).

The HCP options or checkboxes 450 are selectable checkboxes that may be selected or unselected to specify the HCP information (e.g., NPI, VID, Specialty, HCP type, State, and/or zip) to be included in the HCP file. By selecting or deselecting each of the HCP checkboxes 450, the user of the user computing device 112 may specify what HCP information is to be included in the HCP file.

The diagnosis statical value checkbox 452 may include an HCP statistical value associated with the diagnosis (as defined by the diagnosis information filters 428) that can be generated and included in the HCP file, in response to the checkbox 452 being selected. As shown, the diagnosis statistical value checkbox 452 is shown to be the total number of diagnoses for each specific diagnosis. The total number of diagnoses may be determined by adding up each piece of diagnosis information for a specific diagnosis code included in the health information matched with a single HCP. This process may be repeated for each HCP and for each diagnosis code included in the diagnosis filter 428. In another example, the HCP insights menu 448 may include a diagnosis statistical value checkbox 452 for a total number of diagnosis overall. The total number of diagnosis may be determined by adding up diagnosis, regardless of diagnosis code, included in the health information matched with a single HCP. This process may be repeated for each HCP. In a third example, the HCP insights menu 448 may include a diagnosis statistical value checkbox 452 for a diagnosis code percentage. The diagnosis code percentage may be determined by determining the total diagnoses for each specific diagnosis and dividing it by the total number of diagnoses overall for each HCP. This process may be repeated for each specific diagnosis and for each HCP.

Likewise, the treatment or medical product statistical value checkboxes 456 may each include an HCP statistical values associated with each medical product (as defined by the medical product filters 432) that can be generated and included in the HCP file, in response to each checkbox 456 being selected. As shown, the medical product statistical value checkbox 456 includes a number of total prescriptions for each medical product checkbox, a number of new prescriptions for each medical product checkbox, and a number of new-to-brand prescriptions for each medical product checkbox. The number of total prescriptions (TRx) for each medical product may be determined by adding up or summing the volume of prescriptions filled for patients treated by each HCP. The number of new prescriptions (NRx) for each medical product may be determined by adding up or summing each first prescription of a medical product dispensed, not a refill of a medical product, for patients treated by each HCP. The number of new-to-brand prescriptions (NBRx) may be determined by adding up or summing each of the first prescription of a specific brand of the medical product for patients treated by each HCP. Further, while not shown, the total number of medical claims processed (TMx) may be determined by adding up or summing the volume of medical claims processed for each medical product for patients treated by each HCP. While also not shown, the total number of prescriptions filled and medical claims processed (TMRx) may be determined by adding up or summing the volume of prescriptions filled and medical claims processed for each medical product for patients treated by each HCP. Likewise, the total number of new-to-brand medical claims (NBMx) may be determined by adding up or summing the first medical claim processed of a specific brand of the medical product for patients treated by each HCP. Lastly and while not shown, the total number of new-brand-starts (NBS) may be determined by adding up or summing each of the first prescription or the first medical claim processed of a specific brand of the medical product to patients treated by each HCP. It should be understood that HCP statistical values that include Rx (e.g., NBRx, TMRx, TRx) as well as the NBS may be determined based on prescription claims (Rx) health information, and HCP values that include Mx (e.g., NBMx, TMRx, TMx) as well as the NBS may be determined based on medical claims (Mx) health information. All these calculations may be repeated for each medical product and for each HCP and may be reported as an individual number or as a percentage of a whole.

The patient statistical value checkboxes 460 may each include an HCP statistical value for patients associated with the HCP (also referred to as associated patients) (e.g., patients that have been prescribed a medical product by the HCP or been diagnosed by the HCP) that can be generated and included in the electronic file, in response to each checkbox 460 being selected. As shown, the patient statistical value checkboxes 460 includes a number of total patients checkbox, a patient age group checkbox, a patient gender checkbox, a patient ethnicity checkbox, and a payment type checkbox. The total number of patients for each HCP may be determined by summing each individual piece of deidentified identity information (e.g., name, social security number). The % per age group of patients for each HCP may be determined by determining the age for each associated patient of the HCP based on the health information or the consumer information associated with the patient, summing up the number of patients within each age group (i.e., 0-18, 19-25, 26-40, etc.) and then dividing the number of patients within each age group by the total number of patients for each HCP. The patient gender may be determined by determining the gender for each associated patient of the HCP based on the health information or the consumer information associated with the patient, summing up the number of patients of each gender, and then dividing the number of patients of each sex by the total number of patients for each HCP. The patient income may be determined by determining the income for each associated patient of the HCP based on the consumer information associated with the patient, summing up the number of patients within each income group (i.e., $0-10,000; $10,001-30,000; etc.), and then dividing the number of patients of each income group by the total number of associated patients for each HCP. Patient ethnicity may be determined by determining the ethnicity for each associated patient of the HCP based on the consumer information or the health information, summing up the number of patients of each ethnicity, and then dividing the number of patients of each ethnicity by the total number of patients for each HCP. Lastly, the payment type may be determined by determining the payment type for each transaction within the health information, summing up the number of each payment type, and then dividing the number of payments of each payment type by the total number of transactions. In some embodiments gender, income, age group, ethnicity, and payment type are reported as an overall number (e.g., a sum for each) or as percentage for each.

The time unit selector 464 and the timeframe drop down box 468 are two menu options through which the user of the user computing device 112 can set the timeframe for the HCP and health information used to generate and included in the HCP file. For example, the time unit selector 464 is a selectable option that applies the unit to the timeframe drop down box 468. As shown, the time unit selector 464 is movable between monthly and yearly. Therefore, through interaction with the time unit selector 464, the user can decide if they want the time frame to be measured in months or in years. Then, once the time unit selector 464 is set on the correct unit, the user can select the timeframe drop down box 468 and select the timeframe within which they want the HCP information and health information to be. For example, with the time unit selector 464 set to yearly, the user may select the time frame drop down box 468 and select the drop down option "Last 1 Year." Once set and the HCP file generation request is sent to the provider computing system 104, the provider computing system 104 may then only use health information or HCP from within the last year. In some embodiments, the time frame drop down box 468 can include the drop down options of last 1, 2, 3 . . . 12 months, when the time unit selector 464 is on monthly and the options of last 1, 2, 3, 4, 5, 20 years, when the time unit selector 464 is on yearly.

Still referring to FIG. 4B, the delivery menu 472 is shown to include multiple file type options 476 and multiple file destination options 478. Through interaction with the delivery menu 472, the user of the user computing device may decide the specified file type of the HCP file as well as the file destination address. In this regard, the file type options 476 are selectable options through which the user can decide the specified file type into which the HCP file will be generated. For example, the delivery menu 472 is shown to include a XLS file type option 476 and a CSV file type option 476. If the user selects the XLS file type option 476 and proceeds to generate submit the HCP file generation request to the provider computing system 104, the provider computing system 104 may generate the HCP file as the specified XLS file type. Further, in some embodiments, the file type options 476, when selected, may further indicate file destination address is the IP address of the user computing device 112, such that the HCP file may be provided to the user computing device 112 via the internet. In other embodiments, the file destination may be indicated as being the IP address of the user computing device 112 if no file destination option 478 is selected.

The file destination options 478 are selectable options that allow the user to decide and indicate the file destination address to which the HCP file is to be provided. For example, the delivery menu 472 is shown to include a Secure FTP (SFTP) file destination option 478, an Amazon S3® file destination option 478, and a Veeva Nitro® file destination option 478. If the user selects the SFTP file destination option 478, a popup may be generated on the user computing device 112 requesting an FTP address to which the HCP file is to be provided. Once the user provides an address and submits the HCP file generation request, the provider computing device 112 may generate the HCP file, as the specified file type indicated by the selected file destination option 476 and provide the HCP file to the FTP address received from the user.

Referring to FIG. 4C, once the user has finished filling out specifying each option and field of the HCP file generation request via the HCP request page 400, the user may select the submit button 408. When the submit button 408 is selected, the user computing device 112 may generate and display a request popup box 480 to the user. The request popup box 480 may include a name text field 484, a second submit button 488, and a cancel button 490. The user may then type or enter (e.g., via a keyboard of the input device of the I/O circuit 180) a name of the HCP file generation request into the name text field 484 and select the second submit button 488. Once selected, the user computing device 112 may generate an HCP file request including all of the options, details, and selections of the user on the HCP request page 400 and provide the HCP file request to the user provider computing device 112. In this regard, it should be understood that an HCP file generation request may include any of the options, features, menus, or information selections shown and described with regard to the HCP request page 400. If the user instead selects the cancel button 490, the request popup box 480 may be closed or removed from the HCP request page 400.

Figure 5:
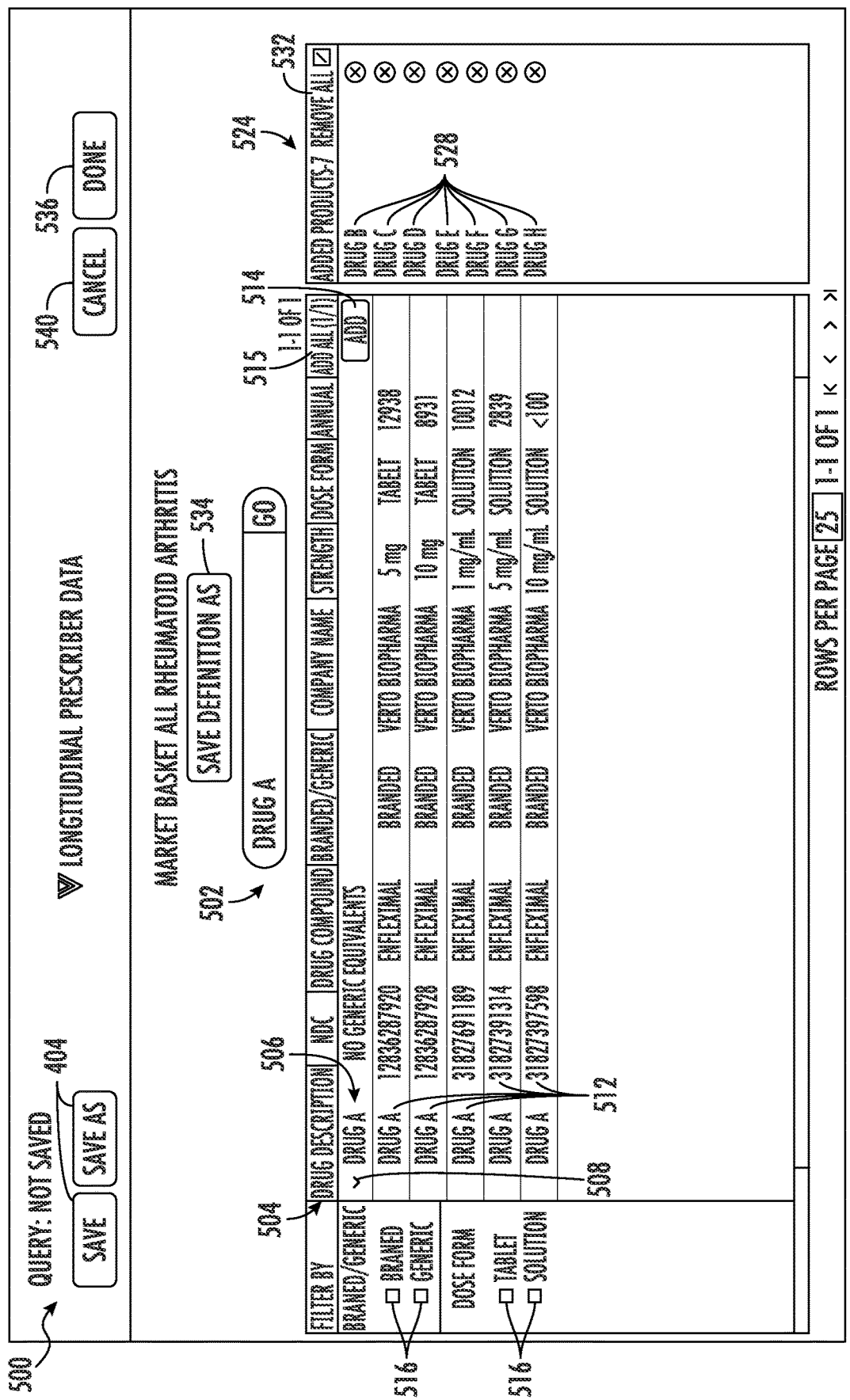
FIG. 5 is an illustration of some aspects of a user interface generated by the longitudinal health information analyzation and dynamically structured electronic file generation system of FIG. 1 to modify a medical product group, according to an example embodiment.

Referring now to FIG. 5, a medical product group selection page 500 is shown. The medical product group selection page 500 can be displayed on a display of the I/O circuit 180 of the user computing device 112 and, in general, provides the user with an interface (e.g., a page including options, information, and other features that will be described herein) to define a medical product group. For example, through interaction with the medical product group selection page 500 the user of the user computing device 112 can generate or define a medical product group which can then be displayed on the HCP request page 400 as one of the medical product filters 432 and used to filter the matched HCP information and health information. To access or be navigated to the medical product group selection page 500, the user of the user computing device 112 may double select or click one of the medical product filters 432 or select the new filter button 430 under the treatment header. If the user double selects one of the medical product filters 432, the user may be navigated to the medical product group selection page 500 which may be automatically populated with information pertaining to the selected medical product group. By contrast, if the user selects the new filter button, the user may be navigated to the medical product group selection page 500 which may not be populated with any information pertaining to a medical product group.

As shown, the medical product group selection page 500 includes the multiple save buttons 404, a medical product search bar 502, a medical product search results section 504, multiple search result filter options 516, a medical product group summary section 524, a save new medical group button 534 button, a done/submit button 536, and a cancel button 540. When the user is directed to the medical product group selection page 500, the user is typically trying to edit or create a new medical product group with one or more medical products. As a result, the medical product search bar 502 is a selectable bar with a text entry field and a search or go button. In use, the user of the user computing device 112 may type or enter a medical product identifier (e.g., name, national drug code (NDC), chemical formula) into the text entry field of the medical product search bar 502 and select the go button. When the go button is selected, the user computing device may send a medical product query or request including the medical product identifier to the provider computing system 104. In response, the provider computing system 104 may query or search the medical domain database 134 for information pertaining to the medical product identifier. If a result or multiple results are found, the provider computing system 104 may provide the results to the user computing device 112.

In this regard, the medical product search results section 504 is a section of the medical product group selection page 500 in which medical product search results received from the provider computing system 104 are displayed by the user computing device 112. Through interaction with the medical product search results section 504, the user of the user computing device 112 can review and add one or more of the medical product search results to the medical product group. As shown, the medical product search results section 504 includes one or more medical product 506 search results (depending on the search results received from the provider computing system 104) and an add all button 515. The medical product search result 506 is shown to include a toggleable button 508, medical product information 512, and an add button 514.

The toggleable button 508 is a selectable button that hides or displays the medical product information of the respective medical product search result 506. In this regard, the user may select the toggleable button 508 to hide the medical product information 512 and to review the medical product search results 506 more quickly and then select the toggleable button 508 again to see the medical product information pertaining to the respective medical product search result 506 and do a more thorough review.

The medical product information 512 of the medical product search result 506 may be any medical product information described herein but is shown to include a medical product description or brand name, a medical product NDC, a chemical compound of the medical product, a company name, the strength of the medical product, the dose form of the medical product, and the annual count (number sold) of the medical product. As shown, each medical product search result 506 may comprise each type of the respective medical product (e.g., tablet version, solution version, different dosages, etc.) such that only one medical product search result 506 is returned for all forms of a single medical product.

Once the user has reviewed the medical product information 512 of the medical product search result 506 and determines they want to add the medical product to the medical product group, the user may select the add button 514. The add button 514 may add the medical product associated with the medical product search result 506 to the medical product group such that it appears in the medical product group summary 524. Similarly, the add all button 515 may add the respective medical product associated with each search medical product search result 506 of the medical product search results section 504 to the medical product group such that each medical product appears in the medical product group summary 524.

Still referring to FIG. 5, the filter options 516 are selectable options or checkboxes that, when selected, filter the medical product search results 506 of the medical product search results section 504. For example, the filter options 516 are shown to include a branded filter option 516, a generic filter option 516, a tablet filter option 516, and a solution filter option 516. If the user of the user computing device were to select the tablet filter option 516, the user computing device 112 may filter the medical product search results 506 and display only medical product search results 506 that are available as a tablet form (e.g., that include medical product information 512 indicating a tablet dose form) in the medical product search results section 504. Likewise, if the user were to select the branded filter option 516, the user computing device 112 may filter the medical product search results 506 and display only medical product search results 506 that are available as a branded medical product (e.g., that include medical product information 512 indicating a branded type of the medical product).

If at any time the user would like to review the medical products added to or currently included in the medical product group, the user can do so using the medical product group summary section 524. The medical product group summary section 524 is a section of the medical product group selection page 500 that provides a summary of the medical products currently included in the medical product group. As shown, the medical product group summary section 524 includes multiple medical product titles or names 528 and a remove all button 532. The medical product names 528 provide a quick idea of which medical products are in the medical product group and each include a remove button. The remove button (i.e., the "X" button on the righthand side of each medical product name 528) is a selectable button that, when selected, removes the medical product identified by the medical product name 528 from the medical product group. Likewise, the remove all button 532 is a selectable button that, when selected, removes all of the medical products identified by the medical products names 528 from the medical product group.

Once the user has finished adding or removing medical products from the medical product group, the user can save the medical product group, cancel the changes to the medical product, or save the medical product group as a new group entirely. To do so, the user can interact with the save new medical group button 534, the done/submit button 536, or the cancel button 540. The save new medical group button 534 is a selectable button that, when selected generates a popup to name the medical group. Once the user has named the medical group, the user computing device 112 will provide the medical product group including the medical products added by the user to the provider computing system 104. The provider computing system 104 may store the medical product group in association with an account of the user in the database 132 or the medical domain database 134. The medical product group may then be used to filter the matched health and HCP information as described herein. Likewise, the done/submit button 536 is a selectable button 536 that, when selected, updates the currently access medical product group to include the medical products specified by the user and provides the updated medical product group including the medical products to the provider computing system 104 for storage as described herein. Lastly, the cancel button 540 is a selectable button that, when selected, discards any changes to the medical product group and returns the user to the HCP request page 400 (i.e., cancels the changes to the medical product group).

While the figures and description provided above are specific to the medical product group selection page 500, the medical product groups, and medical products, it should be understood that a similar diagnoses group selection page (not shown) is accessible by selecting the diagnosing information filter 428 twice or by selecting the new filter button 430 under the diagnosing header. The diagnoses group selection page may include all of the same features and sections of the medical product group selection page 500 with application to the diagnoses groups described herein. For example, the user may access the diagnoses group selection page and be presented with a diagnoses search bar, a diagnosis search results section, a diagnoses group summary section, and so on. Through interaction with the diagnoses group selection page, the user may customize or generate new diagnoses groups that can be displayed and applied as filters via the diagnosing information filters 428. Additionally, in some embodiments, the provider computing system 104 includes a diagnoses database that returns diagnoses search results in response to the user entering a diagnosis search in the diagnoses search bar.

Figure 6A:
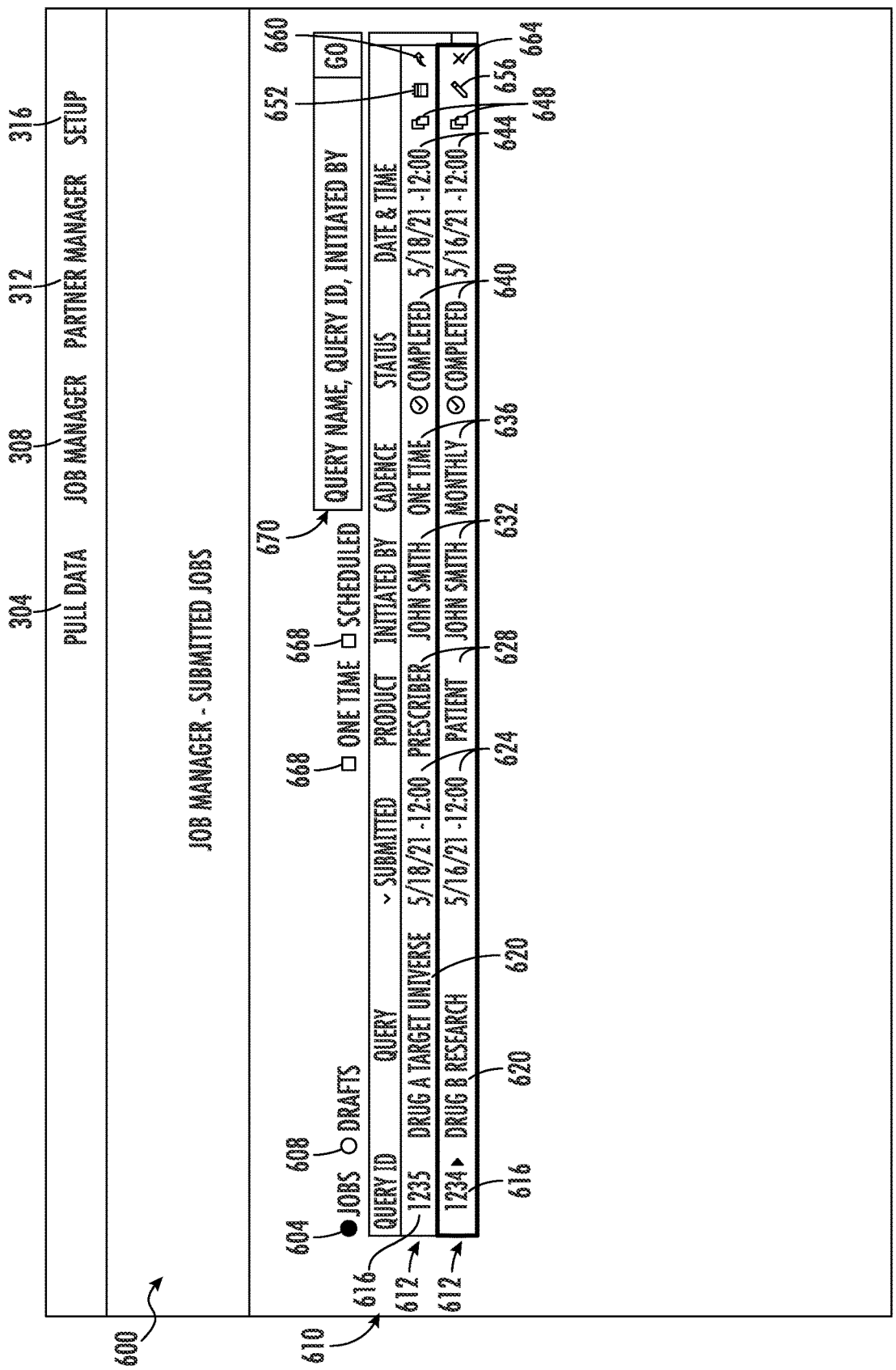
FIG. 6A-6B are multiple illustrations of some aspects of a user interface generated by the longitudinal health information analyzation and dynamically structured electronic file generation system of FIG. 1 to manage HCP file generation requests, according to an example embodiment.
Figure 6B:
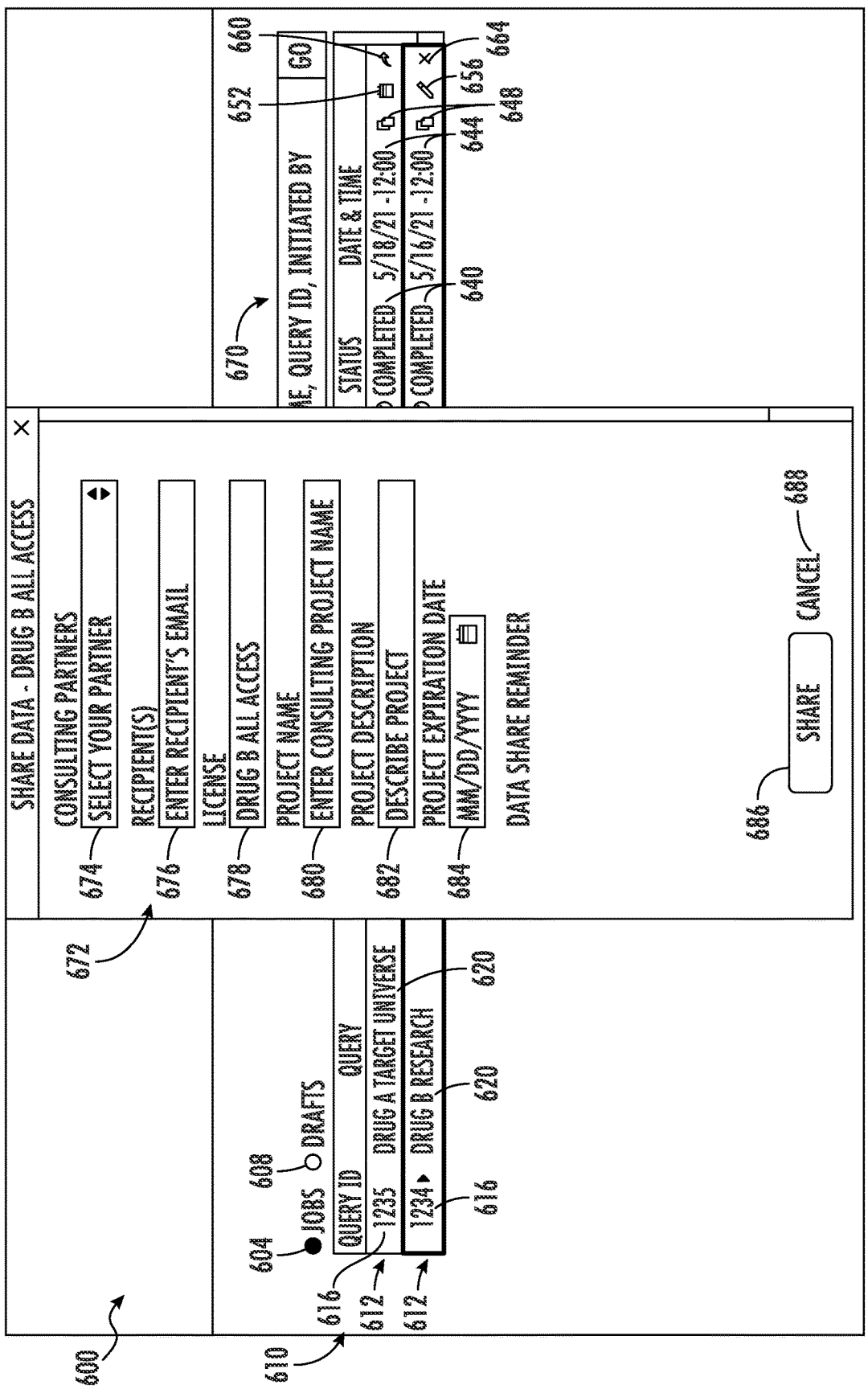

Referring now to FIGS. 6A-6B, an HCP file generation request management page 600 (request management page 600, for short) is shown. The request management page 600 can be displayed on a display of the I/O circuit 180 of the user computing device 112 and, in general, provides the user with an interface (e.g., a page including options, information, and other features that will be described herein) to manage HCP file generation requests. For example, through interaction with the request management page 600 the user of the user computing device 112 can manage one or more HCP file generation requests including scheduling a time interval for HCP file generation requests and accessing, replicating, or deleting saved, but not submitted and generated, HCP file generation requests. To access or be navigated to the request management page 600, the user of the user computing device 112 may select the job manager button 308.

As shown, the request management page 600 includes the pull data button 304, the job manager button 308, the partner manager button 312, the setup button 312, a submitted request option or checkbox 604, a draft (i.e., saved but not submitted) request option or checkbox 608, and a request management section 610. The submitted request option 604 and the draft request option 608 are each selectable options that manage the information displayed by the request management section 610. For example, if the submitted request option 604 is selected, the request management section 610 may display request summaries 612 that represent HCP file generation request that have been generated and provided to the provider computing system 104. In comparison, if the draft request option 608 is selected, the request management section 610 may display request summaries 612 of HCP file generation requests that have been saved (as discussed with regard to the saver buttons 404) but not used for generation of an HCP file.

The request management section 610 may display HCP file generation request summaries 612 that each summarize an HCP file generation request that has been saved or used to generate an HCP file (depending on the selection of the option 604 or 608). Each request summary 612 may include multiple request information fields such as a request ID field 616, a request name field 620, the request submission time 624, a product field 628, a request submitting account identifier field 632, a request status field 640, and a status time 644. Each field of the request summary 612 will not be described in detail herein, but it should be understood that each field of the request summary 612 may be populated and received via the HCP request page 400 and may be included in an HCP file generation request.

To manage and filter the request summaries 612 that are shown and displayed in the request management section 610, the request management page 600 is further shown to include multiple request summary filter options 668 or checkboxes and a request summary search bar 670. The summary filter options 668 are selectable options or checkboxes that, when selected, filter the request summaries 612 displayed in the management section 610. For example, the request management page 600 is shown to include a one time request summary filter option 668 and a scheduled request summary filter option 668. If the user selects the scheduled summary filter option 668, the user computing device may remove or not display request summaries 612 that only occurred one time/that are not scheduled as will be described herein. Likewise, the request summary search bar 670 is a search bar through which the user can enter HCP file generation request identifiers (e.g., name, ID, date, etc.) and then select the search button. Once selected, only request summaries that match the identifier(s) will be displayed in the request management section 610.

Each request summary 612 is further shown to include a duplicate request button 648, a schedule button 652 or edit schedule button 656, and a share button 660 or a cancel schedule button 664. The duplicate request button 648 is a selectable button that, when selected, may navigate the user to the HCP request page 400 having the same fields and options filled out as those of the HCP file generation request represented by the request summary 612. For example, if the HCP file generation request was generated using the HCP request page 400 having the "All Rheumatoid Arthritis" medical product information filter 432 selected, selecting the duplicate request button 648 may navigate the user to the HCP request page 400 having the "All Rheumatoid Arthritis" medical product information filter selected 432 as well. In this regard, each HCP file generation request represented by the request summary 612 may be substantially duplicated.

The schedule button 652 is a selectable button that, when selected, may generate a popup (not shown) to schedule the HCP file generation request represented by the request summary 612 to be generated or provided to the provider computing system 104 at a specific time interval or rate. For example, via the popup and after selecting the schedule button 652, the user of the user computing device 112 may indicate they want the HCP file generation request represented by the request summary 612 to be provided to the provider computing device 104 and a corresponding HCP file generated once a month, twice a month, once a week, every two days, etc. Likewise, if the HCP file generation request represented by the request summary 612 is already scheduled to be provided to the provider computing system 104 at a specific time interval or rate, the request summary 612 may include the edit schedule button 656. The edit schedule button 656 is a selectable button that, when selected, may provide the user with an interface (e.g., a popup) to edit the specific time interval or rate at which the HCP file generation request represented by the request summary 612 is provided to the provider computing system 104 (e.g., from every month to every two months). Additionally, the cancel schedule button 664 is a selectable button that may be selected to cancel the scheduling of the HCP file generation request represented by the request summary 612 and stop the providing of the HCP file generation request to the provider computing device 104 at a specific time interval or rate.

The share button 660 is a selectable button that, when selected, provides the user with an interface to share the generated HCP file with a recipient, as described herein. For example and referring to FIG. 6B, when the user of the user computing device 112 selects the share button 660, the HCP share popup 672 may be generated and displayed (e.g., overlaid) on the request management page 600. Through interaction with the HCP share popup 672, the user computing device 112 may generate a file share request and provide the file share request to the provider computing system 104. As shown, the HCP share popup 672 is shown to include a recipient drop down box 674, a recipient address text field 676, a license field 678, a project name field 680, a project description field 682, an expiration date/time field 684, a submit button 686, and a cancel button 688.

Each field of the HCP share popup 672 will not be described in detail but it should be understood that by entering a recipient address in the recipient address text field 676, the user decides and submits the recipient address of the file share request. Further, by entering an expiration date/time in the expiration date/time field 684, the user can decide the expiration date/time of the file share request.

Once the user has finished filling out each field of the HCP share popup 672, the user may select the submit button 686 or the cancel button 688. In response to the user selecting the submit button 686, the user computing device 112 may generate the file share request, including the recipient address of the recipient address text field 676 and the expiration date/time of the expiration date/time field 684, and provide the file share request to the provider computing system 104. In comparison, if the user selects the cancel button 688, the user computing device 112 may discard the information included within the HCP share popup 672 and close the HCP share popup 672.

Figure 7:
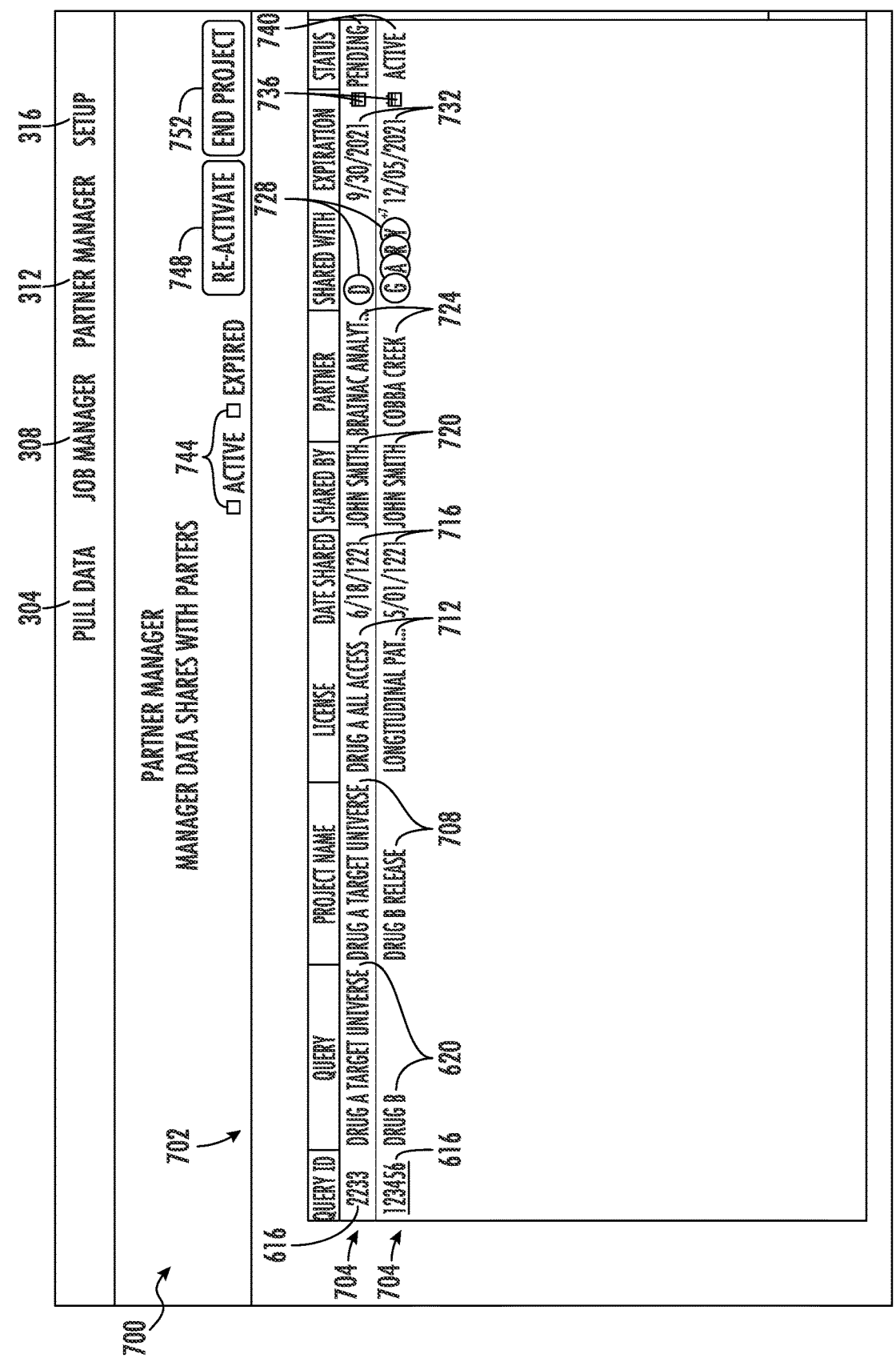
FIG. 7 is an illustration of some aspects of a user interface generated by the longitudinal health information analyzation and dynamically structured electronic file generation system of FIG. 1 to manage sharing of a generated electronic HCP file.

Referring now to FIG. 7, an HCP file share management page 700 is shown. The file share management page 700 can be displayed on a display of the I/O circuit 180 of the user computing device 112 and, in general, provides the user with an interface (e.g., a page including options, information, and other features that will be described herein) to manage file share requests. For example, through interaction with the file share management page 700 the user of the user computing device 112 can manage one or more file share requests including altering (e.g., extending or shortening) the expiration date/time of the file share request. To access or be navigated to the file share management page 700, the user of the user computing device 112 may select the partner manager button 312.

As shown, the file share management page 700 includes a file share request management section 702, multiple file share request filter options 744, a reactivate button 748, and an end button 752. The file share request management section 702 may display multiple file share request summaries 704 that each summarize a file share request that has been provided to the provider computing system 104, and therefore used to provide the HCP file to the recipient address (e.g., the recipient computing device 116). Each file share request summary 704 may include multiple file share request fields such as the request ID field 616, the request name field 620, a project name field 708, a license field 712, a date/time of sharing field 716, a shared by account identifier field 720, a partner field 724, a shared with field 728, an expiration date/time field 732, and a status field 740. Each field of the file share request summary 704 will not be described in detail herein, but it should be understood that each field of the file share request summary 704 may be included in a file share request.

Each file share request summary 704 is further shown to include a schedule button 736 which is a selectable button that when selected, may generate a popup (not shown) to alter the expiration date/time of the file share request represented by the file share request summary 704. For example, via the popup or other interface generated when selecting the schedule button 736, the user of the user computing device 112 may indicate they want to extend the expiration date/time of the file share request by three days. In response, the user computing device 112 may indicate the new file share request expiration date/time to the provider computing system 104 or provide another file share request to the provider computing system 104. The recipient of the recipient computing device 116 associated with the recipient address may then access, download, and view the HCP file for an additional two days.

The file share request filter options 744 are selectable options or checkboxes that, when selected, filter the file share request summaries 704 shown within the file share request management section 704. For example, the file share management page 700 is shown to include an active file share request filter option 744 and an expired file share request filter option 744. If the user were to select the expired file share request filter option 744, the user computing device may remove or not show file share request summaries 704 for file share requests that are active and show or display file share request summaries 704 for file share requests that are expired (e.g., as indicated by the status field 740).

If a file share request is expired (e.g., the expiration date/time has passed) and the user wishes to reactivate it, the user may select the file share request summary 704 (e.g., by click on any of the fields of the file share request summary 704) representing the file share request and then select the reactivate button 748. The reactivate button 748 is a selectable button that, when selected, may generate a popup or other interface through which the user of the user computing device can reactivate the expired file share request. For example, the user may indicate a new expiration date/time for the expired file share request. In response, the user computing device 112 may generate a new file share request with the same information (e.g., recipient address) as the expired file share request and the new expiration date/time and provide it to the provider computing system 104, which may then share the HCP file with the recipient computing device 116. Likewise, if a file share request is active and the user wishes to end it, the user may select the file share request summary 704 representing the file share request and then select the end project button 752. In response, the user computing device 112 may send an indication that the expiration date/time of the file share request is past and the HCP file is to not be shared with the recipient address.

Referring now FIGS. 8A-C, an electronic file 800 (also referred to as an HCP file 800) is shown according to an example embodiment. The electronic file 800 is shown to include NPI information for each HCP, a VID number for each HCP, HCP location information for each HCP (e.g., state, zip), specialty information for each HCP, HCP type for each HCP, number of diagnoses for each HCP, medical product prescription numbers for each medical product specified in a medical product group (e.g., drug 1, drug 2, drug 3, and so on) and each HCP, new-to-brand prescriptions for each brand of medical product specified in the medical product group and each HCP, total number of patients seeing each HCP, payment type percentages for patients seeing each HCP (e.g., % of payments from Medicare, % of payments from Medicaid, % of payments from commercial health insurance, and % of payments in cash), and income range percentages of patients seeing each HCP.

As described herein, each electronic file may be a specified file type and be structured as selected by the user via the HCP request page 400. For example, the electronic file 800 is shown to be a .XML file but may be other file types, as decided by the user through the file type options 476 of the HCP request page 400. Further, while the electronic file 800 is shown to include new prescriptions and new-to-brand prescriptions HCP statistical values, the user may decide, via the medical product statistical value or insight options or checkboxes 456 of the HCP request page 400, to include other HCP statical values within the HCP file. In this regard, the electronic file 800 is just one example of many different possible structures and file types of the HCP file.

Figure 9A:
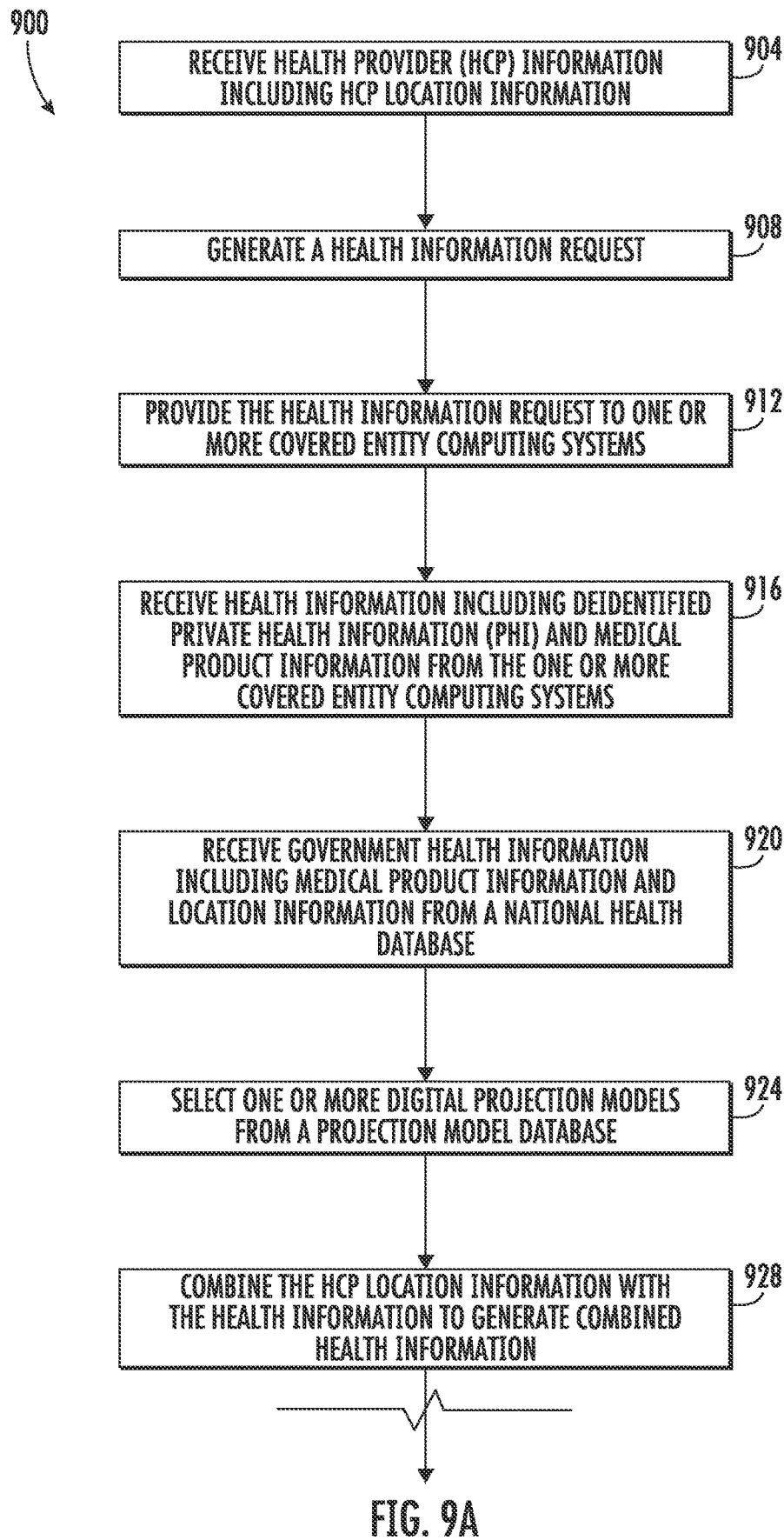
FIGS. 9A-9B are a flow diagram of a method for analyzing longitudinal health information and generating a dynamically structured electronic defined location prescribing file, according to an example embodiment.
Figure 9B:
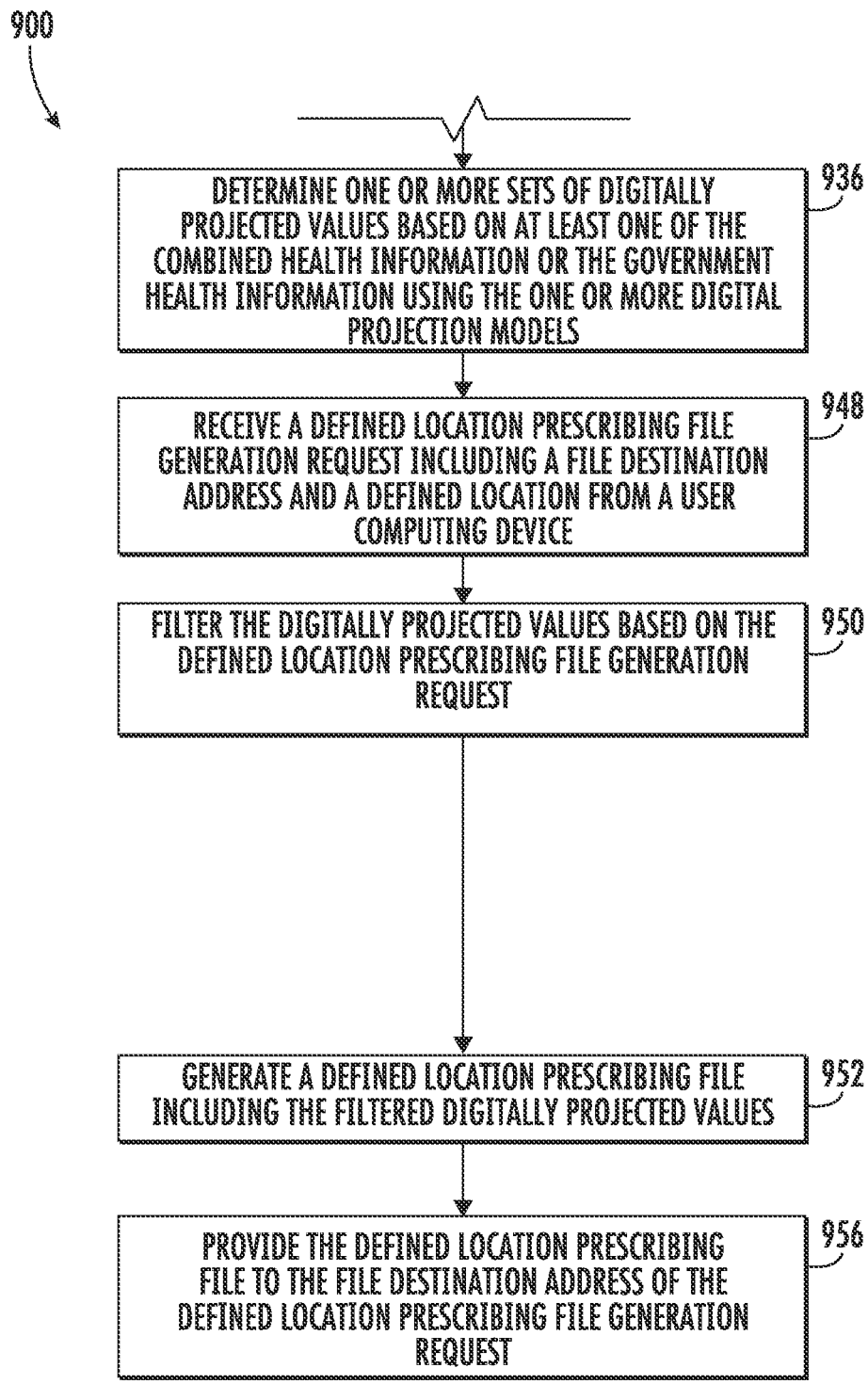

Referring now to FIGS. 9A-9B, a method 900 for analyzing longitudinal health information and generating a dynamically structured electronic defined location prescribing file is shown, according to an example embodiment. While different overall, it should be understood that any steps or discussion of the method 900 may be applied or included within the method 200, and vice versa, and that such combinations are included within the scope of the present disclosure. For example, the method 200 may include any of the steps 904-956, after or before any steps included in the method 200, and the method 900 may include any of the steps 904-268, after or before any of the steps included in the method 900. Method 900 can be carried out by the system of FIG. 1. More particularly, the method 900 can be carried out by the processing circuit 128 of the provider computing system 104 and through communication with the user computing device 112, the covered entity computing system(s) 108, and/or the recipient computing device 116.

Method 900 commences at step 904 at which the provider computing system 104 receives or selects HCP information from the HCP database 124. The HCP information may be associated with multiple HCPs and may include HCP location information for each of the HCPs. In some embodiments, at, before, or after step 904, the provider computing system 104 may receive other information used to populate the health information request such as consumer information (from the consumer database 120), timeframe information, medical product information (from the medical domain database 134), and other information described herein as being included in the health information request. In some embodiments, the provider computing system 104 receives HCP information (or the other information with which the health information request is populated) from the HCP database 124 at specific time intervals (e.g., the same as or different than the specific intervals at which the health information requests are generated).

Once the provider computing system 104 has received the HCP information, the method 900 proceeds to step 908 at which the provider computing system 104 generates a health information request. As described herein, the health information request may be generated and populated to include the information received at step 904 such as the HCP information, the consumer information, the medical product information, and the timeframe information. The health information request 908 may request health information that is associated with or matches the information included in the health information request. In some embodiments, the health information request 908 may request health information that is not associated with or does not match the information included in the health information request.

In some embodiments, at step 908, the provider computing system 104 may generate multiple health information requests. For example, the provider computing system 104 may generate a health information request for each covered entity computing system from which health information is sought. In other embodiments, the provider computing system 104 may generate a single, reused, health information request that is sent to each covered entity computing from which health information is sought.

Additionally, at step 908, the provider computing system 104 may generate the health information request, at a specific time interval or rate (e.g., once a day, once a week, once a month, every 5 minutes, etc.). In some embodiments, the specific time interval or rate at which the health information request is generated is different than the specific time interval or rate at which the HCP information, medical product information, and/or consumer information is received. In other embodiments, the specific time interval or rate at which the health information request is generated is the same as the specific time interval or rate at which the HCP information, medical product information, and/or consumer information is received. By doing so, the provider computing system 104 may generate an updated health information request including the most recently received HCP, medical product, and/or consumer information.

Once the provider computing system 104 has generated the health information request, the method 900 proceeds to step 912 at which the provider computing system 104 provides the health information request to one or more covered entity computing systems (e.g., the covered entity computing system 108). In some embodiments, the provider computing system 104 may provide the health information request over the network 118 via the network interface circuit 126 to the one or more covered entity computing systems 118.

Once the provider computing system 104 has provided the health information request to the one or more covered entity computing systems, the method 900 proceeds to step 916 at which health information is received from the one or more covered entity computing systems 108. The health information may be received in response to the provider computing system 104 providing the health information request to the one or more covered entity computing systems and may be or include Rx information, Mx information, medical product information, transaction information, diagnosis information, and other health information described herein. For example, the health information may be prescription claims (Rx) information that includes deidentified PHI, medical product information, diagnosis information (e.g., a diagnosis code), HCP information (e.g., an NPI of a prescribing HCP), date/time information, facility or health care system location information, and transaction information. In another example, the health information may be medical claims (Mx) information that includes deidentified PHI, medical product information, diagnosis information (e.g., a diagnosis code), HCP information (e.g., an NPI of a prescribing HCP), date/time information, facility or health care system location information, and transaction information. Further, the received health information may correspond to or be associated with the HCP information, the consumer information, and/or the medical product information included in the health information request. For example, the health information received at step 916 may be matched with or include consumer information for each individual consumer of each prescription. For example, each piece of Rx information may be matched with demographic information associated with the consumer of the prescription. Further, the received health information may include deidentified PHI, transaction information, date/time information, and medical product information.

In some embodiments, consumer information is received from the consumer database 120 at or after step 916 and matched with the HCP information. For example, the provider computing system 104 may receive consumer information from the consumer database 120 and match the consumer information with HCPs. In this regard, the consumer information may be organized by HCP such that HCP insights or statistical values described herein may be determined from the consumer information.

As described herein, the PHI may be deidentified, by the one or more covered entity computing systems 108, in a variety of ways including through encryption, tokenization, and using a hash function. In all cases, the one or more covered entity computing systems 108 may use a consistent form of deidentification such that the same PHI input will return the same hash value or token. For example, if a piece of health information included the name "John Smith," a resulting deidentified hash value may be "1234321." To be consistent, each of the one or more covered entity computing systems, when identifying the name "John Smith," may then return the hash value "123431." By using the same hash function across the one or more covered entity computing systems, the provider computing system 104 can make additional connections between the received health information and generate HCP insights and statistical values. Further, less processing power is required by the provider computing system 104 as most of the health information matching is completed by the one or more covered entity computing systems prior to the health information being received by the provider computing system 104.

Once the provider computing system 104 has received the health information from the one or more covered entity computing systems 108, the method 900 proceeds to step 920 at which the provider computing systems 104 receives or selects government health information from the one or more national health databases 125. The government health information may include medical product information (e.g., NDC), location information (e.g., zip code for a specific Rx or Mx, state for a specific Rx or Mx, country for a specific Rx or Mx, etc.), deidentified PHI, and/or a timeframe (e.g., Jan. 1, 2022-Jan. 2, 2022) associated with the government health information. In some embodiments, the government health information includes Rx and/or Mx information and identifies whether a piece of information is Rx or Mx information. In other embodiments, the provider computing system 104 receives a first set of government health information that is Rx information and a second set of government health information that is Mx information.

As described herein, the provider computing system 104 may receive multiple sets of health information (e.g., at steps 920 and 916). For instance, the provider computing system 104 may receive first health information (e.g., at step 916) and second health information (e.g., at step 920). The first health information may be received from the one or more covered entity computing systems 108 and the second health information may be received from a health database (e.g., the national health database 125). In this regard, as described herein, the second health information may be or include government health information. In other embodiments, the order in which the health information is received may be switched. For instance, at step 916, the provider computing system 104 may receive first health information (which is or includes government health information) from the national health database 125, and at step 920, the provider computing system 104 may receive second health information from the one or more covered entity computing systems 108.

In some embodiments, the government health information is received from the one or more covered entity computing systems 108 at step 916. In some embodiments, the government health information does not include location information, and the provider computing system 104 matches or combines the government health information with the HCP location after step 916 (similar to or at step 928, as will be described further herein).

In some embodiments, after receiving the government health information and the health information, the provider computing system 104 remove duplicate health information and government health information, as discussed with regard to step 220 and 220 of the method 200.

Once the provider computing system 104 has received the government health information from the one or more covered entity computing systems 108, the method 900 proceeds to step 924 at which the provider computing system 104 selects or receives one or more digital projection models from the projection model database 135. In some embodiments, the provider computing system 104 may select one or more digital projection models based on the government health information and the health information. For example, the provider computing system 104 may select a first digital projection model from the projection model database 135 based on the volume of the health information and/or the government health information (e.g., number of unique Rx claims, number of unique Mx claims, each piece of health information, etc.). Because different digital projection models have different use cases, the provider computing system 104 may select, at step 924, the digital projection model that is best suited for the data set. For instance, prior to step 924, the provider computing system 104 may determine the availability and quality of the received data/information (e.g., the combined health information, the government health information). Then, at step 924, the provider computing system 104 may select specific models from the projection model database 135 based on the availability and quality of the received information. In one example, the provider computing system 104 may determine the received government health information is of poor quality (e.g., is outdated, is low volume, etc.) and select a projection model that only utilizes the combined health information. In another example, the provider computing system 104 may determine both sets of information are high quality and available. As a result, the provider computing system 104 may select a projection model that utilizes the combined health information and the government health information.

In some embodiments, at step 924, the provider computing system 104 may select or receive each digital projection model included within the projection model database 135. For instance, the provider computing system 104 may select a first digital projection model, a second digital projection model, and a third projection model. In some embodiments, the provider computing system 104 may select a first digital projection model from the projection model database 135 based on the health information, and the provider computing system 104 may select a second digital projection model from the digital projection model database 135 based on the government health information.

Once the provider computing system 104 has selected the one or more digital projection models from the projection model database 135, the method 900 proceeds to step 928 at which the provider computing system 104 combines the HCP location information with the health information to generate combined health information. As described herein, the provider computing system 104 may match the HCP information with the health information by determining that one or more portions of the HCP information match that of the health information. For example, the provider computing system 104 may determine that the health information includes a national provider identifier (NPI) of a prescribing physician. The provider computing system 104 may then match the NPI of the prescribing physician with the NPI of the HCP information. In some embodiments, the NPI may be a hashed or tokenized NPI such that the health information may be sorted based on each NPI of each HCP. In other embodiments, the provider computing system 104 may match one or more of a HCP name, an HCP address, an HCP specialty, or an Rx number of the health information with that of the HCP information.

Once the provider computing system 104 has matched the HCP information with the health information, the provider computing system 104 may combine the location information of the HCP information with the matching health information to generate combined health information including the health information and location information. The combined health information may be sorted or categorized or sorted based on the location. For instance, the combined health information may include a first portion (e.g., a column) grouped based on and identifiable with a first zip code, a second portion grouped based on and identifiable with a second zip code, a third portion grouped based on and identifiable with a first state, a fourth portion grouped based on and identifiable with a second state, a fifth portion grouped based on and identifiable with a first country, and/or a sixth portion grouped based on and identifiable with a second country.

In some embodiments, at or after step 928, the provider computing system 104 combines the HCP location information with the received government health information to generate combined government health information. To combine the HCP location information with the received government health information, the provider computing system 104 may do the same as described with regard to the health information and step 928.

In some embodiments, at step 928, the provider computing system 104 may aggregate at least one of the health information, the government health information, the HCP information, the consumer information, and/or the location information. For instance, the provider computing system 104 may aggregate the health information, the government health information, the HCP information, the consumer information, and/or the location information based on specific aspects of the information. For example, the provider computing system 104 may aggregate the health information based on specific medical product, based on specific timeframe (e.g., the month of May 2021), based on specific location, and/or the like. For instance, the provider computing system 104 may receive a set of health information, from the one or more covered entity computing systems 108. The health information, as described herein, may include a list of Rx or Mx claims information, deidentified PHI, and medical product information. Accordingly, the provider computing system 104, at step 928, may aggregate the health information into a count. For example, the provider computing system 104, may aggregate all health information that is for the month of May 2020, Medical product X, the prescription type Rx, and the zip code 53202. The provider computing system 104 may then repeat this aggregation for each medical product, prescription type, and location.

In some embodiments, at or after step 928, the provider computing system 104 may aggregate the government health information in the same way as the health information. In some embodiments, at or after step 928, the provider computing system 104 may aggregate the government health information with the health information. In some embodiments, the provider computing system 104 may aggregate at least one of the health information, the government health information, the HCP information, the consumer information, and/or the location information prior to selecting the digital projection models at step 924. In some embodiments, the provider computing system 104 may aggregate at least one of the health information, the government health information, the HCP information, the consumer information, and/or the location information based on the selected digital projection models. For instance, the provider computing system 104 may aggregate the at least one of the health information, the government health information, the HCP information, the consumer information, and/or the location information differently based n the selected digital projection model. For instance, a first ML digital projection model may request information aggregated differently than a second ML digital projection model.

Once the provider computing system 104 combined the HCP location information with the health information to generate combined health information, the method 900 proceeds to step 936 at which the provider computing system 104 determines one or more sets of digitally projected values based on the combined health information and/or the government health information using the one or more digital projection models. As described herein, digital projection models are models (e.g., machine-learning (ML) models, statistical models, etc.) used to determine digitally projected prescription values (i.e., total projected prescription counts) based on the known health data (e.g., the combined health data, the government health data, etc.). In some embodiments, the digital projection models are ML models that utilize a feature data set to determine digitally projected prescription values. The feature data set may include the combined health information, the government health information, the HCP information, the consumer information, and/or other information described herein. Each set of digitally projected values may include multiple digitally projected values that are each associated with a different specific location. For instance, a set of digitally projected values may include a first digitally projected value that is associated with (i.e., projected specifically for) a first location (e.g., a first zip code, first state, first country); a second projected value that is associated with (i.e., projected specifically for) a second location (e.g., a second zip code, second state, second country), and so on. In this regard, each set of digitally projected values is associated with a specific location.

In some embodiments, the provider computing system 104 may determine a set of digitally projected values for multiple dates/times (e.g., day, month, year, week), for each medical product, and for each prescription type (e.g., Mx or Rx). For instance, the provider computing system 104 may determine a first set of digitally projected values for a first month, a first prescription type, and a first medical product; a second set of digitally projected values for a second month, a second prescription type and the first medical product; a third set of digitally projected values for a second month, a first prescription type, and a second medical product; and so on. In some embodiments, the provider computing system 104 may generate a first set of digitally projected values based on the government health information using a digital projection model and a second set of digitally projected values based on the government health information and the combined health information using the digital projection model. In other embodiments, the provider computing system 104 may generate a first set of digitally projected values based on the combined health information using the digital projection model. In another example, the government health information and the combined health information may each include a first portion associated with Rx claims and a second portion associated with Mx claims. Further, the provider computing system 104 may determine a first set of digitally projected values based on the first portion of the government health information and/or the first portion of the combined health information and a second set of digitally projected values based on the second portion of the government health information and/or the second portion of the combined health information.

In some embodiments, the provider computing system 104 may determine a digitally projected value using each digital projection model within the projection model database 135. For instance, the digital projection model database 135 may include a first projection model (e.g., a binary classification projection/forecasting model), a second projection model (e.g., a CNN model), and a third projection model (e.g., a linear regression model). As a result, the provider computing system 104 may determine a first digitally projected value using the first digital projection model, a second digitally projected value using the second digital projection model, and a third digitally projected value using the third digital projection model. Further, for each digitally projected value, the provider computing system 104 may determine a confidence score or value, a lower bound value, and/or a higher bound value. Then, the provider computing system 104 may rank each of the digitally projected values (e.g., based on the respective confidence score, based on a lower bound value, based on a higher bound value) and select the best digitally projected value (e.g., the highest confidence score that is above the lower bound value and below the higher bound value, the highest confidence score, etc.).

In this regard, the provider computing system 104 may select a final set of digitally projected values based on the rank of each digitally projected value. For instance, the provider computing system 104 may determine a first set of digitally projected values, a second set of digitally projected values, and a third set of digitally projected values, using a separate digital projection model for each set. Then, the provider computing system 104 may rank each respective (e.g., for the same projection (i.e., same medical product, same timeframe, same location(s), same prescription type)) digitally projected value of the first set of digitally projected values, a second set of digitally projected values, and a third set of digitally projected values. Then, based on the rankings, the provider computing system 104 may select a final set of digitally projected values, which could include any combination of the first, second, and third set of digitally projected values. For instance, the final set of digitally projected values, may include a first digitally projected value from the first set of digitally projected values, a second digitally projected values from the third set of digitally projected values, and so on.

In some embodiments, the lower bound value, and/or the higher bound value are received by the provider computing system (e.g., from the consumer database 120, from the user computing device 112, etc.). In some embodiments, the confidence score is determined based on the digital projection model, the government health data, and/or the combined health data.

Each digitally projected value may be a projected number of prescriptions for a specific date/time or timeframe, a specific medical product, a specific location, and/a specific prescription type (e.g., Mx (in-office dispensed prescriptions claims) or Rx (pharmacy-dispensed prescription claims)). For example, because the one or more covered entity computing systems 112 do not cover or include health information associated with all possible prescriptions, the provider computing system 104 must project the missing portions of the health information. For instance, the covered entity computing systems 112 may include health information associated with 40% of all prescriptions in the United States. As a result, using the digital projection models, the provider computing system 104 may project the remaining 60% of prescriptions and determine the digitally projected values. Further, the provider computing system 104 may project the prescription numbers for each specific location (e.g., each zip code, each state, each country, etc.), for each medical product (e.g., Drug X, Vaccine Y, etc.), for each prescription type (e.g., number of Mx prescriptions and/or number of Rx prescriptions), and for each specific timeframe or date/time (e.g., for June 2021; for 2021; for Jul. 1, 2022, for the first week of June 2021, etc.). By doing so, the systems and methods described herein and the provider computing system 104 provide a technical improvement to prescription projection systems. For instance, conventional prescription projection systems only consider Rx prescriptions and do not utilize or project Mx prescriptions. While this can be suitable for certain medical products, some medical products are primarily in-office dispensed (e.g., prescribed as Mx prescriptions (e.g., Intravenous (IV) fluids, Vaccines, etc.)). As a result, conventional prescription projection systems typically cannot accurately project prescription numbers for certain medical products. In comparison, the present systems and methods project the prescription numbers for each specific prescription type including Mx prescriptions. By doing so, the present systems and methods more accurately project total prescription numbers for medical products and provide more usable and accurate digitally projected values.

In some embodiments, at or after step 936, the provider computing system 104 may further generate metadata associated with the set of digitally projected values. For instance, the provider computing system 104 may generate metadata indicating the set of digitally projected values is associated with a specific medical product, a specific timeframe, a specific location, a specific prescription type, and the like. In this regard, the metadata may be used to identify the set of digitally projected values. In other embodiments, the provider computing system 104 may generate metadata associated with each digitally projected value.

In some embodiments, at or after step 936, the provider computing system 104 may store each set of digitally projected values (e.g., within the digitally projected value database (not shown). For instance, the provider computing system 104 may add each set of digitally projected values to the digitally projected value database along with the metadata, described herein.

In some embodiments, the provider computing system 104 may generate a set of digitally projected values and use the set of digitally to determine another, summed, digitally projected value. For example, the provider computing system 104 may determine a set of digitally projected values that is associated with a specific medical product, a specific timeframe (e.g., the month of May 2021), a specification location (e.g., the zip code 53032), and a specific prescription type (e.g., Rx). In this regard, each digitally projected value may be associated with a specific day of the month of May 2021 (e.g., a first digitally projected value associated with May 1, 2021; a second digitally projected value associated with May 2, 2021; and so on). Then, to determine a summed digitally projected value for May 2021, the provider computing system 104 may sum the set of digitally projected values.

Once the provider computing system 104 has determined the one or more sets of digitally projected values, the method 900 proceeds to step 948 at which the provider computing system 104 receives a defined location prescribing file generation request from the user computing device 112. As described herein, the defined location prescribing file generation request may indicate one or more insights or statistical values (e.g., median quantity dispensed of a medical product, total number of Rx prescriptions, total number of Mx prescriptions, the number of switches which occurred in the state, percentage of generic medical products prescribed or administered versus name brand medical products, etc.) as well as include a file destination address to which the HCP file is to be provided. Further, the defined location prescribing file generation request may define or identify one or more locations for which prescribing information is sought. In this regard, each defined location may include or be associated with multiple specific locations. For instance, the defined location prescribing file generation request may identify one or more zip codes, one or more states, one or more countries, etc. In some embodiments, the defined location prescribing file generation request may also identify or include a specified file format that the defined location prescribing file is to be. For example, the defined location prescribing file generation request may indicate the defined location prescribing file is to be generated as a .CSV file delimited with commas.

In some embodiments, the defined location prescribing file generation request may also identify the medical product (s), a frequency, and/or a timeframe for which health information is sought. For example, the defined location prescribing file generation may indicate a specific medical product (e.g., drug X), a specific timeframe (e.g., Jan. 1, 2021-Jan. 1, 2022), a type of prescriptions (e.g., Mx prescriptions and/or Rx prescriptions) that are sought, and a frequency (e.g., weekly) for which digitally projected values are sought and to be filtered.

Once the provider computing system 104 received the defined location prescribing file generation request from the user computing device 112, the method 900 proceeds to step 950 at which the provider computing system 104 filters the digitally projected values based on the defined location prescribing file generation request. For example, the provider computing system 104 may filter the sets of digitally projected values based on the defined location prescribing file generation request by removing digitally projected values that do not match or are not associated with the medical product(s), defined location, frequency, and/or timeframe of the defined location prescribing file generation request. As described herein, each digitally projected value may be associated with a specific location (e.g., zip code 123, state X, country X, etc.), a specific prescription type (e.g., Mx or Rx), a specific timeframe or date/time (e.g., the month of January 2021; the year 2022; Jan. 1, 2021; etc.), and/or a specific medical product (e.g., drug X, Vaccine Y, etc.). In this regard, to filter the sets of digitally projected values, the provider computing system 104 may parse each set of digitally projected values and remove digitally projected values that do not match the specific location, specific timeframe, specific prescription type, and/or the specific medical product of the defined location prescribing file generation request. In some embodiments, to filter the sets of digitally projected values, the provider computing system 104 may parse each set of digitally projected values and select digitally projected values that match the specific location, specific timeframe, specific prescription type, and/or the specific medical product of the defined location prescribing file generation request.

As described herein, each set of digitally projected values may be associated with a specific medical product, timeframe, location, prescription type, etc. As a result, to filter the sets of digitally projected values, the provider computing system 104 may remove the sets of digitally projected values that do not match the specific location, specific timeframe, specific prescription type, and/or the specific medical product of the defined location prescribing file generation request. In some embodiments, to filter the sets of digitally projected values, the provider computing system 104 may parse each set of digitally projected values and select the sets of digitally projected values that do match the specific location, specific timeframe, specific prescription type, and/or the specific medical product of the defined location prescribing file generation request.

In some embodiments, at step 950, the provider computing system 104 may select digitally projected values from the digitally projected value database (not shown). Accordingly, the provider computing system 104 may filter the digitally projected values by only querying the digitally projected value database for a select set of the digitally projected values. For instance, at step 950, the provider computing system 104 may select or query the digitally projected value database for digitally projected values that are associated with a specific timeframe, a specific medical product, a specific prescription type, a specific location, and the like. In this regard, the digitally projected value database may return values that match the query based on the metadata of the digitally projected values meeting or being the same as the defined location prescribing file generation request (e.g., the same location, the same prescription type, etc.).

Once the provider computing system 104 has filtered the digitally projected values, the method 900 proceeds to step 952 at which the provider computing system 104 generates a defined location prescribing file including (e.g., populated with) at least one of the one or more sets of digitally projected values and/or the location information (e.g., of the combined health information and the government health information). For example, the provider computing system 104 may populate the defined location prescribing file with the filtered sets of digitally projected values or the filtered digitally projected values. Further, the provider computing system 104 may populate the defined location prescribing file with the locations that correspond or are associated with the filtered sets of digitally projected values or the filtered digitally projected values, the timeframes or date/times that correspond or are associated with the filtered sets of digitally projected values or the filtered digitally projected values, the specific prescription type(s) that are associated with the filtered sets of digitally projected values or the filtered digitally projected values, and/or the specific medical product that are associated with the filtered sets of digitally projected values or the filtered digitally projected values. FIG. 11 shows an example defined location prescribing file 1100, and the respective fields populated by the provider computing system 104.

Additionally, the provider computing system 104 may structure the defined location prescribing file based on the destination address of the defined location prescribing file generation request and/or the specific file type of the defined location prescribing file generation request. For example, the provider computing system 104 may populate the defined location prescribing file with the filtered digitally projected values and the location information in a specific order based on the defined location prescribing file generation request and the recipient address of the defined location prescribing file generation request. For instance, if the defined location prescribing file is to be provided to the user computing device 112 (e.g., the destination address is the IP address of the user computing device 112), the provider computing system 104 may structure the defined location prescribing file to include a specific header for each set of digitally projected values and for each defined location. In comparison, if the defined location prescribing file is to be provided to another portion of the provider computing system 104 (e.g., Veeva Nitro), the provider computing system 104 may structure the HCP file to include a specific row for each set of digitally projected values and multiple rows for each location.

Moreover, the defined location prescribing file may be generated as a specific file type as indicated by the user computing device 112 in the defined location prescribing file. For example, the defined location prescribing file may be generated as a CSV file, an Excel File (XLSX file), an XML file, a JSON file, and the like. By allowing the user (e.g., via the user computing device 112) to decide the specific file type of the HCP file in the HCP file generation request and not only generating the defined location prescribing file as one specific file type, the provider computing system 104 may provide for improved shareability of the defined location prescribing file as well as use less processing power and memory. For example, in situations where the defined location prescribing file is only generated as a specific, non-dynamic, file type, third-party computing systems and recipient computing devices (e.g., the recipient computing device 116) may have to perform additional file modification and conversion or request the provider computing system 104 to do so, which requires additional processing power, memory (to keep two files), and time. In comparison, the system 100 and the provider computing system 104 allow the user to specify the file type of the defined location prescribing file through the defined location prescribing file generation request. Accordingly, the user can specify the wanted file type the first time and the provider computing system 104 will generate the defined location prescribing file as the specified file type. As a result, no additional file modification or conversion is required reducing processing power usage, memory usage, and overall processing time for the provider computing system 104.

Once the provider computing system 104 has generated the defined location prescribing file, the method 900 proceeds to step 956 at which the at which the HCP file is provided to the file destination address of the defined location prescribing file generation request. The file destination address may be any type of address or destination (e.g., IP address, web address, email address, file transfer protocol (FTP) address, and the like) to which the defined location prescribing file may be electronically transmitted or provided. In one example, the file destination address may be another server or circuit of the provider computing system 104 that is configured to receive the defined location prescribing file (e.g., Veeva Nitro®). In another example, the file destination address may be a web address of the Amazon Simple Storage Service® cloud storage web service. In another example, the file destination address may be the IP address of the user computing device 112 and the defined location prescribing file may be provided to the user computing device 112.

Figure 10A:
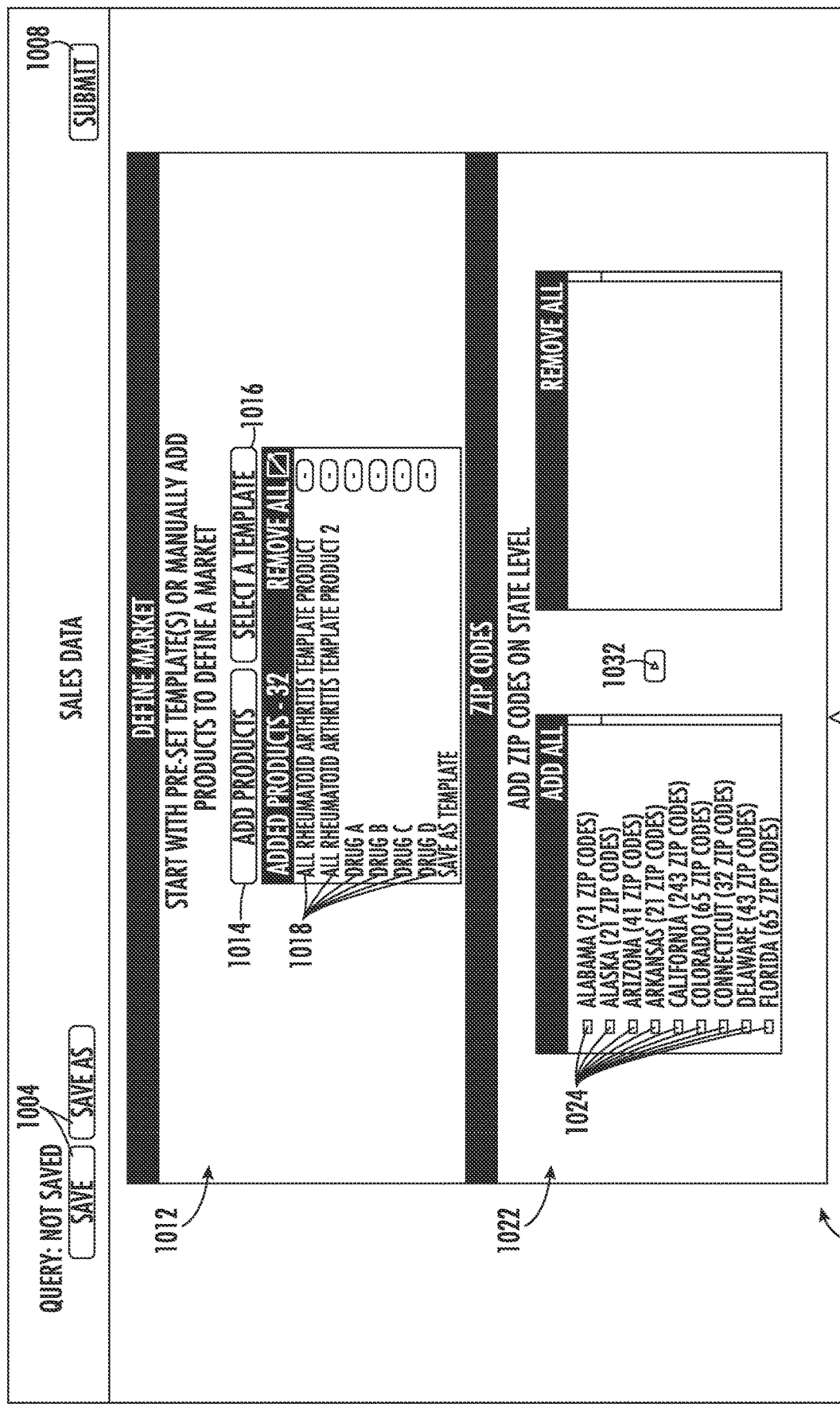
FIGS. 10A-10B are multiple illustrations of some aspects of a user interface generated by the longitudinal health information analyzation and dynamically structured electronic file generation system of FIG. 1 to receive a defined location prescribing file generation request, according to an example embodiment.
Figure 10B:
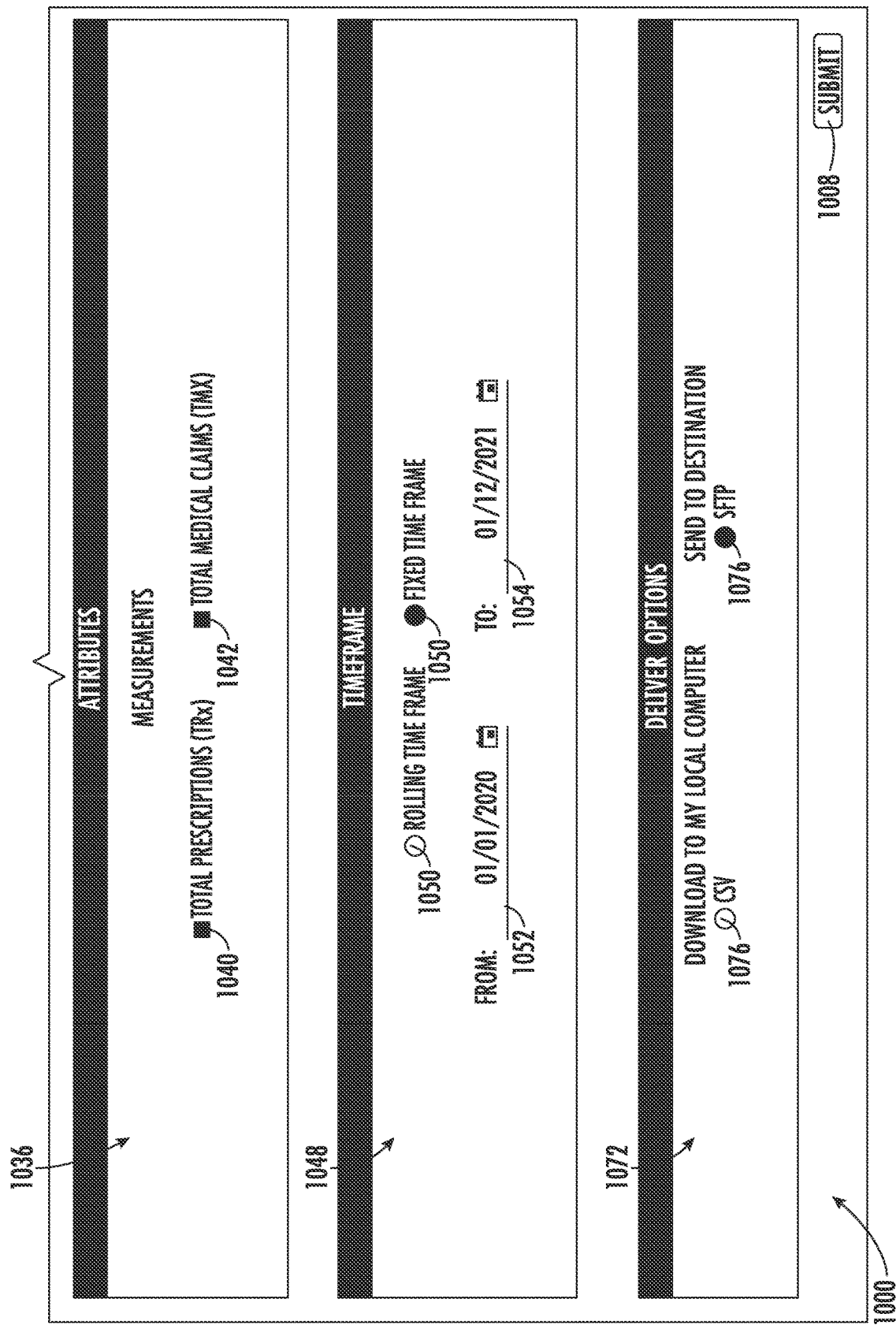

Referring now to FIGS. 10A-10B, user interfaces shown to the user of the user computing device 112 during the method 200 and/or the method 900 are shown, according to example embodiments. As described herein, the user interfaces of FIGS. 10-10B may be one or more of web interfaces generated by the provider computing system 104 and rendered by the user computing device 112 as part of a web application or graphical user interfaces downloaded and generated by the user computing device 112 as part of a software application (e.g., mobile application, etc.). Further, the user interfaces shown on FIGS. 10A-10B allow for communication between the user and the provider computing system 104 via the user computing device 112 (specifically via the I/O circuit 180). Through interaction with the various user interfaces, the user may provide user input, feedback, and other information requested by the provider computing system 104. In this regard, it should be understood that each interaction described herein by the user with the user interfaces of FIGS. 10A-10B may be provided to the user computing device 112 and then transmitted to the provider computing system 104 and that each action described herein as occurring to or on the user computing device 112 (e.g., navigating to a certain page, generating a popup, etc.) may be performed by the provider computing system 104.

Still referring to FIGS. 10A-10B, a defined location prescribing file generation request page 1000 (or prescribing file request page 1000, for short), which can be displayed on a display of the I/O circuit 148 of the user computing device 112, is shown. In general, the prescribing file request page 1000 provides the user with an interface to generate and provide a defined location prescribing file generation request to the provider computing system 104. For example, through interaction with the prescribing file request page 1000 the user of the user computing device 112 can generate a defined location prescribing file indicating how the combined health information, the government health information, the sets of digitally projected values, the location information, and/or the consumer information should be filtered; identifying the file destination, identifying the file type of the defined location prescribing file; and indicating one or more statistical values or insights that are to be generated. To access or be navigated to the prescribing file request page 1000, the user of the user computing device 112 may navigate to the information selection page 300 (e.g., by selecting the pull data button 304), then select the prescription sales information option 328 or the national prescription information option 332, and then select the next button 336.

As shown, the prescribing file request page 1000 includes multiple save buttons 1004 (e.g., "Save" and "Save As), a submit button 1008, a medical product selection section 1012 (which may be similar to the filter section 424 of the HCP request page 400), a location selection section 1022, a prescription type selection section 1036, a timeframe section 1048, and a delivery menu 1072 (which may be similar to the delivery menu 472 of the HCP request page 400).

The save buttons 1004 allow the user of the user computing device to save the current defined location prescribing file generation request such that they can return to it at another point in time. The "Save As" button may provide a popup menu or box through which the user can name the current HCP file generation request or overwrite another saved defined location prescribing file generation request. The "Save" button may simply save a pre-named or selected defined location prescribing file generation request such that the user can return to it under that pre-selected name at another point in time. When the user selects either of the save buttons 1004, the user computing device 112 may generate an defined location prescribing file generation request, with the currently selected information and details of the prescribing file request page 1000 (including empty fields where the user has not made a selection yet) and provide the defined location prescribing file generation request to the provider computing system 104 with an indication that it is to be saved (but not used to generate an defined location prescribing file). The provider computing system 104 may receive the indication and the defined location prescribing file generation request and save the defined location prescribing file generation request (and accompanying selected information and name) in association with the account of the user. For example, the provider computing device may provide the defined location prescribing file generation request and accompanying information to the account database 132 for storage.

The medical product selection section 1012 is a section of the prescribing file request page 1000 through which the user of the user computing device 112 can customize and select the specific medical products to include in the defined location prescribing file generation request and to be used in generating the defined location prescribing file. As shown, the medical products selection section 1012 includes an add products button 1014, a select a template button 1016, and multiple added product fields 1018. The medical product selection section may be similar or the same as the medical product information filters 432 of the HCP file request page 400. Accordingly, the add products button 1014, the select a template button 1016, and the multiple added product fields 1018 may be used to add medical products to the defined location prescribing file generation request, as described herein.

For instance, the user, via the prescribing file request page 1000, may select one or more product fields or defined markets 1018 (e.g., Drug A, Drug B, All Rheumatoid Arthritis products, all Colon Cancer products, other medical product groups, etc.). Then, the user may select the add products button 1014 to add the products to the defined location prescribing file generation request, which may be provided to the provider computing system 104 (e.g., with the selection of the submit button 1008) and used to filter the digitally projected values. In some embodiments, if the user selects the select a template button 1016, the user may be navigated to the medical product group selection page 500, where the user can generate and select one or more medical product groups.

The location selection section 1022 is a section of the prescribing file request page 1000 through which the user of the user computing device 112 can customize and select the specific locations to include in the defined location prescribing file generation request and to be used in generating the defined location prescribing file. As shown, the location selection section 1022 includes multiple location checkboxes or options 1024 and an add button 1032. Accordingly, the multiple location checkboxes 1024 and the add button 1032 may be used to define (i.e., add locations to) the defined location of the defined location prescribing file generation request, as described herein.

For instance, the user, via the prescribing file request page 1000, may select one or more location checkboxes 1024 (e.g., the state of Alabama, the state of Wisconsin, the zip code of 53039, the zip code of 53209, the zip code 53703, the country USA, the country Canada, etc.). Then, the user may select the add button 1032 to define the defined location and add the defined location to the defined location prescribing file generation request, which may be provided to the provider computing system 104 (e.g., with the selection of the submit button 1008) and used to filter the digitally projected values.

The prescription type selection section 1036 is a section of the prescribing file request page 1000 through which the user of the user computing device 112 can customize and select the specific prescription types (e.g., Mx or Rx) to include in the defined location prescribing file generation request and to be used in generating the defined location prescribing file. As shown, the prescription type selection section 1036 includes a total prescriptions (TRx) checkbox 1040 and a total medical claims (TMx) checkbox 1042. Accordingly, the TRx checkbox 1040 and the TMx checkbox 1042 may be used to add the specific prescription type(s) to the defined location prescribing file generation request, as described herein.

For instance, the user, via the prescribing file request page 1000, may select the TRx checkbox 1040 and/or the TMx checkbox 1042. The selected prescription type(s) (e.g., Mx and/or Rx) may then be added to the defined location prescribing file generation request and provided to the provider computing system 104 (e.g., with the selection of the submit button 1008). The selected prescription type(s) may then be used to filter the digitally projected values.

The timeframe selection section 1048 is a section of the prescribing file request page 1000 through which the user of the user computing device 112 can customize and select the specific timeframe to include in the defined location prescribing file generation request and to be used in generating the defined location prescribing file. As shown, the timeframe selection section 1048 includes multiple timeframe type checkboxes 1050, a start date field 1052, and an end date field 1054. In some embodiments, the timeframe selection section 1048 may further include one or more frequency checkboxes (not shown). The frequency checkboxes may be selectable to add a specific requested frequency (e.g., daily, weekly, monthly, yearly) to the defined location prescribing file generation request, as described herein. Further, the timeframe type checkboxes 1050, the start date field 1052, the end date field 1054, and/or the frequency checkboxes may be used to add the timeframe and/or the specified frequency to the defined location prescribing file generation request, as described herein.

For instance, the user, via the prescribing file request page 1000, may select or set a start date via the start date field 1052 (e.g., Jun. 1, 2021) and select or set an end date via the end date field 1054 (e.g., Jun. 1, 2022), thereby setting a timeframe (e.g., Jun. 1, 2021-Jun. 1, 2022). The timeframe may then be added to the defined location prescribing file generation request and provided to the provider computing system 104 (e.g., with the selection of the submit button 1008). The timeframe may then be used to filter the digitally projected values.

The delivery menu 1072 is a section of the prescribing file request page 1000 through which the user of the user computing device 112 can customize and select the file type and the file destination address to include in the defined location prescribing file generation request and to be used in generating the defined location prescribing file. As shown, the delivery menu 1072 includes a first checkbox 1076 and a second checkbox 1080. The delivery menu 1072 may be similar or the same as the delivery menu 472 of the HCP file request page 400. Accordingly, the first checkbox 1076 and the second checkbox 1080 may be used to add file type(s) and/or destination address(es) to the defined location prescribing file generation request, as described herein.

Referring now FIG. 11, an electronic file 1100 (also referred to as a defined location prescriber file 1100) is shown according to an example embodiment. The electronic file 1100 is shown to include a product name for each medical product and location, a month time frequency, a timeframe of Jan. 1, 2021 to Feb. 1, 2021, multiple locations (e.g., the zip code 90640, the zip code 00680, the zip code 08822, etc.), a prescription type of Rx, and a digitally projected value for each location.

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FBGAs), digital signal processors (DSPs), or other suitable electronic data processing components structured to execute instructions provided by the memory. The one or more processors may take the form of a single core processor, a multi-core processor (e.g., dual core, quad core, etc.), microprocessor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a give circuit or components thereof may be disposed locally (e.g., as part of a local server, a local computing system) or remotely (e.g., as part of a remote server such as a cloud-based server). To that end, a "circuit" as described herein may include components that are distributed across one or more locations.

An example system for implementing the overall system or portions of the embodiments might include a general purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general purpose computer, special purpose computer, or special purpose processing machine to perform a certain function or group of functions. Each respective memory device may be operable to maintain or otherwise store information relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for generating a dynamically structured electronic file in a dynamic file generation system, wherein the dynamic file generation system comprises a provider computing system, one or more covered entity computing systems, and a user computing device associated with a user connected by a secure network, the method comprising:

receiving, by a network interface circuit of the provider computing system, first health information including location information from a national health database;

generating, by a processing circuit of the provider computing system, a health information request;

providing, by the network interface circuit of the provider computing system, the health information request to the one or more covered entity computing systems;

receiving, by the network interface circuit, second health information including prescription claim (Rx) health information and medical claim (Mx) health information from the one or more covered entity computing systems, wherein the Rx health information includes first deidentified protected health information (PHI), and wherein the Mx health information includes second deidentified protected health information (PHI);

receiving, by the network interface circuit, health care provider (HCP) information including HCP location information;

combining, by the processing circuit, the Rx health information with at least a portion of the HCP location information to generate first combined health information;

combining, by the processing circuit, the Mx health information with at least a portion of the HCP location information to generate second combined health information;

selecting, by the processing circuit, one or more digital projection models from a projection model database of the provider computing system;

determining, by the processing circuit, a first plurality of digitally projected values based on at least one of the first combined health information or the Rx health information using at least one of the one or more digital projection models, wherein each digitally projected value of the first plurality of digitally projected values is projected for prescription claims and associated with time information;

determining, by the processing circuit, a second plurality of digitally projected values based on at least one of the second combined health information or the Mx health information using at least one of the one or more digital projection models, wherein each digitally projected value of the second plurality of digitally projected values is projected for medical claims and associated with time information;

receiving, by the network interface circuit, a file generation request from the user computing device, the file generation request identifying a file type, a timeframe, and a file destination address;

filtering, by the processing circuit, the first plurality of digitally projected values for the timeframe of the file generation request by removing digitally projected values with time information that are not within the timeframe;

filtering, by the processing circuit, the second plurality of digitally projected values for the timeframe of the file generation request by removing digitally projected values with time information that are not within the timeframe;

generating, by the processing circuit, the electronic file including at least one digitally projected value of the filtered first plurality of the digitally projected values, at least one digitally projected value of the filtered second plurality of the digitally projected values, and at least a portion of the HCP location information or the location information, wherein the electronic file is generated as the file type identified by the file generation request, and wherein the electronic file is structured based on at least one of the file generation request or the file destination; and providing, by the network interface circuit, the electronic address to the file destination address of the file generation request.

2. The method of claim 1, further comprising:

receiving, by the network interface circuit, a file share request from the user computing device, the file share request including a recipient address and a file share expiration date;

receiving, by the network interface circuit, a request to access the electronic file from a recipient computing device associated with the recipient address;

determining, by the processing circuit, that a present date is before the expiration date;

providing, by the network interface circuit and in response to determining that the present date is before the expiration date, the electronic file to the recipient computing device associated with the recipient address based on the request to access the electronic file.

3. The method of claim 2, further comprising:

generating, by the processing circuit and in response to receiving the file share request, an indication comprising a uniform resource locator (URL) including an expiration parameter that deactivates the URL on the file share expiration date; and providing, by the network interface circuit, the indication to the recipient computing device associated with the recipient address.

4. The method of claim 1, wherein each digital projection model of the one or more digital projections models is at least one of: a binary classification model, a neural network model, a multiclass classification model, or a regression model.

5. The method of claim 1, wherein the one or more digital projection models is a plurality of digital projection models, wherein the first plurality of digitally projected values is a plurality of sets of digitally projected values, and wherein the provider computing system determines a confidence score for each digitally projected value of a set of digitally projected values using each digital projection model.

6. The method of claim 5, further comprising:

ranking, by the processing circuit, each digitally projected value based on the confidence score;

selecting, by the processing circuit, a final set of digitally projected values based on the rankings; and filtering, by the processing circuit, the final set of digitally projected values for the defined location of the file generation request by removing digitally projected values that are not associated with the defined location.

7. The method of claim 1, wherein the one or more covered entity computing systems comprise a first covered entity computing system associated with a pharmacy and a second covered entity computing system associated with a medical claims company, wherein the combined health information is first combined health information, and wherein the method further comprises:

receiving, by the network interface circuit, the Rx health information from the first covered entity computing system;

receiving, by the network interface circuit, the Mx health information from the second covered entity computing system.

8. The method of claim 7, further comprising:

determining, by the processing circuit, the first combined health information includes duplicate health information; and modifying, by the processing circuit, the first combined health information to remove the duplicate health information.

9. The method of claim 1, wherein each digitally projected value of the plurality of digitally projected values is associated with a specific location, wherein the file generation request identifies a defined location, and wherein the method further comprises:

filtering, by the processing circuit, the first plurality of digitally projected values for the defined location of the file generation request by removing digitally projected values that are not associated with the defined location.

10. The method of claim 9, wherein the defined location includes a plurality of locations, and wherein each location of the plurality of locations is at least one of: a country, a state, or a zip code.

11. The method of claim 1, wherein the first health information is national health insurance information associated with at least one of Medicaid or Medicare.

12. A method for generating a dynamically structured electronic file in a dynamic file generation system, wherein the dynamic file generation system comprises a provider computing system, one or more covered entity computing systems, and a user computing device connected by a secure network, the method comprising:

receiving, by a network interface circuit of the provider computing system, first health information including location information from a national health database;

receiving, by the network interface circuit, second health information including prescription claim (Rx) health information and medical claim (Mx) health information from the one or more covered entity computing systems, wherein the Rx health information includes first deidentified protected health information (PHI), and wherein the Mx health information includes second deidentified protected health information (PHI);

receiving, by the network interface circuit, health care provider (HCP) information including HCP location information;

combining, by the processing circuit, the Rx health information with at least a portion of the HCP location information to generate first combined health information;

combining, by the processing circuit, the Mx health information with at least a portion of the HCP location information to generate second combined health information;

selecting, by the processing circuit, one or more digital projection models from a projection model database of the provider computing system;

determining, by the processing circuit, a first set of digitally projected values based on the first health information using the one or more digital projection models;

determining, by the processing circuit, a second set of digitally projected values based on the first combined health information and the first health information using at least one of the one or more digital projection models, wherein each digitally projected value of the first set of digitally projected values associated with time information, wherein each digitally projected value of the second set of digitally projected values is projected for prescription claims and associated with time information;

determining, by the processing circuit, a third set of digitally projected values based on the second combined health information and the first health information using at least one of the one or more digital projection models, wherein each digitally projected value of the third set of digitally projected values is projected for medical claims and associated with time information;

receiving, by the network interface circuit, a file generation request from the user computing device, the file generation request identifying a file type, a timeframe, and a file destination address;

filtering, by the processing circuit, the first set of digitally projected values for the timeframe of the file generation request by removing digitally projected values with time information that are not within the timeframe;

filtering, by the processing circuit, the second set of digitally projected values for the timeframe of the file generation request by removing digitally projected values with time information that are not within the timeframe;

filtering, by the processing circuit, the third set of digitally projected values for the timeframe of the file generation request by removing digitally projected values with time information that are not within the timeframe;

generating, by the processing circuit, the electronic file including at least one digitally projected value of the filtered first set of digitally projected values, the second set of digitally projected values, or the filtered second set of digitally projected values, wherein the electronic file includes at least a portion of the location information or the HCP location information, wherein the electronic file is generated as the file type identified by the file generation request, and wherein the electronic file is structured based on at least one of the file generation request or the file destination; and providing, by the network interface circuit, the electronic address to the file destination address of the file generation request.

13. The method of claim 12, wherein each digitally projected value of the first set of digitally projected values and the second set of digitally projected values is associated with a specific location, wherein the file generation request identifies a defined location, and wherein the method further comprises:

filtering, by the processing circuit, the first set of digitally projected values and the second set of digitally projected values for the defined location of the file generation request by removing digitally projected values that are not associated with the defined location.

14. The method of claim 13, wherein the defined location includes a plurality of locations, and wherein each location of the plurality of locations is at least one of: a country, a state, or a zip code.

15. The method of claim 12, wherein the first health information is government health information comprising a first portion associated with prescription claims and a second portion associated with medical claims.

16. The method of claim 15, wherein the first set of digitally projected values comprises a first plurality of digitally projected values and a second plurality of digitally projected values, and wherein determining the first set of projected values comprises:

determining, by the processing circuit, the first plurality of digitally projected values based on the first portion of the government health information using at least one of the one or more digital projection models; and determining, by the processing, the second plurality of digitally projected values based on the second portion of the government health information using at least one of the one or more digital projection models.

17. The method of claim 12, wherein each digital projection model of the one or more digital projections models is at least one of: a binary classification model, a neural network model, a multiclass classification model, or a regression model.

18. The method of claim 12, wherein the one or more covered entity computing systems comprise a first covered entity computing system associated with a pharmacy and a second covered entity computing system associated with a medical claims company, wherein the combined health information is first combined health information, and wherein the method further comprises:

receiving, by the network interface circuit, the Rx health information from the first covered entity computing system;

receiving, by the network interface circuit, the Mx health information from the second covered entity computing system.

19. The method of claim 12, wherein each digitally projected value of the first set of digitally projected values and each digitally projected value of the second set of digitally projected values is associated with a specific month and a specific year, wherein the first set of digitally projected values are filtered to remove digitally projected values in which the specific month and the specific year do not fall within the timeframe, and wherein the second set of digitally projected values are filtered to remove digitally projected values in which the specific month and the specific year do not fall within the timeframe.

* * * * *